(12) United States Patent
Connor

(10) Patent No.: US 12,405,211 B2
(45) Date of Patent: Sep. 2, 2025

(54) NERD OF THE RINGS (SMART RING WITH SPECTROSCOPIC SENSORS)

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 18/775,128

(22) Filed: Jul. 17, 2024

(65) Prior Publication Data

US 2024/0377316 A1    Nov. 14, 2024

Related U.S. Application Data

(63) Continuation-in-part of application No. 18/617,950, filed on Mar. 27, 2024, and a continuation-in-part of application No. 18/121,841, filed on Mar. 15, 2023, said application No. 18/617,950 is a continuation-in-part of application No. 18/121,841, filed on Mar. 15, 2023, which is a continuation-in-part of application No. 17/903,746, filed on Sep. 6, 2022, now abandoned, and a continuation-in-part of application No. 17/239,960, filed on Apr. 26, 2021, now abandoned, said application No. 17/903,746 is a continuation-in-part of application No. 17/239,960, filed on Apr. 26, 2021, now abandoned, and a continuation-in-part of application No. 16/737,052, filed on Jan. 8, 2020, now Pat. No. 11,754,542, said application No.

(Continued)

(51) Int. Cl.
  *G01N 21/31*  (2006.01)
  *A61B 5/00*   (2006.01)
  *G01N 33/02*  (2006.01)

(52) U.S. Cl.
  CPC ............. *G01N 21/31* (2013.01); *G01N 33/02* (2013.01); *A61B 5/0075* (2013.01); *A61B 5/6802* (2013.01)

(58) Field of Classification Search
  CPC ... A61B 5/0075; A61B 5/6802; A61B 5/1455; A61B 5/6826
  See application file for complete search history.

(56) References Cited

U.S. PATENT DOCUMENTS

| 3,790,249 A | * | 2/1974 | Treace | G02B 21/06 359/388 |
| 5,928,158 A | * | 7/1999 | Aristides | A61B 18/20 604/116 |

(Continued)

FOREIGN PATENT DOCUMENTS

| CN | 204180114 U | * | 2/2015 |
| KR | 2009020438 A | * | 2/2009 |

*Primary Examiner* — Jacqueline Cheng
*Assistant Examiner* — Tho Q Tran

(57) ABSTRACT

This invention is a smart ring with spectroscopic sensors. Changes in the spectrum of light which are caused by interaction with (e.g. reflection by or transmission through) matter are analyzed to get information about the composition of that matter. In an example, light emitters can direct light outward toward an environmental object to get information concerning the molecular composition of the object. In an example, light emitters can direct light inward toward the surface of a person's finger to measure one or more biometric parameters.

4 Claims, 4 Drawing Sheets

Related U.S. Application Data

17/239,960 is a continuation-in-part of application No. 16/737,052, filed on Jan. 8, 2020, now Pat. No. 11,754,542, said application No. 18/121,841 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, said application No. 17/903,746 is a continuation-in-part of application No. 16/568,580, filed on Sep. 12, 2019, now Pat. No. 11,478,158, said application No. 16/737,052 is a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, and a continuation-in-part of application No. 15/944,746, filed on Apr. 3, 2018, now abandoned, said application No. 16/737,052 is a continuation-in-part of application No. 15/725,330, filed on Oct. 5, 2017, now Pat. No. 10,607,507, said application No. 16/568,580 is a continuation-in-part of application No. 15/725,330, filed on Oct. 5, 2017, now Pat. No. 10,607,507, said application No. 16/737,052 is a continuation-in-part of application No. 15/431,769, filed on Feb. 14, 2017, now abandoned, said application No. 15/725,330 is a continuation-in-part of application No. 15/431,769, filed on Feb. 14, 2017, now abandoned, said application No. 16/568,580 is a continuation-in-part of application No. 15/431,769, filed on Feb. 14, 2017, now abandoned, and a continuation-in-part of application No. 15/418,620, filed on Jan. 27, 2017, now abandoned, said application No. 15/431,769 is a continuation-in-part of application No. 15/294,746, filed on Oct. 16, 2016, now Pat. No. 10,627,861, said application No. 16/737,052 is a continuation-in-part of application No. 15/294,746, filed on Oct. 16, 2016, now Pat. No. 10,627,861, said application No. 15/431,769 is a continuation-in-part of application No. 15/206,215, filed on Jul. 8, 2016, now abandoned, said application No. 15/963,061 is a continuation-in-part of application No. 14/992,073, filed on Jan. 11, 2016, now abandoned, said application No. 15/431,769 is a continuation-in-part of application No. 14/992,073, filed on Jan. 11, 2016, now abandoned, said application No. 15/206,215 is a continuation-in-part of application No. 14/951,475, filed on Nov. 24, 2015, now Pat. No. 10,314,492, said application No. 15/418,620 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/725,330 is a continuation-in-part of application No. 14/951,475, filed on Nov. 24, 2015, now Pat. No. 10,314,492, said application No. 15/206,215 is a continuation-in-part of application No. 14/948,308, filed on Nov. 21, 2015, now abandoned, said application No. 14/992,073 is a continuation-in-part of application No. 14/562,719, filed on Dec. 7, 2014, now Pat. No. 10,130,277, said application No. 14/948,308 is a continuation-in-part of application No. 14/550,953, filed on Nov. 22, 2014, now abandoned, said application No. 15/963,061 is a continuation-in-part of application No. 14/550,953, filed on Nov. 22, 2014, now abandoned, said application No. 14/948,308 is a continuation-in-part of application No. 14/449,387, filed on Aug. 1, 2014, now abandoned, said application No. 15/431,769 is a continuation-in-part of application No. 14/330,649, filed on Jul. 14, 2014, now abandoned, said application No. 14/948,308 is a continuation-in-part of application No. 14/132,292, filed on Dec. 18, 2013, now Pat. No. 9,442,100, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449, said application No. 14/948,308 is a continuation-in-part of application No. 13/901,099, filed on May 23, 2013, now Pat. No. 9,254,099, said application No. 14/992,073 is a continuation-in-part of application No. 13/616,238, filed on Sep. 14, 2012, now abandoned, said application No. 14/330,649 is a continuation-in-part of application No. 13/523,739, filed on Jun. 14, 2012, now Pat. No. 9,042,596.

(60) Provisional application No. 63/542,077, filed on Oct. 2, 2023, provisional application No. 63/279,773, filed on Nov. 16, 2021, provisional application No. 63/171,838, filed on Apr. 7, 2021, provisional application No. 62/930,013, filed on Nov. 4, 2019, provisional application No. 62/857,942, filed on Jun. 6, 2019, provisional application No. 62/814,692, filed on Mar. 6, 2019, provisional application No. 62/814,713, filed on Mar. 6, 2019, provisional application No. 62/800,478, filed on Feb. 2, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/297,827, filed on Feb. 20, 2016, provisional application No. 62/245,311, filed on Oct. 23, 2015, provisional application No. 61/932,517, filed on Jan. 28, 2014.

(56) References Cited

U.S. PATENT DOCUMENTS

| | | | |
|---|---|---|---|
| 6,402,690 B1* | 6/2002 | Rhee | A61B 5/0002 600/323 |
| 8,175,667 B2* | 5/2012 | Debreczeny | A61B 5/14552 600/323 |
| 9,582,034 B2 | 2/2017 | von Badinski et al. | |
| 10,156,867 B2 | 12/2018 | von Badinski et al. | |
| 10,349,847 B2 | 7/2019 | Kwon et al. | |
| 10,444,834 B2 | 10/2019 | Vescovi | |
| 10,739,820 B2 | 8/2020 | Wang et al. | |
| 10,768,666 B2 | 9/2020 | von Badinski et al. | |
| 10,842,429 B2 | 11/2020 | Kinnunen et al. | |
| 10,893,833 B2 | 1/2021 | Haverinen et al. | |
| 11,188,124 B2 | 11/2021 | von Badinski et al. | |
| 11,188,160 B1 | 11/2021 | Liu | |
| 11,275,453 B1 | 3/2022 | Tham et al. | |
| 11,462,107 B1 | 10/2022 | Sanchez | |
| 11,479,258 B1 | 10/2022 | Sanchez | |
| 11,540,599 B1 | 1/2023 | Yokoyama et al. | |
| 11,580,300 B1 | 2/2023 | Tham et al. | |
| 11,599,147 B2 | 3/2023 | von Badinski et al. | |
| 11,660,228 B2 | 5/2023 | Goff et al. | |
| 11,666,230 B1 | 6/2023 | Piccinini et al. | |
| 11,714,494 B2 | 8/2023 | D'Amone et al. | |
| 11,733,790 B2 | 8/2023 | Beyhs et al. | |
| 11,793,454 B2 | 10/2023 | Kinnunen et al. | |

(56) References Cited

U.S. PATENT DOCUMENTS

| | | |
|---|---|---|
| 11,829,831 B1 | 11/2023 | Ershov et al. |
| 11,850,069 B1 | 12/2023 | Mars et al. |
| 11,864,871 B2 | 1/2024 | Kang et al. |
| 11,868,178 B2 | 1/2024 | von Badinski et al. |
| 11,868,179 B2 | 1/2024 | von Badinski et al. |
| 11,874,701 B2 | 1/2024 | von Badinski et al. |
| 11,874,702 B2 | 1/2024 | von Badinski et al. |
| 11,895,383 B2 | 2/2024 | Prushinskiy et al. |
| 11,902,791 B2 | 2/2024 | Mars et al. |
| 11,911,181 B1 | 2/2024 | Huttunen et al. |
| 11,916,900 B2 | 2/2024 | Mars et al. |
| 11,925,441 B1 | 3/2024 | Rantanen et al. |
| 11,937,905 B2 | 3/2024 | Singleton et al. |
| 11,949,673 B1 | 4/2024 | Sanchez |
| 11,980,439 B2 | 5/2024 | Koskela et al. |
| 11,986,313 B2 | 5/2024 | Kinnunen et al. |
| 12,007,727 B2 | 6/2024 | Leith et al. |
| 12,013,725 B2 | 6/2024 | von Badinski et al. |
| 2002/0169381 A1* | 11/2002 | Asada ............... A61B 5/14552 600/500 |
| 2015/0220109 A1 | 8/2015 | von Badinski et al. |
| 2016/0077587 A1 | 3/2016 | Kienzle et al. |
| 2016/0206251 A1 | 7/2016 | Kwon et al. |
| 2016/0213267 A1* | 7/2016 | Laakkonen .......... A61B 5/6826 |
| 2016/0292563 A1* | 10/2016 | Park ...................... G06F 3/016 |
| 2016/0350581 A1 | 12/2016 | Manuel et al. |
| 2017/0079534 A1* | 3/2017 | Tchertkov ............. A61B 5/681 |
| 2017/0095168 A1* | 4/2017 | Kwon .................. A61B 5/1172 |
| 2017/0209095 A1 | 7/2017 | Wagner et al. |
| 2017/0235933 A1 | 8/2017 | von Badinski et al. |
| 2017/0347902 A1* | 12/2017 | Van Gool ......... A61B 5/02427 |
| 2018/0123629 A1 | 5/2018 | Wetzig |
| 2019/0013368 A1 | 1/2019 | Chung et al. |
| 2019/0025120 A1 | 1/2019 | Lee et al. |
| 2019/0033217 A1 | 1/2019 | Kim |
| 2019/0154584 A1 | 5/2019 | Ahn et al. |
| 2019/0155385 A1 | 5/2019 | Lim et al. |
| 2019/0167190 A1 | 6/2019 | Choi et al. |
| 2019/0200883 A1 | 7/2019 | Moon et al. |
| 2019/0246977 A1 | 8/2019 | Miller et al. |
| 2021/0072833 A1 | 3/2021 | Mutlu et al. |
| 2021/0089126 A1 | 3/2021 | Nickerson |
| 2021/0204815 A1 | 7/2021 | Koskela et al. |
| 2021/0289897 A1 | 9/2021 | Hsu et al. |
| 2022/0085841 A1 | 3/2022 | Gretarsson et al. |
| 2022/0091683 A1 | 3/2022 | Beyhs et al. |
| 2022/0334639 A1 | 10/2022 | Sanchez |
| 2022/0383741 A1 | 12/2022 | Sanchez |
| 2022/0386885 A1 | 12/2022 | Lee et al. |
| 2022/0407550 A1 | 12/2022 | Gretarsson et al. |
| 2022/0409072 A1 | 12/2022 | Kang et al. |
| 2023/0000405 A1 | 1/2023 | Lee et al. |
| 2023/0007884 A1 | 1/2023 | Kang et al. |
| 2023/0008487 A1 | 1/2023 | Caizzone et al. |
| 2023/0021838 A1 | 1/2023 | Tse et al. |
| 2023/0043018 A1 | 2/2023 | Wai et al. |
| 2023/0053252 A1 | 2/2023 | Jung |
| 2023/0056434 A1 | 2/2023 | Jang et al. |
| 2023/0070636 A1 | 3/2023 | Kang et al. |
| 2023/0072436 A1 | 3/2023 | Sanchez |
| 2023/0085555 A1 | 3/2023 | Nomvar et al. |
| 2023/0118067 A1 | 4/2023 | Chang et al. |
| 2023/0143293 A1 | 5/2023 | Sanchez |
| 2023/0153416 A1 | 5/2023 | Sanchez |
| 2023/0154033 A1 | 5/2023 | Oh et al. |
| 2023/0157645 A1 | 5/2023 | Lee et al. |
| 2023/0174114 A1 | 6/2023 | Sanchez |
| 2023/0190118 A1 | 6/2023 | Park et al. |
| 2023/0200744 A1 | 6/2023 | Choi et al. |
| 2023/0205170 A1 | 6/2023 | Sanchez |
| 2023/0205325 A1 | 6/2023 | Khan |
| 2023/0213970 A1 | 7/2023 | von Badinski et al. |
| 2023/0218192 A1 | 7/2023 | Eom et al. |
| 2023/0225671 A1 | 7/2023 | Kosman et al. |
| 2023/0233084 A1 | 7/2023 | Moon et al. |
| 2023/0301540 A1 | 9/2023 | Jung et al. |
| 2023/0309844 A1 | 10/2023 | Jang et al. |
| 2023/0324293 A1 | 10/2023 | Lee |
| 2023/0350492 A1 | 11/2023 | Nickerson |
| 2023/0350503 A1 | 11/2023 | D'Amone et al. |
| 2023/0359291 A1 | 11/2023 | Beyhs et al. |
| 2023/0361588 A1 | 11/2023 | Sanchez |
| 2023/0376071 A1 | 11/2023 | von Badinski et al. |
| 2023/0376072 A1 | 11/2023 | von Badinski et al. |
| 2023/0384827 A1 | 11/2023 | von Badinski et al. |
| 2023/0409080 A1 | 12/2023 | von Badinski et al. |
| 2024/0000380 A1 | 1/2024 | Fei et al. |
| 2024/0000387 A1 | 1/2024 | Realubit et al. |
| 2024/0012479 A1 | 1/2024 | Qiu et al. |
| 2024/0045473 A1 | 2/2024 | Lee et al. |
| 2024/0046505 A1 | 2/2024 | Liu et al. |
| 2024/0048675 A1 | 2/2024 | Choi et al. |
| 2024/0049350 A1 | 2/2024 | Choi et al. |
| 2024/0058686 A1 | 2/2024 | Bhandarkar et al. |
| 2024/0065631 A1 | 2/2024 | Brooks |
| 2024/0081663 A1 | 3/2024 | Park et al. |
| 2024/0112563 A1 | 4/2024 | Norman et al. |
| 2024/0115212 A1 | 4/2024 | Jang et al. |
| 2024/0125915 A1 | 4/2024 | Au et al. |
| 2024/0126328 A1 | 4/2024 | von Badinski et al. |
| 2024/0126329 A1 | 4/2024 | von Badinski et al. |
| 2024/0126330 A1 | 4/2024 | von Badinski et al. |
| 2024/0126382 A1 | 4/2024 | Yoo |
| 2024/0134417 A1 | 4/2024 | von Badinski et al. |
| 2024/0138721 A1 | 5/2024 | Eom et al. |
| 2024/0143027 A1 | 5/2024 | von Badinski et al. |
| 2024/0143028 A1 | 5/2024 | von Badinski et al. |
| 2024/0146350 A1 | 5/2024 | Gretarsson et al. |
| 2024/0168521 A1 | 5/2024 | von Badinski et al. |
| 2024/0172945 A1 | 5/2024 | Park et al. |
| 2024/0176425 A1 | 5/2024 | Wang et al. |
| 2024/0179550 A1 | 5/2024 | Au et al. |
| 2024/0187407 A1 | 6/2024 | Mars et al. |
| 2024/0188834 A1 | 6/2024 | Kwon et al. |
| 2024/0188881 A1 | 6/2024 | Bonificio et al. |
| 2024/0201736 A1 | 6/2024 | von Badinski et al. |

\* cited by examiner

NERD OF THE RINGS (SMART RING WITH SPECTROSCOPIC SENSORS)

CROSS-REFERENCE TO RELATED APPLICATIONS

This application is a continuation-in-part of U.S. patent application Ser. No. 18/617,950 filed on 2024 Mar. 27. This application is a continuation-in-part of U.S. patent application Ser. No. 18/121,841 filed on 2023 Mar. 15.

U.S. patent application Ser. No. 18/617,950 claimed the priority benefit of U.S. provisional application 63/542,077 filed on 2023 Oct. 2. U.S. patent application Ser. No. 18/617,950 was a continuation-in-part of U.S. patent application Ser. No. 18/121,841 filed on 2023 Mar. 15.

U.S. patent application Ser. No. 18/121,841 was a continuation-in-part of U.S. patent application Ser. No. 17/903,746 filed on 2022 Sep. 6. U.S. patent application Ser. No. 18/121,841 was a continuation-in-part of U.S. patent application Ser. No. 17/239,960 filed on 2021 Apr. 26. U.S. patent application Ser. No. 18/121,841 was a continuation-in-part of U.S. patent application Ser. No. 16/737,052 filed on 2020 Jan. 8.

U.S. patent application Ser. No. 17/903,746 was a continuation-in-part of U.S. patent application Ser. No. 16/568,580 filed on 2019 Sep. 12. U.S. patent application Ser. No. 17/903,746 was a continuation-in-part of U.S. patent application Ser. No. 16/737,052 filed on 2020 Jan. 8. U.S. patent application Ser. No. 17/903,746 was a continuation-in-part of U.S. patent application Ser. No. 17/239,960 filed on 2021 Apr. 26. U.S. patent application Ser. No. 17/903,746 claimed the priority benefit of U.S. provisional application 63/279,773 filed on 2021 Nov. 16.

U.S. patent application Ser. No. 17/239,960 claimed the priority benefit of U.S. provisional application 63/171,838 filed on 2021 Apr. 7. U.S. patent application Ser. No. 17/239,960 was a continuation-in-part of U.S. patent application Ser. No. 16/737,052 filed on 2020 Jan. 8.

U.S. patent application Ser. No. 16/737,052 claimed the priority benefit of U.S. provisional application 62/930,013 filed on 2019 Nov. 4. U.S. patent application Ser. No. 16/737,052 claimed the priority benefit of U.S. provisional application 62/857,942 filed on 2019 Jun. 6. U.S. patent application Ser. No. 16/737,052 claimed the priority benefit of U.S. provisional application 62/814,713 filed on 2019 Mar. 6. U.S. patent application Ser. No. 16/737,052 claimed the priority benefit of U.S. provisional application 62/814,692 filed on 2019 Mar. 6. U.S. patent application Ser. No. 16/737,052 claimed the priority benefit of U.S. provisional application 62/800,478 filed on 2019 Feb. 2. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/737,052 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/737,052 was a continuation-in-part of U.S. patent application Ser. No. 15/431,769 filed on 2017 Feb. 14. U.S. patent application Ser. No. 16/737,052 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 16/568,580 claimed the priority benefit of U.S. provisional application 62/857,942 filed on 2019 Jun. 6. U.S. patent application Ser. No. 16/568,580 claimed the priority benefit of U.S. provisional application 62/814,713 filed on 2019 Mar. 6. U.S. patent application Ser. No. 16/568,580 claimed the priority benefit of U.S. provisional application 62/814,692 filed on 2019 Mar. 6. U.S. patent application Ser. No. 16/568,580 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/568,580 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/568,580 was a continuation-in-part of U.S. patent application Ser. No. 15/431,769 filed on 2017 Feb. 14. U.S. patent application Ser. No. 16/568,580 was a continuation-in-part of U.S. patent application Ser. No. 15/418,620 filed on 2017 Jan. 27. U.S. patent application Ser. No. 16/568,580 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 15/963,061 was a continuation-in-part of U.S. patent application Ser. No. 14/992,073 filed on 2016 Jan. 11. U.S. patent application Ser. No. 15/963,061 was a continuation-in-part of U.S. patent application Ser. No. 14/550,953 filed on 2014 Nov. 22.

U.S. patent application Ser. No. 15/725,330 claimed the priority benefit of U.S. provisional application 62/549,587 filed on 2017 Aug. 24. U.S. patent application Ser. No. 15/725,330 claimed the priority benefit of U.S. provisional application 62/439,147 filed on 2016 Dec. 26. U.S. patent application Ser. No. 15/725,330 was a continuation-in-part of U.S. patent application Ser. No. 15/431,769 filed on 2017 Feb. 14. U.S. patent application Ser. No. 15/725,330 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/431,769 claimed the priority benefit of U.S. provisional application 62/439,147 filed on 2016 Dec. 26. U.S. patent application Ser. No. 15/431,769 claimed the priority benefit of U.S. provisional application 62/349,277 filed on 2016 Jun. 13. U.S. patent application Ser. No. 15/431,769 claimed the priority benefit of U.S. provisional application 62/311,462 filed on 2016 Mar. 22. U.S. patent application Ser. No. 15/431,769 was a continuation-in-part of U.S. patent application Ser. No. 15/294,746 filed on 2016 Oct. 16 which issued as U.S. Pat. No. 10,627,861 on 2020 Apr. 21. U.S. patent application Ser. No. 15/431,769 was a continuation-in-part of U.S. patent application Ser. No. 15/206,215 filed on 2016 Jul. 8. U.S. patent application Ser. No. 15/431,769 was a continuation-in-part of U.S. patent application Ser. No. 14/992,073 filed on 2016 Jan. 11. U.S. patent application Ser. No. 15/431,769 was a continuation-in-part of U.S. patent application Ser. No. 14/330,649 filed on 2014 Jul. 14.

U.S. patent application Ser. No. 15/418,620 claimed the priority benefit of U.S. provisional application 62/297,827 filed on 2016 Feb. 20. U.S. patent application Ser. No. 15/418,620 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/294,746 claimed the priority benefit of U.S. provisional application 62/349,277 filed on 2016 Jun. 13. U.S. patent application Ser. No. 15/294,746 claimed the priority benefit of U.S. provisional application 62/245,311 filed on 2015 Oct. 23. U.S. patent application Ser. No. 15/294,746 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/206,215 claimed the priority benefit of U.S. provisional application 62/349,277 filed on 2016 Jun. 13. U.S. patent application Ser. No. 15/206,215 was a continuation-in-part of U.S. patent application Ser. No. 14/951,475 filed on 2015 Nov. 24 which issued as U.S. Pat. No. 10,314,492 on 2019 Jun. 11. U.S. patent application Ser. No. 15/206,215 was a continuation-in-part of U.S. patent application Ser. No. 14/948,308 filed on 2015 Nov. 21.

U.S. patent application Ser. No. 14/992,073 was a continuation-in-part of U.S. patent application Ser. No. 14/562,719 filed on 2014 Dec. 7 which issued as U.S. Pat. No. 10,130,277 on 2018 Nov. 20. U.S. patent application Ser. No. 14/992,073 was a continuation-in-part of U.S. patent application Ser. No. 13/616,238 filed on 2012 Sep. 14.

U.S. patent application Ser. No. 14/951,475 was a continuation-in-part of U.S. patent application Ser. No. 14/071,112 filed on 2013 Nov. 4. U.S. patent application Ser. No. 14/951,475 was a continuation-in-part of U.S. patent application Ser. No. 13/901,131 filed on 2013 May 23 which issued as U.S. Pat. No. 9,536,449 on 2017 Jan. 3.

U.S. patent application Ser. No. 14/948,308 was a continuation-in-part of U.S. patent application Ser. No. 14/550,953 filed on 2014 Nov. 22. U.S. patent application Ser. No. 14/948,308 was a continuation-in-part of U.S. patent application Ser. No. 14/449,387 filed on 2014 Aug. 1. U.S. patent application Ser. No. 14/948,308 was a continuation-in-part of U.S. patent application Ser. No. 14/132,292 filed on 2013 Dec. 18 which issued as U.S. Pat. No. 9,442,100 on 2016 Sep. 13. U.S. patent application Ser. No. 14/948,308 was a continuation-in-part of U.S. patent application Ser. No. 13/901,099 filed on 2013 May 23 which issued as U.S. Pat. No. 9,254,099 on 2016 Feb. 9.

U.S. patent application Ser. No. 14/562,719 claimed the priority benefit of U.S. provisional application 61/932,517 filed on 2014 Jan. 28.

U.S. patent application Ser. No. 14/330,649 was a continuation-in-part of U.S. patent application Ser. No. 13/523,739 filed on 2012 Jun. 14 which issued as U.S. Pat. No. 9,042,596 on 2015 May 26.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to biometric wearable devices.

INTRODUCTION

Wearable devices have some advantages over mobile handheld devices (such as cellphones) and non-mobile devices (such as stationary medical equipment) for monitoring a person's biometric parameters: to diagnosis adverse health conditions; to provide an alert in case of an adverse health event; to provide a feedback and/or control loop for the operation of implanted medical devices; and to help people maintain their health and prevent illness. Due to their consistent proximity to a person's body and their easily transportable nature, wearable devices can monitor biometric parameters more broadly and consistently than handheld devices. In addition to providing biometric monitoring, wearable devices can also provide a wearer with information about their environment. For example, images from a wearable camera can be analyzed to provide information about the identity of environmental objects and data from a wearable spectroscopy sensor can be analyzed to provide information about the chemical composition of environmental objects.

Among wearable devices, smart rings in particular have potential advantages for producing information about biometric parameters and/or environmental objects. For example, a smart ring is less likely to shift, rotate, or form gaps with respect to a person's body than a smart watch. Accordingly, the circumference of a smart ring can have more uniform and consistent contact with a person's body than a smart watch. This is particularly important for biometric sensor designs comprising a circumferential array of optical sensors. Also, some people may find wearing a smart ring to be less obtrusive than wearing a smart watch, particularly during sleep. For these reasons, a smart ring with spectroscopic sensors for producing information about biometric parameters and/or environmental objects can be particularly useful.

There are some challenges in the development of smart rings. For example, they are relatively small. It can be challenging to fit complex electronics and sensors into a such a small space. Also, their small size is not great a great platform for a significant-size display screen. Further, their location (between fingers on a hand) can be a challenging one from which to record images with a camera. However, these challenges are not insurmountable and are addressed by some of the innovative smart ring designs discussed herein. On balance, smart rings are a unique form factor for wearable devices with significant potential for producing information about biometric parameters and/or environmental objects.

REVIEW OF THE RELEVANT ART

U.S. patent application No. 20150220109 (von Badinski et al., Aug. 6, 2015, "Wearable Computing Device") and U.S. Pat. No. 9,582,034 (von Badinski et al., Feb. 28, 2017, "Wearable Computing Device") disclose a finger ring comprising an interior wall, an exterior wall, a flexible circuit board, and a window that facilitates data transmission, battery recharge, and/or status indication. U.S. patent application No. 20160077587 (Kienzle et al., Mar. 17, 2016, "Smart Ring") discloses a smart ring with at least one flexion sensor which detects the distance between the sensor and a finger segment. U.S. patent application No. 20160206251 (Kwon et al., Jul. 21, 2016, "Apparatus for Detecting Bio-Information") and U.S. Pat. No. 10,349,847 (Kwon et al., Jul. 6, 2019, "Apparatus for Detecting Bio-Information") disclose an apparatus with a light-emitting diode (LED), a laser diode (LD), and an optical detector.

U.S. patent application No. 20160292563 (Park, Oct. 6, 2016, "Smart Ring") discloses systems and methods for pairing a smart ring with a primary device. U.S. patent application No. 20160350581 (Manuel et al., Dec. 1, 2016, "Smart Ring with Biometric Sensor") discloses a ring comprising a ring body and a biometric sensor. U.S. patent application No. 20170209095 (Wagner et al., Jul. 27, 2017, "Optical Physiological Sensor Modules with Reduced Signal Noise") discloses an optical sensor module with light guides which have outwardly-diverging axial directions. U.S. patent application 20170235933 (von Badinski et al., Aug. 17, 2017, "Wearable Computing Device") and U.S. Pat. No. 10,156,867 (von Badinski et al., Dec. 18, 2018, "Wearable Computing Device") disclose a method for using a finger ring to identify an authorized user by illuminating a portion of the user's skin, imaging the portion, and then generating a capillary map.

U.S. patent application No. 20180123629 (Wetzig, May 3, 2018, "Smart-Ring Methods and Systems") discloses a computerized smart ring which is embedded with electronics, software, sensors wherein the ring can be electronically connected to another computing system. U.S. patent application No. 20190013368 (Chung et al., Jan. 10, 2019, "Near-Infrared Light Organic Sensors, Embedded Organic Light Emitting Diode Panels, and Display Devices Including the Same") discloses an OLED panel which is embedded with a near-infrared organic photosensor, wherein this structure enables biometric recognition.

U.S. patent application No. 20190025120 (Lee et al., Jan. 24, 2019, "Spectrometer and Spectrum Measurement Method Utilizing Same") discloses a spectrometer with a first unit spectral filter which absorbs or reflects light in a part of a wavelength band of a light spectrum of an incident target, a second unit spectral filter which absorbs or reflects light in a wavelength band different from the part of the wavelength band, a first light detector configured to detect a first light spectrum passing through the first unit spectral filter, a second light detector configured to detect a second light spectrum passing through the second unit spectral filter, and a processing unit. U.S. patent application No. 20190033217 (Kim, Jan. 31, 2019, "Spectrum Measurement Apparatus and Spectrum Measurement Method") discloses a spectrum measurement apparatus with a plurality of light sources which emit light at different wavelengths, a light detector, and a processor.

U.S. patent application No. 20190154584 (Ahn et al., May 23, 2019, "Spectroscopy Apparatus, Spectroscopy Method, and Bio-Signal Measuring Apparatus") discloses a spectroscopy apparatus with a dispersive element which divides an incident light into a plurality of lights having different output angles. U.S. patent application No. 20190155385 (Lim et al., May 23, 2019, "Smart Ring Providing Multi-Mode Control in a Personal Area Network") discloses a smart ring which provides multi-mode control in a personal area network. U.S. patent application No. 20190167190 (Choi et al., Jun. 6, 2019, "Healthcare Apparatus and Operating Method Thereof") discloses a healthcare apparatus with a plurality of light sources which emit light of different wavelengths, a light detector, and a processor configured to obtain a blood glucose level.

U.S. patent application No. 20190200883 (Moon et al., Jul. 4, 2019, "Bio-Signal Measuring Apparatus and Operating Method Thereof") discloses a bio-signal measuring apparatus with a photodetector and an array of light sources around the photodetector. U.S. patent application 20190246977 (Miller et al., Aug. 15, 2019, "Optical Sensor for Wearable Devices") discloses methods, systems, apparatuses, and/or devices which emit light into a body, receive light from a depth below a surface of the body, and determine a physiological condition of the body. U.S. Pat. No. 10,444,834 (Vescovi, Oct. 15, 2019, "Devices, Methods, and User Interfaces for a Wearable Electronic Ring Computing Device") discloses an electronic device with a finger-ring-mounted touchscreen.

U.S. Pat. No. 10,739,820 (Wang et al., Aug. 11, 2020, "Expandable Ring Device") discloses a ring device including force sensors, ultrasonic sensors, inertial measurement units, optical sensors, touch sensors, and other components. U.S. Pat. No. 10,768,666 (von Badinski et al., Sep. 8, 2020, "Wearable Computing Device") discloses a smart ring which unlocks a client computing device, wherein the ring includes an accelerometer, a gyroscope, and/or other motion sensor. U.S. Pat. No. 10,842,429 (Kinnunen et al., Nov. 24, 2020, "Method and System for Assessing a Readiness Score of a User") discloses a method and a system for assessing a user's readiness based on their movements. U.S. U.S. Pat. No. 10,893,833 (Haverinen et al., Jan. 19, 2021, "Wearable Electronic Device and Method for Manufacturing Thereof") discloses a wearable electronic device made from non-ceramic material.

U.S. patent application No. 20210072833 (Mutlu et al., Mar. 11, 2021, "Self-Mixing Interferometry-Based Gesture Input System Including a Wearable or Handheld Device") discloses a device with one or more SMI sensors which emit beams of electromagnetic radiation, wherein each beam is emitted in a different direction. U.S. patent application No. 20210089126 (Nickerson, Mar. 25, 2021, "Smart Ring") discloses a smart ring with a capacitive touch sensor. U.S. patent application 20210204815 (Koskela et al., Jul. 8, 2021, "An Optical Sensor System of a Wearable Device, A Method for Controlling Operation of an Optical Sensor System and Corresponding Computer Program Product") discloses a wearable optical sensor system including at least two photo transmitters, a photoreceiver, receiving electronics, and a microcontroller.

U.S. patent application No. 20210289897 (Hsu et al., Sep. 23, 2021, "Smart Ring") discloses a smart ring with an antenna chip and a metal ring which functions as an antenna. U.S. Pat. No. 11,188,124 (von Badinski et al., Nov. 30, 2021, "Wearable Computing Device") discloses a smart ring with a curved housing having a U-shape interior, a motion sensor, a memory, a transceiver, a temperature sensor, and a processor. U.S. Pat. No. 11,188,160 (Liu, Nov. 30, 2021, "Wireless Controlling System Implemented with Smart Ring and Wireless Controlling Method Thereof") a wireless controlling system including a smart ring and an identification program installed in a mobile device.

U.S. Pat. No. 11,275,453 (Tham et al., Mar. 15, 2022, "Smart Ring for Manipulating Virtual Objects Displayed By a Wearable Device") discloses systems, devices, media, and methods for using a ring to manipulate a virtual object displayed by smart eyewear. U.S. patent applications 20220085841 (Gretarsson et al., Mar. 17, 2022, "Smart Ring") and 20220407550 (Gretarsson et al., Dec. 22, 2022, "Smart Ring") disclose a wearable device which detects inputs, gestures, and/or biometric parameters. U.S. patent application No. 20220091683 (Beyhs et al., Mar. 24, 2022, "Ring Input Device with Pressure-Sensitive Input") and U.S. Pat. No. 11,733,790 (Beyhs et al., Aug. 22, 2023, "Ring Input Device with Pressure-Sensitive Input") disclose a ring with a pressure-sensitive input mechanism.

U.S. patent applications 20220334639 (Sanchez, Oct. 20, 2022, "Projection System for Smart Ring Visual Output") and U.S. patent application No. 20220383741 (Sanchez, Dec. 1, 2022, "Non-Visual Outputs for a Smart Ring"), and U.S. Pat. No. 11,462,107 (Sanchez, Oct. 4, 2022, "Light Emitting Diodes and Diode Arrays for Smart Ring Visual Output"), disclose a smart ring system for displaying information concerning driving conditions. U.S. Pat. No. 11,479,258 (Sanchez, Oct. 25, 2022, "Smart Ring System for Monitoring UVB Exposure Levels and Using Machine Learning Technique to Predict High Risk Driving Behavior") discloses systems and methods determine a driver's fitness to safely operate a moving vehicle based on UVB exposure. U.S. patent application No. 20220386885 (Lee et al., Dec. 8, 2022, "Wearable Electronic Device Measuring Blood Pressure and Method for Operating The Same") discloses a wearable electronic device with a memory, a first sensor, a second sensor, and a processor.

U.S. patent application No. 20220409072 (Kang et al., Dec. 29, 2022, "Apparatus and Method for Estimating Bio-Information") discloses an apparatus to estimate biometric parameters using a pulse wave sensor with channels in an isotropic shape. U.S. Pat. No. 11,540,599 (Yokoyama et al., Jan. 3, 2023, "Watch Band with Adjustable Fit") discloses shape-memory tensioning elements which respond to a stimulus in order to adjust the fit of a watch band. U.S. patent application No. 20230000405 (Lee et al., Jan. 5, 2023, "Apparatus and Method for Estimating Bio-Information Based on Bio-Impedance") discloses an apparatus to estimate biometric parameters using an impedance sensor, including a pair of input electrodes and a pair of receiving electrodes.

U.S. patent application No. 20230007884 (Kang et al., Jan. 12, 2023, "Apparatus and Method for Estimating Bio-Information") discloses an apparatus to estimate biometric parameters which measures pulse wave signals from an object. U.S. patent application No. 20230008487 (Caizzone et al., Jan. 12, 2023, "System and Method for Smart Rings Employing Sensor Spatial Diversity") discloses a ring for photoplethysmographic sensing which uses sensor spatial diversity to enhance the quality and the reliability of measurements. U.S. patent application No. 20230021838 (Tse et al., Jan. 26, 2023, "Wearable Electronic Device") discloses a wearable electronic device with conductive areas on both inner and outer surfaces. U.S. patent application No. 20230043018 (Wai et al., Feb. 9, 2023, "Smart Ring for Use with a User Device and Wi-Fi Network") discloses a smart ring with a battery, a memory, processing circuitry, a plurality of sensors, and a plurality of antennas.

U.S. Pat. No. 11,580,300 (Tham et al., Feb. 14, 2023, "Ring Motion Capture and Message Composition System") discloses systems, devices, media, and methods for composing and sharing a message based on the motion of a ring. U.S. patent application No. 20230053252 (Jung, Feb. 16, 2023, "Electronic Device Adjusting Oxygen Saturation and Method for Controlling the Same") discloses a device with a first sensor which detects movement and a second sensor which measures oxygen saturation. U.S. patent applications 20230056434 (Jang et al., Feb. 23, 2023, "Apparatus and Method for Estimating Blood Pressure") and 20230070636 (Kang et al., Mar. 9, 2023, "Apparatus and Method for Estimating Blood Pressure") disclose an apparatus for estimating blood pressure using a pulse wave sensor.

U.S. Pat. No. 11,599,147 (von Badinski et al., Mar. 7, 2023, "Wearable Computing Device") discloses a smart ring with a curved housing having a U-shape interior, a semi-flexible PCB, a motion sensor, a memory, a transceiver, a temperature sensor, and a processor. U.S. patent application No. 20230072436 (Sanchez, Mar. 9, 2023, "Harvesting Energy for a Smart Ring Via Piezoelectric Charging") discloses a smart ring which harvests mechanical energy using piezoelectricity. U.S. patent application No. 20230085555 (Nomvar et al., Mar. 16, 2023, "A Non-Invasive Continuous Blood Glucose Monitor") discloses a non-invasive device for measuring glucose levels. U.S. patent application No. 20230118067 (Chang et al., Apr. 20, 2023, "Electronic Device and Method to Measure Bioelectrical Impedance") discloses an electronic device with a plurality of electrodes, a sensor connected to the electrodes, a memory, and a processor which obtains contact impedances through the sensor.

U.S. patent applications 20230143293 (Sanchez, May 11, 2023, "Biometric Authentication Using a Smart Ring") and U.S. patent application No. 20230153416 (Sanchez, May 18, 2023, "Proximity Authentication Using a Smart Ring") discloses systems and methods for performing biometric authentication using a smart ring. U.S. patent application No. 20230154033 (Oh et al., May 18, 2023, "Method and Device for Estimating Poses and Models of Object") discloses a method for object pose and model estimation via acquiring a global feature of an input image. U.S. patent application 20230157645 (Lee et al., May 25, 2023, "Apparatus and Method for Estimating Bio-Information") discloses an apparatus to estimate biometric parameters using a spectrometer.

U.S. Pat. No. 11,660,228 (Goff et al., May 30, 2023, "Positional Obstructive Sleep Apnea Detection System") discloses an obstructive sleep apnea detection device which uses an optical engagement surface adapted to engage a user's skin. U.S. Pat. No. 11,666,230 (Piccinini et al., Jun. 6, 2023, "Electronic Device and Method for Noninvasive, Continuous Blood Pressure Monitoring") discloses an electronic device and method for continuous noninvasive blood pressure monitoring. U.S. patent application No. 20230174114 (Sanchez, Jun. 8, 2023, "Smart Ring System for Measuring Stress Levels and Using Machine Learning Techniques to Predict High Risk Driving Behavior") discloses systems and methods determine a driver's fitness to safely operate a moving vehicle based on their stress level.

U.S. patent application No. 20230190118 (Park et al., Jun. 22, 2023, "Apparatus and Method for Estimating Blood Pressure") discloses an apparatus for estimating blood pressure which extracts a cardiac output feature, a first candidate total peripheral resistance feature, and a second candidate peripheral resistance feature. U.S. patent application No. 20230200744 (Choi et al., Jun. 29, 2023, "Apparatus and Method for Estimating Target Component") discloses an apparatus for estimating a target component via a spectrometer. U.S. patent application No. 20230205170 (Sanchez, Jun. 29, 2023, "Soft Smart Ring and Method of Manufacture") discloses a smart ring with a body made from flexible material, a first part, a second part removably connected to the first part, and at least one pair of break-away portions disposed within the body.

U.S. patent application No. 20230205325 (Khan, Jun. 29, 2023, "Wearable Apparatus and Control Method Thereof") discloses a wearable apparatus with a display, a strap, at least one sensor configured to acquire posture information, and at least one processor. U.S. patent application 20230213970 (von Badinski et al., Jul. 6, 2023, "Wearable Computing Device") discloses a smart ring with a body having an inner surface and an outer surface, wherein a cavity is formed on the inner surface of the body part and an electronic part is arranged in the cavity. U.S. patent application 20230213970 (von Badinski et al., Jul. 6, 2023, "Wearable Computing Device") discloses a smart ring with a curved housing having a U-shape interior, a semi-flexible PCB, a motion sensor, a memory, a transceiver, a temperature sensor, and a processor.

U.S. patent application No. 20230218192 (Eom et al., Jul. 13, 2023, "Wrist-Type Body Component Measuring Apparatus and Body Component Measuring Method Using the Same") discloses a wrist-worn band with: a first input electrode and a first output electrode disposed on an inside surface of the band; and a second input electrode and a second output electrode disposed on an outside surface of the band. U.S. patent application No. 20230225671 (Kosman et al., Jul. 20, 2023, "Wearable Health Apparatus for the Collection of Wellness Data and Providing Feedback Therefrom to the Wearer") discloses a ring with replaceable outer shells, as well as hardware and software that allow the user to communicate with a cell phone, cloud provider, table, personal computer or AI assistant.

U.S. patent application No. 20230233084 (Moon et al., Jul. 27, 2023, "Method and Apparatus for Correcting Error of Optical Sensor, and Apparatus for Estimating Biometric Information") discloses a method of correcting an optical sensor error by adjusting the brightness of a light source. U.S. patent application No. 20230301540 (Jung et al., Sep. 28, 2023, "Apparatus and Method of Measuring Bio Signal") discloses a method of measuring a biosignal by positioning electrodes and switching an impedance measurer. U.S. patent applications 20230309844 (Jang et al., Oct. 5, 2023, "Apparatus and Method for Estimating Blood Pressure") and 20240172945 (Park et al., 5/30/2024, "Apparatus and Method for Estimating Blood Pressure") disclose an apparatus and method for estimating blood pressure using a photoplethysmogram (PPG) sensor.

U.S. patent application No. 20230324293 (Lee, Oct. 12, 2023, "Apparatus and Method for Estimating Body Water Status") discloses an apparatus for estimating body hydration level with a near-infrared light spectrometer. U.S. Pat. No. 11,793,454 (Kinnunen et al., Oct. 24, 2023, "Method and System for Providing Feedback to User for Improving Performance Level Management Thereof") discloses a method of collecting a set of user information and determining a user's current performance. U.S. patent application No. 20230350492 (Nickerson, Nov. 2, 2023, "Smart Ring") discloses a smart ring worn which is controlled based on its position. U.S. patent application No. 20230350503 (D'Amone et al., Nov. 2, 2023, "Ring Input Devices") and U.S. Pat. No. 11,714,494 (D'Amone et al., Aug. 1, 2023, "Ring Input Devices") disclose how a head-mountable device can be operated with a ring input device worn on a finger of a user.

U.S. patent application No. 20230359291 (Beyhs et al., Nov. 9, 2023, "Ring Input Device with Variable Rotational Resistance") discloses a ring input device with variable rotational resistance mechanisms which change the rotational friction of a rotating outer band. U.S. patent application 20230361588 (Sanchez, Nov. 9, 2023, "Smart Ring Power and Charging") discloses a smart ring with a both a removable power source and an internal power source. U.S. patent application 20230376071 (von Badinski et al., Nov. 23, 2023, "Wearable Computing Device") discloses a smart ring comprising an external housing component with an outer circumferential surface and an inner circumferential surface, wherein a portion of the inner circumferential surface contacts a person's finger.

U.S. patent applications 20230376072 (von Badinski et al., Nov. 23, 2023, "Wearable Computing Device") and 20230384827 (von Badinski et al., Nov. 30, 2023, "Wearable Computing Device") disclose a smart ring with a curved housing having a U-shape interior, a curved battery, a semi-flexible PCB, a motion sensor, a memory, a transceiver, a temperature sensor, and a processor. U.S. Pat. No. 11,829,831 (Ershov et al., Nov. 28, 2023, "Electronic System with Ring Device") discloses a wearable electronic device with a coil which is formed from metal traces. U.S. patent application 20230409080 (von Badinski et al., Dec. 21, 2023, "Wearable Computing Device") discloses a smart ring with a curved housing with a substantially transparent portion, a curved battery, a semi-flexible PCB, a motion sensor, a memory, a transceiver, a temperature sensor, and a processor.

U.S. Pat. No. 11,850,069 (Mars et al., Dec. 26, 2023, "Wearable Device and Methods of Manufacturing") discloses a smart ring with a battery, a PCB, a fingerprint sensor, a temperature sensor, a memory, and a processing unit. U.S. patent application No. 20240000380 (Fei et al., Jan. 4, 2024, "Wearable Device") discloses an annular case with an energy storage unit, an information transmission unit, and an optical identification assembly. U.S. patent application No. 20240000387 (Realubit et al., Jan. 4, 2024, "Finger Wearable Health Monitoring Device") discloses a finger-worn health monitoring device comprising a circular metal shell. U.S. Pat. No. 11,864,871 (Kang et al., Jan. 9, 2024, "Wearable Device and Method of Measuring Bio-Signal") discloses an external light collector, an auxiliary light source, and a light receiver.

U.S. Pat. No. 11,868,178 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, and a processor. U.S. Pat. No. 11,868,179 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, a processor, an infrared light emitter, and a visible light emitter. U.S. patent application No. 20240012479 (Qiu et al., Jan. 11, 2024, "Ring Enabling Its Wearer to Enter Control Commands") discloses systems and methods, including a smart ring, which enable a user to control electronic devices in a local network.

U.S. Pat. No. 11,874,701 (von Badinski et al., Jan. 16, 2024, "Wearable Computing Device") discloses a smart ring with a curved housing having a U-shape interior, a battery, a semi-flexible PCB, a motion sensor, a memory, a transceiver, a temperature sensor, and a processor which identifies gestures based on data from the motion sensor. U.S. Pat. No. 11,874,702 (von Badinski et al., Jan. 16, 2024, "Wearable Computing Device") discloses a smart ring with a curved housing with a substantially transparent portion, a battery, a semi-flexible PCB, a motion sensor, a memory, a transceiver, a temperature sensor, and a processor. U.S. Pat. No. 11,895,383 (Prushinskiy et al., Feb. 6, 2024, "Electronic Device Including Optical Sensor") discloses an electronic device with a housing which is rotatably arranged and an optical sensor assembly.

U.S. patent application No. 20240045473 (Lee et al., Feb. 8, 2024, "Electronic Device and Method for Operating Electronic Device") discloses an electronic device with movable housings, at least one sensor, and one or more electromagnets. U.S. patent application No. 20240046505 (Liu et al., Feb. 8, 2024, "Electronic Device and Method with Pose Prediction") discloses an electronic device for predicting a pose and a method for operating the electronic device. U.S. patent application No. 20240048675 (Choi et al., Feb. 8, 2024, "Electronic Device and Operation Method Thereof") discloses a device with processors which obtain a rotation angle of the device and determine whether the rotation angle is greater than or equal to a reference rotation angle.

U.S. patent application No. 20240049350 (Choi et al., Feb. 8, 2024, "Electronic Apparatus and Operating Method Thereof") discloses an electronic which can receive a requests for wireless connection from a first device, identify a usage of a wireless bandwidth of the first device, and determine whether a wireless connection to the first device is possible based on a remaining wireless bandwidth of the electronic device. U.S. Pat. No. 11,902,791 (Mars et al., Feb. 13, 2024, "Reader Device with Sensor Streaming Data and Methods") discloses an access control system with a controller having an antenna interface to broadcast identifying data. U.S. patent application 20240058686 (Bhandarkar et al., Feb. 22, 2024, "Smart Wearable Device") discloses a smart ring with an electronics unit that is selectively attachable to a coupling mount.

U.S. Pat. No. 11,911,181 (Huttunen et al., Feb. 27, 2024, "Flexible Wearable Ring Device") discloses a wearable device made from flexible materials. U.S. Pat. No. 11,916,900 (Mars et al., Feb. 27, 2024, "Authorized Remote Control Device Gesture Control Methods and Apparatus") discloses a method for controlling a remote control device which includes capturing biometric data. U.S. patent application No. 20240065631 (Brooks, Feb. 29, 2024, "Pressure Adjustment for Biometric Measurement") discloses a user device with a pressure sensor to determine whether the pressure between a user's body and the device is within a proper range. U.S. Pat. No. 11,925,441 (Rantanen et al., Mar. 12, 2024, "Techniques for Determining Blood Pressure Based on Morphological Features of Pulses Preliminary Class") discloses a wearable device with one or more light emitting components, one or more photodetectors, and a controller that couples the light emitting components to the photodetectors.

U.S. patent application No. 20240081663 (Park et al., Mar. 14, 2024, "Apparatus for Estimating Bio-Information and Method of Detecting Abnormal Bio-Signal") discloses an apparatus with a photoplethysmogram (PPG) sensor. U.S. Pat. No. 11,937,905 (Singleton et al., Mar. 26, 2024, "Techniques for Leveraging Data Collected by Wearable Devices and Additional Devices") discloses a method comprising receiving physiological data from a wearable device and environmental data from an external device. U.S. Pat. No. 11,949,673 (Sanchez, Apr. 2, 2024, "Gesture Authentication Using a Smart Ring") discloses systems and methods for multi-factor authentication using a smart ring. U.S. patent application No. 20240112563 (Norman et al., Apr. 4, 2024, "Bluetooth Enabled Smart Ring") discloses a smart ring device with wireless communication with a computing device that transitions between one or more states based on user and/or device inputs.

U.S. patent application No. 20240115212 (Jang et al., Apr. 11, 2024, "Apparatus and Method for Estimating Physiological Variables") discloses an apparatus for estimating physiological variables using sensors and a neural-network-based physiological variable estimation model. U.S. patent application No. 20240125915 (Au et al., Apr. 18, 2024, "Method, Apparatus, and System for Wireless Sensing Measurement and Reporting") and U.S. patent application No. 20240179550 (Au et al., May 30, 2024, "Method, Apparatus, and System for Wireless Sensing Measurement and Reporting") disclose methods, devices, and systems for wireless sensing including transmitting a time series of at least one wireless sounding signal (WSS).

U.S. patent application No. 20240126328 (von Badinski et al., Apr. 18, 2024, "Wearable Computing Device") discloses a smart ring with a curved housing having a U-shape interior, a battery, a semi-flexible PCB, a galvanic sensor, light emitters, light receivers, a memory, a transceiver, a temperature sensor, and a processor. U.S. patent application No. 20240126329 (von Badinski et al., Apr. 18, 2024, "Wearable Computing Device") discloses a wearable ring device with a ring-shaped housing, a printed circuit board, and a sensor module with infrared light emitters, visible light emitters, and light receivers. U.S. patent application No. 20240126330 (von Badinski et al., Apr. 18, 2024, "Wearable Computing Device") discloses a wearable ring device with a ring-shaped housing comprising two metallic materials, a printed circuit board, light emitters, and light receivers.

U.S. patent application No. 20240126382 (Yoo, Apr. 18, 2024, "Wearable Device and Method for Controlling Same") discloses a method of controlling a smart ring by sensing contact from a finger on an outer surface electrode on an outer circumference of the ring. U.S. patent application 20240134417 (von Badinski et al., Apr. 25, 2024, "Wearable Computing Device") discloses a wearable ring device with a ring-shaped housing, a thermoelectric generator, a printed circuit board, light emitters, and light receivers. U.S. patent application No. 20240138721 (Eom et al., May 2, 2024, "Apparatus and Method for Estimating Concentration of Analyte Component") discloses an apparatus for estimating a component level using a plurality of light sources with different central wavelengths and at least one light detector.

U.S. patent application No. 20240143027 (von Badinski et al., May 2, 2024, "Wearable Computing Device") discloses a wearable ring device with a ring-shaped housing with one or more windows, a printed circuit board, light emitters, and light receivers. U.S. patent application No. 20240143028 (von Badinski et al., May 2, 2024, "Wearable Computing Device") discloses a wearable ring device with a ring-shaped housing, a printed circuit board, and a sensor module that includes red light emitters, infrared light emitters, and light receivers. U.S. patent application No. 20240146350 (Gretarsson et al., May 2, 2024, "Smart Ring") discloses a ring, band, or necklace with a pressure-sensitive mechanism that receives user input in the form of applied pressure.

U.S. Pat. No. 11,980,439 (Koskela et al., May 14, 2024, "Optical Sensor System of a Wearable Device, A Method for Controlling Operation of an Optical Sensor System and Corresponding Computer Program Product") discloses a system comprising at least two photo transmitters, a photo-receiver, receiving electronics, and a microcontroller. U.S. Pat. No. 11,986,313 (Kinnunen et al., May 21, 2024, "Method and System for Monitoring and Improving Sleep Pattern of User") discloses methods and systems for providing feedback to a user for adjusting their sleep pattern. U.S. patent application No. 20240168521 (von Badinski et al., May 23, 2024, "Wearable Computing Device") discloses a wearable ring device with a ring-shaped housing, one or more temperature sensors, a printed circuit board, light emitters, and light receivers.

U.S. patent application No. 20240176425 (Wang et al., May 30, 2024, "Method for Controlling Wearable Device and Wearable Device") discloses detecting an abnormal touch event on a display screen of a wearable device and enabling gesture recognition in response to the abnormal touch event. U.S. patent application No. 20240187407 (Mars et al., Jun. 6, 2024, "Methods and Apparatus for Facilitating NFC Transactions") discloses a method for controlling a remote control device with a session token in response to an authentication request. U.S. Pat. No. 12,007,727 (Leith et al., Jun. 11, 2024, "Watch Band with Fit Detection") discloses a watch band with an adjustable capacitor whose capacitance changes when the watch band configuration changes.

U.S. patent application No. 20240188834 (Kwon et al., Jun. 13, 2024, "Apparatus and Method for Measuring Blood Pressure") discloses an apparatus for estimating blood pressure using a pulse wave sensor. U.S. patent application No. 20240188881 (Bonificio et al., Jun. 13, 2024, "Wearable Ring Device and Method of Monitoring Sleep Apnea Events") discloses a finger-worn band with a pulse oximetry sensor on an inner surface of the band. U.S. Pat. No. 12,013,725 (von Badinski et al., Jun. 18, 2024, "Wearable Computing Device") discloses a wearable ring device with a ring-shaped housing, a printed circuit board, a haptic feedback module, red light emitters, infrared light emitters, and light receivers. U.S. patent application No. 20240201736 (von Badinski et al., Jun. 20, 2024, "Wearable Computing Device") discloses a wearable ring device with a ring-shaped housing, a first conductive contact component, a second conductive contact component, a printed circuit board, light emitters, and light receivers.

SUMMARY OF THE INVENTION

This invention is a smart ring with spectroscopic sensors. Changes in the spectrum of light which is emitted by the light emitters and received by the light receivers which are caused by interaction with (e.g. reflection by or transmission through) matter are analyzed to get information about the molecular composition of that matter. In an example, light emitters can direct light outward toward an environmental object, wherein analysis of changes in the spectrum of this light caused by interaction with (e.g. reflection from or transmission through) the environmental object are analyzed to get information concerning the molecular composition of the object. In an example, an environmental object can be food and the smart ring can function as part of a system for tracking and improving a person's nutritional intake.

In an example, light emitters can direct light inward toward the surface of a person's finger, wherein analysis of changes in the spectrum of this light caused by interaction with (e.g. reflection from or transmission through) finger tissue are analyzed to measure one or more biometric parameters. In an example, these biometric parameters can be body oxygenation level, heart rate, heart rate variability, blood pressure, and/or blood glucose level. In an example, the smart ring can comprise a circumferential array of optical sets and/or modules which collectively span at least two-thirds of the inner circumference of the ring, wherein each optical set and/or module includes one or more light emitters and one or more light receivers.

In an example, a smart ring can comprise only outwardly-directed spectroscopic sensors (e.g. outwardly-directed light emitters and light receivers). In an example, a smart ring can comprise only inwardly-directed spectroscopic sensors (e.g. inwardly-directed light emitters and light receivers). In an example, a smart ring can comprise both outwardly-directed and inwardly-directed spectroscopic sensors (e.g. both outwardly-directed and inwardly-directed light emitters and light receivers).

BRIEF INTRODUCTION TO THE FIGURES

FIGS. 1 and 2 show a smart ring with an outwardly-directed spectroscopic sensor (e.g. light emitter and light receiver) for analyzing the composition of an environmental object. FIG. 1 shows a close-up view of this smart ring, without showing the hand on which is it worn. FIG. 2 shows this smart ring being worn on a hand.

FIGS. 3 and 4 show a smart ring which an inwardly-directed electrical and/or electromagnetic energy sensor for measuring one or more biometric parameters. FIG. 3 shows a close-up view of this smart ring, without showing the hand on which is it worn. FIG. 4 shows this smart ring being worn on a hand.

FIGS. 5 and 6 show a smart ring with an inwardly-directed spectroscopic sensor (e.g. light emitter and light receiver) for measuring one or more biometric parameters. FIG. 5 shows a close-up view of this smart ring, without showing the hand on which is it worn. FIG. 6 shows this smart ring being worn on a hand.

DETAILED DESCRIPTION OF THE FIGURES

Figure 1:
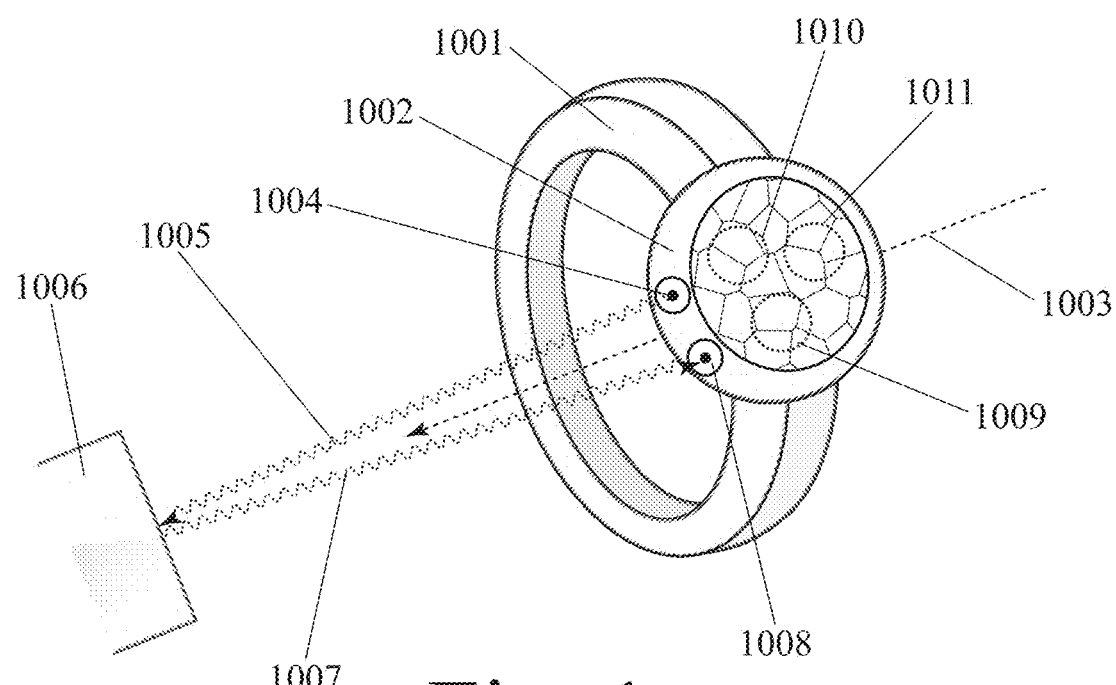

Before discussing the specific embodiments of this invention which are shown in FIGS. 1 through 8, this disclosure provides an introductory section which covers some of the general concepts, components, and methods which comprise this invention. Where relevant, these concepts, components, and methods can be applied as variations to the examples shown in FIGS. 1 through 8 which are discussed afterwards.

In an example, an electronic device worn on a person's finger (e.g. a finger ring) can have an annular shape. In an example, an electronic device worn on a person's finger (e.g. a finger ring) can be a ring with an inner perimeter which faces toward the surface of the person's finger and an outer perimeter which faces away from the surface of the person's finger, wherein the inner perimeter has a circular shape and the outer perimeter has an oval or elliptical shape.

In an example, an electronic device worn on a person's finger (e.g. a finger ring) can comprise: a dorsal half, wherein the inner (e.g. finger-facing) perimeter of the dorsal half has a semicircular shape and the outer (e.g. environment-facing) perimeter of the dorsal half has a semi-hexagonal shape; a ventral half, wherein the inner (e.g. finger-facing) perimeter of the dorsal half has a semicircular shape and the outer (e.g. environment-facing) perimeter of the dorsal half has a semicircular shape. In an example, an electronic device worn on a person's finger (e.g. a finger ring) can comprise: a dorsal half, wherein the inner (e.g. finger-facing) perimeter of the dorsal half has a semicircular shape and the outer (e.g. environment-facing) perimeter of the dorsal half has a semi-octagonal shape; a ventral half, wherein the inner (e.g. finger-facing) perimeter of the dorsal half has a semicircular shape and the outer (e.g. environment-facing) perimeter of the dorsal half has a semicircular shape.

In an example, a first portion of the circumferential perimeter of an electronic device worn on a person's finger (e.g. a finger ring) can be arcuate (e.g. partially-annular and/or section of a circle) and a second portion of the circumferential perimeter of the electronic device can be straight (e.g. flat), wherein the first portion spans between 60% and 80% of the perimeter and the second portion spans between 20% and 40% of the perimeter. In another example, an electronic device worn on a person's finger (e.g. a finger ring) can have a partially-arcuate and partially-straight circumferential perimeter. In an example, an electronic device worn on a person's finger (e.g. a finger ring) can be an annular ring with a flat-tire-shaped cross-section, wherein the flat portion spans between 30% and 50% of the circumference of the cross-section. In an example, an electronic device worn on a person's finger (e.g. a finger ring) can have a flat-tire-shaped cross-section, wherein the flat portion spans between 20% and 40% of the circumference of the cross-section.

In an example, an electronic device worn on a person's finger (e.g. a finger ring) can comprise: a dorsal half with a first width, wherein the width is measured in a plane which is tangential to the circumference of the device; and ventral half with a second width, wherein the width is measured in a plane which is tangential to the circumference of the device; wherein the ventral half is closer to the person's palm than the dorsal half; and wherein the first width is at least 25% greater than the second width. In another example, an electronic device worn on a person's finger (e.g. a finger ring) can comprise: a dorsal half with a first width, wherein the width is measured in a plane which is tangential to the circumference of the device; and ventral half with a second width, wherein the width is measured in a plane which is tangential to the circumference of the device; wherein the ventral half is closer to the person's palm than the dorsal half; and wherein the first width is between 100% and 200% greater than the second width.

In an example, an electronic device worn on a person's finger (e.g. a finger ring) can comprise: a dorsal half of an annular ring, wherein the dorsal half has a first average width, wherein width is measured in a plane which is tangential to the circumference of the device; and a ventral half of an annular ring, wherein the ventral half has a second average width, wherein width is measured in a plane which is tangential to the circumference of the device; wherein the ventral half is closer to the person's palm than the dorsal half; and wherein the first average width is at between 100% and 200% greater than the second average width.

In an example, an electronic device worn on a person's finger (e.g. a finger ring) can comprise: a rigid section of an annular ring which spans between 60% and 90% of the circumference of the device; and a flexible, elastic, compliant, and/or pleated section of the annular ring which spans between 10% and 40% of the circumference of the device (e.g. the portion of the circumference which is not spanned by the rigid section). In an example, an electronic device worn on a person's finger (e.g. a finger ring) can comprise: a partially-annular band, wherein the partially-annular band spans X % of the circumference of a person's finger, wherein X % is between 60% and 80%; and a flexible segment; wherein the flexible segment spans the remaining 100%-X % portion of the circumference of the person's finger; wherein the flexible segment is more flexible, elastic, compliant, and/or stretchable than the partially-annular band; and wherein the flexible segment connects with (e.g. is inserted into, links with, interlocks with, or interdigitates with) the partially-annular band.

In an example, an electronic device worn on a person's finger (e.g. a finger ring) can comprise: a partially-annular band which spans between 70% and 95% of the circumference of a person's finger; and a flexible transparent tube, wherein the flexible transparent tube covers a portion of the partially-annular band. In an alternative example, an electronic device worn on a person's finger (e.g. a finger ring) can comprise: a plurality of rigid sections; and a plurality of flexible sections; and a plurality of biometric sensors; wherein the biometric sensors are on the rigid sections; wherein the rigid sections are (pairwise) connected to each other by the flexible sections; wherein the flexible sections are selected from the group comprising: ball-and-socket joints, chain links, elastic connectors, hinge joints, interlocking teeth, and pleated connectors; and wherein there are electroconductive pathways (e.g. wires) in the flexible sections which provide electrical connectivity between the rigid sections.

In an example, an electronic device worn on a person's finger (e.g. a finger ring) can comprise: a first partially-annular band which spans a first portion of the circumference of a person's finger; and a second partially-annular band which spans a second portion of the circumference of the person's finger, wherein ends of the second partially-annular band are slidably-inserted into ends of the first partially-annular band. In an example, an electronic device worn on a person's finger (e.g. a finger ring) can comprise a circumferential array of rigid sections which are flexibly-connected by joints, hinges, pleated sections, and/or elastic sections, wherein there is electronic connectivity between the rigid sections through electroconductive pathways in joints, hinges, pleated sections, and/or elastic sections. In another example, an electronic device worn on a person's finger (e.g. a finger ring) can comprise a circumferential array of movably-connected (e.g. jointed and/or hinged) sections. In an example, an electronic device worn on a person's finger (e.g. a finger ring) can comprise a discontinuous annular ring which spans between 70% and 90% of the circumference of the person's finger.

In an example, an electronic device worn on a person's finger (e.g. a finger ring) can comprise: an inner annular member (e.g. ring) which is a first distance from the surface of a person's finger; and an outer annular member (e.g. ring) which is a second distance from the surface of the person's finger, wherein the second distance is greater than the first distance, wherein the outer annular member is rotated around the inner annular member, and wherein rotation of the outer annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise: an inner ring which is closer to the surface of the person's finger; an outer ring which is farther from the surface of the person's finger; a plurality of optical, spectroscopic, electrical, electromagnetic, and/or motion sensors on the inner ring which collect data that is used to analyze biometric parameters; and a plurality of optical, spectroscopic, and/or sound sensors on the outer ring which collect data that is used to analyze environmental conditions or objects. In an example, an electronic device worn on a person's finger (e.g. a finger ring) can comprise: an outer ring or layer which contains a plurality of biometric sensors; and an inner ring or layer which is transparent.

In an example, an electronic device worn on a person's finger (e.g. a finger ring) can comprise: a first annular ring; and a second annular ring; wherein the first and second annular rings are coaxial and/or concentric, and wherein the second annular ring can be moved (e.g. rotated) relative to the first annular ring to control one or more functions of the device. In an example, an electronic device worn on a person's finger (e.g. a finger ring) can comprise: a first annular ring; a second annular ring, and a third annular ring; wherein the annular rings are coaxial and/or concentric, and wherein one or more of annular rings can be moved (e.g. rotated) relative to the other annular rings to control one or more functions of the device.

In an example, an electronic device worn on a person's finger (e.g. a finger ring) can comprise: a first annular member (e.g. ring) which is worn around a person's finger; a second annular member (e.g. ring) which is worn around the person's finger; and a rotational connection between the first annular member and the second annular member, wherein the rotational connection enables the second annular member to be rotated relative to the first annular member even though they are connected, and wherein the first annular member and the second annular member are parallel to each other, wherein the first annular member and the second annular member are connected in a manner which allows the second annular member to be rotated relative to the first annular member, and wherein rotation of the second annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In another example, an electronic device worn on a person's finger (e.g. a finger ring) can comprise: a first annular ring; and a second annular ring; wherein the first and second annular rings are parallel to each other, and wherein the second annular ring can be moved (e.g. rotated) relative to the first annular ring to control one or more functions of the device. In an example, an electronic device worn on a person's finger (e.g. a finger ring) can comprise a spiral band with an adjustable inner diameter size, wherein the spiral band can be locked into a selected inner diameter size. In another example, an electronic device worn on a person's finger (e.g. a finger ring) can have a helical shape, wherein this helical shape enables the circumference of the device to be temporarily increased to facilitate sliding the device onto the finger and/or sliding the device off the finger.

In an example, an electronic device worn on a person's finger (e.g. a finger ring) can have a helical shape, wherein ends of this helical shape overlap other portions of the device, and wherein this helical shape enables the circumference of the device to be customized to (e.g. increased or decreased to match) the size of the person's finger. In an example, an electronic device worn on a person's finger (e.g. a finger ring) can have a helical shape which enables adjustment of the interior circumference of the device to match the size of the person's finger. In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion.

In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein rotating the dorsal component controls a device function selected from the group consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component further comprises a track ball (e.g. rotatable human-to-computer interface). In an example, an electronic device worn on a person's finger (e.g. a finger ring) can include a plurality of LEDs which emit light, wherein emission of different light patterns communicates different notifications, messages, and/or signals.

In an example, an electronic device worn on a person's finger (e.g. a finger ring) can include a touch screen on its dorsal side. In an alternative example, an electronic device worn on a person's finger (e.g. a finger ring) can comprise: a dorsal half of an annular ring; a ventral half of an annular ring; wherein the ventral half is closer to the person's palm than the dorsal half; and an electronic display on the dorsal half, wherein the electronic display can be rotated and/or pivoted in a plane which is tangential to the circumference of the device.

In an example, an electronic device worn on a person's finger (e.g. a finger ring) changes whether information is displayed on a dorsal side of the device or a ventral side of the device based on a finger swipe on the circumference of the device. In an example, an electronic device worn on a person's finger (e.g. a finger ring) selectively displays different types of information on different portions (e.g. different quadrants) of its circumference, wherein the device automatically changes which type of information is displayed on which portion (e.g. quadrant) based on the orientation, movement, and/or rotation of the device. In an alternative example, an electronic device worn on a person's finger (e.g. a finger ring) can project a pattern of dots or lines using via a laser, wherein this pattern acts a fiducial marker which helps in the estimation of the size, distance, and/or orientation of environmental objects (e.g. objects in images recorded by a camera on the device).

In an example, an electronic device worn on a person's finger (e.g. a finger ring) can include a micro-projector which projects images and/or text characters onto an environmental surface. In an example, an electronic device worn on a person's finger (e.g. a finger ring) can comprise: a dorsal half of an annular ring; a ventral half of an annular ring; wherein the ventral half is closer to the person's palm than the dorsal half; and an image projector on the dorsal half, wherein the image projector can be rotated and/or pivoted in a plane which is tangential to the circumference of the device.

In an example, an electronic device worn on a person's finger (e.g. a finger ring) can also include piezoelectric actuators for communicating haptic (e.g. vibrational) notifications, messages, and/or signals to the person wearing the device. In an example, an electronic device worn on a person's finger (e.g. a finger ring) can have one or more vibrating components which provide haptic communication to the person wearing the device, wherein the device communicates different notifications, messages, and/or meanings via different vibration amplitudes.

In an example, an electronic device worn on a person's finger (e.g. a finger ring) can have one or more vibrating components which provide haptic communication to the person wearing the device, wherein the device communicates different notifications, messages, and/or meanings via vibrations with different frequencies. In another example, an electronic device worn on a person's finger (e.g. a finger ring) can have one or more vibrating components which provide haptic communication to the person wearing the device, wherein the device communicates different notifications, messages, and/or meanings via different vibration patterns with different increasing or decreasing durations.

In an example, an electronic device worn on a person's finger (e.g. finger ring) can communicate different notifications, messages, and/or meanings to the person via different vibration patterns, wherein differences in vibration patterns are selected from the group consisting of: first-order differences in vibration amplitude, first-order differences in vibration duration, first-order differences in vibration frequency, first-order differences in inter-vibration intervals, second-order differences (e.g. differences in increasing or decreasing pattern) in vibration duration, second-order differences (e.g. differences in increasing or decreasing patterns) in vibration amplitude, second-order differences (e.g. differences in increasing or decreasing patterns) in inter-vibration intervals, and second-order differences (e.g. differences in increasing or decreasing patterns) in vibration frequency.

In an example, an electronic device worn on a person's finger (e.g. a finger ring) can comprise a circumferential array of pressure-activated buttons or switches. In another example, an electronic device worn on a person's finger (e.g. a finger ring) can comprise a semicircular array of touch-activated buttons or switches. In an example, an electronic device worn on a person's finger (e.g. a finger ring) can function as an in-air mouse (e.g. motion and click) interface. In an example, an electronic device worn on a person's finger (e.g. a finger ring) can be part of a system to recognize hand motions and/or gestures which further comprises one or more motion sensors in one or more finger sleeves. In an example, an electronic device worn on a person's finger (e.g. a finger ring) can include a (set of) motion sensors (e.g. accelerometer, gyroscope, and/or magnetometer) which collects body motion data which is analyzed to detect when the person is eating food, wherein detection of eating triggers a camera on the device to start recording images.

In an example, an electronic device worn on a person's finger (e.g. a finger ring) can have a finger-swipe sensor (e.g. an electromagnetic sensor capable of detecting a finger swipe) on each quadrant of the circumference of the device, wherein finger swipes on different quadrants act as different inputs for device functions. In an example, an electronic device worn on a person's finger (e.g. a finger ring) can comprise: a dorsal half of an annular ring; a ventral half of an annular ring; wherein the ventral half is closer to the person's palm than the dorsal half; and an electromagnetic energy sensor on the dorsal half. In another example, an electronic device worn on a person's finger (e.g. a finger ring) can include a plurality of electromagnetic and/or electrical energy sensors which measure biometric parameters.

In an example, an electronic device worn on a person's finger (e.g. a finger ring) can comprise: a plurality of body-facing (e.g. radially-inward) sensors; and a plurality of environment-facing (e.g. radially-outward) sensors. In an example, an electronic device worn on a person's finger (e.g. a finger ring) can comprise: a plurality of body-facing (e.g. radially-inward) biometric sensors; and an environment-facing (e.g. radially-outward) camera. In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which selectively adjust the angles between a subset of the sensors and the surface of the person's body. In another example, an electronic device worn on a person's finger (e.g. a finger ring) can include a photoplethysmography (PPG) sensor.

In an example, an electronic device worn on a person's finger (e.g. a finger ring) can include a plurality of light emitters (e.g. LEDs) which emit light in one or more of the following spectral ranges: infrared, near infrared, visible and/or white, and ultraviolet. In an alternative example, an electronic device worn on a person's finger (e.g. a finger ring) can include a plurality of light emitters (e.g. LEDs) and light receivers (e.g. photodetectors) which emit and receive light, respectively, in one or more of the following spectral ranges: infrared, near infrared, visible and/or white, and ultraviolet; wherein light emitted by the light emitters interacts with (e.g. is transmitted through and/or reflected by) body tissue before being received by the light receivers; and wherein changes in the spectral distribution of this light is analyzed to measure biometric parameters of the person.

In an example, an annular device worn on a person's finger (e.g. a finger ring) can have an array (e.g. series or sequence) of optical sensors (e.g. light emitters and receivers) around the inner circumference (body-facing surface) of the device. In an example, an electronic device worn on a person's finger (e.g. a finger ring) can have an array (e.g. series or sequence) of optical sensors (e.g. light emitters and receivers) which are pairwise-equidistant around at least three quarters of the inner circumference (body-facing surface) of the device. In an example, an electronic device worn on a person's finger (e.g. a finger ring) can have an array (e.g. series or sequence) of optical sensors (e.g. light emitters and receivers) around the inner circumference (body-facing surface) of the device.

In an example, an electronic device worn on a person's finger (e.g. a finger ring) can have an array (e.g. series or sequence) of optical sensors (e.g. light emitters and receivers) around at least three quarters of the inner circumference (body-facing surface) of the device. In an example, an electronic device worn on a person's finger (e.g. a finger ring) can have an array (e.g. series or sequence) of body-facing (e.g. radially-inward) optical sensors (e.g. light emitters and receivers) around at least three quarters of the inner circumference (body-facing surface) of the device. In an example, an electronic device worn on a person's finger (e.g. a finger ring) can have an array (e.g. series or sequence) of body-facing (e.g. radially-inward) spectroscopic sensors (e.g. light emitters and receivers to measure changes in light spectra caused by reflection from body tissue) around the inner circumference (body-facing surface) of the device which measure biometric parameters (e.g. heart rate, heart rate variability, oxygenation, blood pressure, glucose level, hydration level, skin electroconductivity, and/or stress level).

In another example, an electronic device worn on a person's finger (e.g. a finger ring) can comprise: a sequence of light emitters which are located on a first circumferential line around an inner (e.g. body-facing) surface of the device; and a sequence of light receivers which are located on a second circumferential line around a second circumferential line around the inner (body-facing) surface of the device, wherein each proximal pair of light emitters and light receivers are both on a cross-sectional line which is orthogonal to a circumferential line. In an alternative example, an electronic device worn on a person's finger (e.g. a finger ring) can comprise: a sequence of light emitters which are located on a first circumferential line around an inner (e.g. body-facing) surface of the device; a first sequence of light receivers which are located on a second circumferential line around a second circumferential line around the inner (body-facing) surface of the device; and a second sequence of light receivers which are located on a third circumferential line around a third circumferential line around the inner (body-facing) surface of the device.

In an example, an electronic device worn on a person's finger (e.g. a finger ring) can comprise: a sequence of light emitters which are located on a first circumferential line around at least three quarters of an inner (e.g. body-facing) surface of the device; a first sequence of light receivers which are located on a second circumferential line around a second circumferential line around the inner (body-facing) surface of the device; and a second sequence of light receivers which are located on a third circumferential line around a third circumferential line around the inner (body-facing) surface of the device. In another example, an electronic device worn on a person's finger (e.g. a finger ring) can comprise: a plurality of light emitters and light receivers, wherein light emitters in a first quadrant of the circumference of the device project light beams toward light receivers in a second quadrant of the device, wherein the first quadrant and the second quadrant are opposite each other.

In an example, an electronic device worn on a person's finger (e.g. a finger ring) can have a repeating (e.g. alternating) sequence of light emitters and light receivers around the inner circumference (body-facing surface) of the device, wherein the sequence is a repeating pattern of two light emitters followed by a light receiver. In an example, an electronic device worn on a person's finger (e.g. a finger ring) can have a repeating (e.g. alternating) sequence of light emitters and light receivers around the inner circumference (body-facing surface) of the device, wherein the sequence is a repeating pattern of three light receivers followed by a light emitter. In an example, an electronic device worn on a person's finger (e.g. a finger ring) can have a repeating (e.g. alternating) sequence of light emitters and light receivers around at least three quarters of the inner circumference (body-facing surface) of the device, wherein the sequence is a repeating pattern of three light emitters followed by a light receiver.

In an example, an electronic device worn on a person's finger (e.g. a finger ring) can have a repeating (e.g. alternating) sequence of light emitters and light receivers around at least three quarters of the inner circumference (body-facing surface) of the device, wherein the light emitters are located on a first ring (e.g. first circumferential line) around at least three quarters of the inner circumference (body-facing surface) of the device and light receivers are located on a second ring (e.g. second circumferential line) around at least three quarters of the inner circumference (body-facing surface) of the device. In an example, an electronic device worn on a person's finger (e.g. a finger ring) can comprise a repeating sequence of optical sensor modules (e.g. sets of light emitters and receivers) around an inner (e.g. body-facing) surface of the device, wherein each module has two light emitters and one light receiver.

In another example, an electronic device worn on a person's finger (e.g. a finger ring) can comprise a repeating sequence of optical sensor modules (e.g. sets of light emitters and receivers) around an inner (e.g. body-facing) surface of the device, wherein each module has a plurality of light emitters around a light receiver. In an example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has one light emitter and two light receivers. In another example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has a plurality of light emitters and a light receiver.

In an example, an electronic device worn on a person's finger (e.g. a finger ring) can have an array (e.g. series or sequence) of spectroscopic sensors (e.g. light emitters and receivers to measure changes in light spectra caused by transmission through body tissue) around the inner circumference (body-facing surface) of the device which measure biometric parameters (e.g. heart rate, heart rate variability, oxygenation, blood pressure, glucose level, hydration level, skin electroconductivity, and/or stress level). In an example, an electronic device worn on a person's finger (e.g. a finger ring) can comprise: a dorsal half of an annular ring; a ventral half of an annular ring; wherein the ventral half is closer to the person's palm than the dorsal half; and a spectroscopic sensor on the dorsal half, wherein the spectroscopic sensor can be rotated and/or pivoted in a plane which is tangential to the circumference of the device. In an example, an electronic device worn on a person's finger (e.g. a finger ring) can comprise: a plurality of light emitters and light receivers, wherein light emitters on a first side of the finger project light beams toward the light receivers on a second side of the finger, and wherein these light beams intersect at acute angles: the surface of the finger; and/or the body-facing surface of the device.

In an example, an electronic device worn on a person's finger (e.g. a finger ring) can comprise: one or more of body-facing (e.g. radially-inward) optical sensors; and one or more environment-facing (e.g. radially-outward) optical sensors, wherein an optical sensor includes at least one light emitter and at least one light receiver. In an example, an electronic device worn on a person's finger (e.g. a finger ring) can comprise: one or more of body-facing (e.g. radially-inward) spectroscopic sensors; and one or more environment-facing (e.g. radially-outward) spectroscopic sensors; wherein a spectroscopic sensor includes at least one light emitter and at least one light receiver, wherein body-facing light receivers receive light which has interacted with the person's body tissue in order to measure one or more biometric parameters, and wherein environment-facing light receiver light which has interacted with objects (e.g. food) in the environment in order to measure the composition of those objects.

In an example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the distances between the light receivers and the surface of the person's body. In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which adjust the distances between the sensors and the surface of the person's body.

In an example, an electronic device worn on a person's finger (e.g. a finger ring) can comprise: one or more light emitters which direct light toward a person's body; one or more light receivers which receive this light after it has passed through and/or been reflected by body tissue; one or more motion sensors; and actuators (e.g. electromagnetic, pneumatic, or hydraulic actuators) which adjust the angles between the light emitters and the surface of the person's body and/or between the light receivers and the surface of the person's body based on motion detected by the one or more motion sensors. In another example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the angles between the light emitters and the surface of the person's body.

In an example, an electronic device worn on a person's finger (e.g. a finger ring) can comprise: one or more electrical energy emitters which transmit electrical energy into a person's body; one or more electrical energy receivers which receive electrical energy from the person's body; and one or more actuators (e.g. electromagnetic, pneumatic, or hydraulic actuators), wherein the one or more actuators change the radial and/or circumferential locations of the electrical energy emitters on the device; and/or wherein the one or more actuators change the radial and/or circumferential locations of the electrical energy receivers on the device. In an example, an electronic device worn on a person's finger (e.g. a finger ring) can include light emitters and light receivers, wherein distances between the light emitters and/or the light receivers and the surface of the person's body can be adjusted.

In an example, an electronic device worn on a person's finger (e.g. a finger ring) can include an environment-facing (e.g. radially-outward) camera. In another example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein there is a camera in the dorsal component. In an example, an electronic device worn on a person's finger (e.g. a finger ring) can have an environment-facing (e.g. radially-outward) camera which can be moved (e.g. rotated on a ring or slid along an arcuate track) from a dorsal side of the device to a ventral side of the device, or vice versa. In an example, an electronic device worn on a person's finger (e.g. a finger ring) can have Near-Field Communication (NFC) capability. In an example, an electronic device worn on a person's finger (e.g. a finger ring) can also include a wireless data transmitter, wireless data receiver, and/or wireless data transceiver.

In an example, an electronic device worn on a person's finger (e.g. a finger ring) can comprise: an annular band which is worn on a person's finger; and an energy transducer (e.g. light to electrical energy transducer) on the dorsal side of the annular band. In an example, an electronic device worn on a person's finger (e.g. a finger ring) can comprise: a dorsal half of an annular ring; a ventral half of an annular ring; wherein the ventral half is closer to the person's palm than the dorsal half; and a solar cell (e.g. light-to-electricity transducer) on the dorsal half, wherein the solar cell (e.g. light-to-electricity transducer) can be rotated and/or pivoted in a plane which is tangential to the circumference of the device.

In an example, an electronic device worn on a person's finger (e.g. a finger ring) can have a circular, oval, elliptical, or egg shape. In an alternative example, an electronic device worn on a person's finger (e.g. a finger ring) can be a ring with an inner perimeter which faces toward the surface of the person's finger and an outer perimeter which faces away from the surface of the person's finger, wherein the inner perimeter has a circular shape and the outer perimeter has a limacon and/or cardioid shape. In an example, an electronic device worn on a person's finger (e.g. a finger ring) can be a ring with an inner perimeter which faces toward the surface of the person's finger and an outer perimeter which faces away from the surface of the person's finger, wherein the inner perimeter has a circular shape and the outer perimeter has a polygonal shape.

In an example, a central cross-section of an electronic device worn on a person's finger (e.g. a finger ring) can have a flat-tire shape, wherein the flat portion of the cross-section is on the dorsal half of the device. In another example, a first portion of the circumferential perimeter of an electronic device worn on a person's finger (e.g. a finger ring) can be arcuate (e.g. partially-annular and/or section of a circle) and a second portion of the circumferential perimeter of the electronic device can be straight (e.g. flat), wherein the first portion spans between 70% and 90% of the perimeter and the second portion spans between 10% and 30% of the perimeter. In an example, an electronic device worn on a person's finger (e.g. a finger ring) can be an annular ring with a flat-tire-shaped cross-section. In an example, an electronic device worn on a person's finger (e.g. a finger ring) can have a flat-tire-shaped cross-section, wherein the flat portion spans between 30% and 50% of the circumference of the cross-section. In an example, an electronic device worn on a person's finger (e.g. a finger ring) can be an annular ring with a flat-tire-shaped cross-section, wherein the flat portion of the cross-section is on the dorsal half of the device.

In an example, an electronic device worn on a person's finger (e.g. a finger ring) can comprise: a dorsal half with a first width, wherein the width is measured in a plane which is tangential to the circumference of the device; and ventral half with a second width, wherein the width is measured in a plane which is tangential to the circumference of the device; wherein the ventral half is closer to the person's palm than the dorsal half; and wherein the first width is at least 50% greater than the second width. In an example, an electronic device worn on a person's finger (e.g. a finger ring) can comprise: a dorsal half of an annular ring, wherein the dorsal half has a first average width, wherein width is measured in a plane which is tangential to the circumference of the device; and a ventral half of an annular ring, wherein the ventral half has a second average width, wherein width is measured in a plane which is tangential to the circumference of the device; wherein the ventral half is closer to the person's palm than the dorsal half; and wherein the first average width is greater than the second average width.

In an example, a portion of the circumference of an electronic device which is worn on a person's finger (e.g. a finger ring) can comprise a flexible, elastic, compliant, and/or pleated section (e.g. tube) which enables temporarily changes in the size of the inner circumference of the device. In an alternative example, an electronic device worn on a person's finger (e.g. a finger ring) can comprise: a rigid metal section of an annular ring which spans between 60% and 90% of the circumference of the device; and a flexible, elastic, compliant, and/or pleated polymer section of the annular ring which spans between 10% and 40% of the circumference of the device (e.g. the portion of the circumference which is not spanned by the rigid section).

In an example, an electronic device worn on a person's finger (e.g. a finger ring) can comprise: a partially-annular band, wherein the partially-annular band spans X % of the circumference of a person's finger, wherein X % is between 70% and 95%; and a flexible segment; wherein the flexible segment spans the remaining 100%-X % portion of the circumference of the person's finger; wherein the flexible segment is more flexible, elastic, compliant, and/or stretchable than the partially-annular band; and wherein the flexible segment connects with (e.g. is inserted into, links with, interlocks with, or interdigitates with) the partially-annular band.

In another example, an electronic device worn on a person's finger (e.g. a finger ring) can comprise: a plurality of rigid sections; and a plurality of flexible sections; wherein the rigid sections are (pairwise) connected to each other by the flexible sections, and wherein a flexible section is selected from the group comprising: ball-and-socket joint, chain link, elastic connector, hinge joint, interlocking teeth, and pleated connector. In an example, an electronic device worn on a person's finger (e.g. a finger ring) can comprise a plurality of rigid sections which are flexibly-connected by a plurality of flexible sections, wherein a flexible section is selected from the group comprising: ball-and-socket joint, chain link, elastic connector, hinge joint, interlocking teeth, and pleated connector.

In an example, an electronic device worn on a person's finger (e.g. a finger ring) can comprise: a first partially-annular band which spans a first portion of the circumference of a person's finger; and a second partially-annular band which spans a second portion of the circumference of the person's finger, wherein the second partially-annular band is connected to the first partially-annular band by movable, flexible, compliant, elastic, stretchable, and/or pleated joints. In an example, an electronic device worn on a person's finger (e.g. a finger ring) can comprise: a first partially-annular band which spans a first portion of the circumference of a person's finger; and a second partially-annular band which spans a second portion of the circumference of the person's finger, wherein ends of the second partially-annular band are connected to ends of the first partially-annular band by movable joints. In an example, an electronic device worn on a person's finger (e.g. a finger ring) can comprise a circumferential array of movably-connected (e.g. jointed and/or hinged) rigid sections. In another example, an electronic device worn on a person's finger (e.g. a finger ring) can comprise a discontinuous annular ring which spans between 70% and 90% of the circumference of the person's finger, wherein this discontinuous shape enables (temporary) adjustment of the size of the device.

In an example, an electronic device worn on a person's finger (e.g. a finger ring) can comprise: an inner annular member (e.g. ring) which is a first distance from the surface of a person's finger; and an outer annular member (e.g. ring) which is a second distance from the surface of the person's finger, wherein the second distance is greater than the first distance, wherein the inner annular member and the second annular member are nested (e.g. coaxial), wherein the outer annular member is rotated around the inner annular member, and wherein rotation of the outer annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In another example, an electronic device worn on a person's finger (e.g. a finger ring) can comprise: an outer ring, band, or layer which contains a plurality of biometric sensors; and an inner ring, band, or layer which is transparent, wherein the outer ring, band, or layer can be rotated around the inner ring, band, or layer to change the (radial) locations of the biometric sensors relative to the circumference of the person's finger. In an example, an electronic device worn on a person's finger (e.g. a finger ring) can comprise: an inner ring which is closer to the surface of the person's finger; an outer ring which is farther from the surface of the person's finger; a plurality of biometric sensors on the inner ring; and a plurality of environmental sensors on the outer ring. In an example, an electronic device worn on a person's finger (e.g. a finger ring) can comprise: a first annular ring; and a second annular ring; wherein the first and second annular rings are nested relative to each other, and wherein the second annular ring can be moved (e.g. rotated) relative to the first annular ring to control one or more functions of the device.

In an example, an electronic device worn on a person's finger (e.g. a finger ring) can comprise: a first annular member (e.g. ring) which is worn around a person's finger; and a second annular member (e.g. ring) which is worn around the person's finger, wherein the first annular member and the second annular member are parallel to each other, wherein the second annular member is rotated relative to the first annular member, and wherein rotation of the second annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise: a first annular member (e.g. ring) which is worn around a person's finger; a second annular member (e.g. ring) which is worn around the person's finger; and a ball bearing mechanism between the first annular member and the second annular member, wherein the ball bearing mechanism enables the second annular member to be rotated relative to the first annular member even though they are connected, and wherein the first annular member and the second annular member are parallel to each other, wherein the first annular member and the second annular member are connected in a manner which allows the second annular member to be rotated relative to the first annular member, and wherein rotation of the second annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise: a first annular ring; a second annular ring, and a third annular ring; wherein the annular rings are parallel to each other, and wherein one or more of annular rings can be moved (e.g. rotated) relative to the other annular rings to control one or more functions of the device. In an example, an electronic device worn on a person's finger (e.g. a finger ring) can comprise a spiral band with an adjustable inner diameter size, wherein the spiral band can be locked into a selected inner diameter size via a locking mechanism selected from the group consisting of: buckle, button, clasp, hook, hook-and-loop material, latch, magnet, pin, prong, and snap.

In an example, an electronic device worn on a person's finger (e.g. a finger ring) can have a helical shape, wherein there is circumferential overlap between the ends of the device; and wherein this helical shape enables the circumference of the device to be temporarily increased to facilitate sliding the device onto the finger and/or sliding the device off the finger. In another example, an electronic device worn on a person's finger (e.g. a finger ring) can have a helical shape, wherein ends of this helical shape overlap other portions of the device, and wherein this helical shape enables the circumference of the device to be changed by exerting radial force on the device.

In an example, an electronic device worn on a person's finger (e.g. a finger ring) can have a helical shape which enables adjustment of the interior circumference of the device to match the size of the person's finger, thereby reducing the need for precise size fitting. In an example, a portion of a smart ring can be made with gold, or other precious metal, making it precious, precious, yes, my precious, we wants it. In another example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion.

In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein rotating the dorsal component (e.g. in a plane which is tangent to the annular band) controls a device function selected from the group consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can include a plurality of LEDs which emit light, wherein light emission of light of different colors by the device communicates different notifications, messages, and/or signals. In an example, an electronic device worn on a person's finger (e.g. a finger ring) can include a plurality of LEDs which emit light, wherein light emission of light of different intensity by the device communicates different notifications, messages, and/or signals. In an example, an electronic device worn on a person's finger (e.g. a finger ring) can comprise: a dorsal half of an annular ring; a ventral half of an annular ring; wherein the ventral half is closer to the person's palm than the dorsal half; and an electronic display on the dorsal half.

In an example, an electronic device worn on a person's finger (e.g. a finger ring) can comprise: a dorsal half of an annular ring; a ventral half of an annular ring; wherein the ventral half is closer to the person's palm than the dorsal half; and a touch screen on the dorsal half, wherein the touch screen can be rotated and/or pivoted in a plane which is tangential to the circumference of the device. In an alternative example, an electronic device worn on a person's finger (e.g. a finger ring) displays information on its circumference, wherein the device automatically changes the portion (e.g. quadrant) on which information is displayed based on the orientation, movement, and/or rotation of the device. In an example, an electronic device worn on a person's finger (e.g. a finger ring) can displays different types of information on different portions (e.g. different quadrants) of its circumference, wherein the device changes which type of information is displayed on which portion (e.g. quadrant) based on a finger-swipe on the circumference of the device.

In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion, and wherein the protruding component further comprises a low-power laser pointer. In an example, an electronic device worn on a person's finger (e.g. a finger ring) can comprise: a dorsal half of an annular ring; a ventral half of an annular ring; wherein the ventral half is closer to the person's palm than the dorsal half; and an image projector on the dorsal half.

In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion, and wherein the protruding component further comprises an image projector. In an example, an electronic device worn on a person's finger (e.g. a finger ring) can have one or more vibrating components which provide haptic communication to the person wearing the device. In another example, an electronic device worn on a person's finger (e.g. a finger ring) can have one or more vibrating components which provide haptic communication to the person wearing the device, wherein the device communicates different notifications, messages, and/or meanings via different vibration durations.

In an example, an electronic device worn on a person's finger (e.g. a finger ring) can have one or more vibrating components which provide haptic communication to the person wearing the device, wherein the device communicates different notifications, messages, and/or meanings via different vibration patterns with different ascending or descending frequencies. In an alternative example, an electronic device worn on a person's finger (e.g. a finger ring) can have one or more vibrating components which provide haptic communication to the person wearing the device, wherein different patterns, sequences, and/or series of vibrations communicate different notifications, messages, and/or meanings to the person.

In an example, an electronic device worn on a person's finger (e.g. a finger ring) can have one or more human-to-computer communication interfaces through which the person can enter commands or other forms of communication to the device, wherein the one or more interfaces are selected from the group consisting of: camera; directing a low-power laser pointer; electromagnetic energy sensor; gesture recognition; motion recognition; motion sensor; muscle activation; optical sensor; pointing the device; pressing a button; pressure sensor; rotating a ring, dial, or crown; speaking to the device; tapping the device; touching or swiping a display screen; touching or swiping a portion of the circumference of the device; track ball; and voice recognition.

In an example, an electronic device worn on a person's finger (e.g. a finger ring) can comprise a circumferential array of touch-activated buttons or switches. In an example, an electronic device worn on a person's finger (e.g. a finger ring) can have a button on each quadrant of the circumference of the device, wherein pressing buttons on different quadrants act as different inputs for device functions. In an example, an electronic device worn on a person's finger (e.g. a finger ring) can be part of a system to recognize hand motions and/or gestures which further comprises one or more motion sensors which are worn on one or more finger tips. In an example, an electronic device worn on a person's finger (e.g. a finger ring) can include a (set of) motion sensors (e.g. accelerometer, gyroscope, and/or magnetometer) which collects body motion data which is analyzed to detect when the person is eating food. In an example, an electronic device worn on a person's finger (e.g. a finger ring) can include a (set of) motion sensors (e.g. accelerometer, gyroscope, and/or magnetometer) which collects body motion data which is analyzed to detect when the person is eating food, wherein detection of eating triggers a camera on eyewear to start recording images.

In an example, an electronic device worn on a person's finger (e.g. a finger ring) can comprise: a dorsal half of an annular ring; a ventral half of an annular ring; wherein the ventral half is closer to the person's palm than the dorsal half; and a microphone on the dorsal half. In an example, an electronic device worn on a person's finger (e.g. a finger ring) can comprise: a dorsal half of an annular ring; a ventral half of an annular ring; wherein the ventral half is closer to the person's palm than the dorsal half; and an electromagnetic energy sensor on the dorsal half, wherein the electromagnetic energy sensor can be rotated and/or pivoted in a plane which is tangential to the circumference of the device. In an example, an electronic device worn on a person's finger (e.g. a finger ring) can also include a thermistor or other type of temperature sensor.

In an example, an electronic device worn on a person's finger (e.g. a finger ring) can comprise: one or more body-facing (e.g. radially-inward) biometric sensors; and one or more environment-facing (e.g. radially-outward) cameras. In another example, an electronic device worn on a person's finger (e.g. a finger ring) can comprise: a plurality of body-facing (e.g. radially-inward) electrical energy sensors; and an environment-facing (e.g. radially-outward) camera. In an example, an electronic device worn on a person's finger (e.g. a finger ring) can include a plurality of optical sensors which measure biometric parameters. In another example, an electronic device worn on a person's finger (e.g. a finger ring) can comprise: a dorsal half of an annular ring; a ventral half of an annular ring; wherein the ventral half is closer to the person's palm than the dorsal half; and an optical sensor on the dorsal half, wherein the optical sensor can be rotated and/or pivoted in a plane which is tangential to the circumference of the device.

In an example, an electronic device worn on a person's finger (e.g. a finger ring) can include a plurality of light emitters (e.g. LEDs) and light receivers (e.g. photodetectors) which emit and receive light, respectively, in one or more of the following spectral ranges: infrared, near infrared, visible and/or white, and ultraviolet. In an example, an electronic device worn on a person's finger (e.g. a finger ring) can include a plurality of optical sensors (e.g. photodetectors) which detect light in one or more of the following spectral ranges: infrared, near infrared, visible and/or white, and ultraviolet.

In an example, an annular device worn on a person's finger (e.g. a finger ring) can have an array (e.g. series or sequence) of optical sensors (e.g. light emitters and receivers) around at least three quarters of the inner circumference (body-facing surface) of the device. In another example, an electronic device worn on a person's finger (e.g. a finger ring) can have an array (e.g. series or sequence) of optical sensors (e.g. light emitters and receivers) which are evenly-distributed around the inner circumference (body-facing surface) of the device. In an example, an electronic device worn on a person's finger (e.g. a finger ring) can have an array (e.g. series or sequence) of body-facing (e.g. radially-inward) optical sensors (e.g. light emitters and receivers) around the inner circumference (body-facing surface) of the device.

In an example, an electronic device worn on a person's finger (e.g. a finger ring) can have an array (e.g. series or sequence) of optical sensors (e.g. light emitters and receivers) around at least three quarters of the inner circumference (body-facing surface) of the device which collect data concerning the person's biometric parameters (e.g. heart rate, heart rate variability, oxygenation, blood pressure, glucose level, hydration level, skin electroconductivity, and/or stress level). In an example, an electronic device worn on a person's finger (e.g. a finger ring) can have an array (e.g. series or sequence) of body-facing (e.g. radially-inward) optical sensors (e.g. light emitters and receivers) around at least three quarters of the inner circumference (body-facing surface) of the device which collect data concerning biometric parameters (e.g. heart rate, heart rate variability, oxygenation, blood pressure, glucose level, hydration level, skin electroconductivity, and/or stress level).

In an example, an electronic device worn on a person's finger (e.g. a finger ring) can have an array (e.g. series or sequence) of body-facing (e.g. radially-inward) spectroscopic sensors (e.g. light emitters and receivers to measure changes in light spectra caused by transmission through body tissue) around at least three quarters of the inner circumference (body-facing surface) of the device which collect data concerning biometric parameters (e.g. heart rate, heart rate variability, oxygenation, blood pressure, glucose level, hydration level, skin electroconductivity, and/or stress level).

In an example, an electronic device worn on a person's finger (e.g. a finger ring) can comprise: a sequence of light emitters which are located on a first circumferential line around at least three quarters of an inner (e.g. body-facing) surface of the device; and a sequence of light receivers which are located on a second circumferential line around a second circumferential line around the inner (body-facing) surface of the device, wherein each proximal pair of light emitters and light receivers are both on a cross-sectional line which is orthogonal to a circumferential line.

In another example, an electronic device worn on a person's finger (e.g. a finger ring) can comprise: a first sequence of light emitters which are located on a first circumferential line around an inner (e.g. body-facing) surface of the device; a second sequence of light emitters which are located on a second circumferential line around a second circumferential line around the inner (body-facing) surface of the device; and a sequence of light receivers which are located on a third circumferential line around a third circumferential line around the inner (body-facing) surface of the device.

In an example, an electronic device worn on a person's finger (e.g. a finger ring) can comprise: a first sequence of light emitters which are located on a first circumferential line around at least three quarters of an inner (e.g. body-facing) surface of the device; a second sequence of light emitters which are located on a second circumferential line around a second circumferential line around the inner (body-facing) surface of the device; and a sequence of light receivers which are located on a third circumferential line around a third circumferential line around the inner (body-facing) surface of the device. In another example, an electronic device worn on a person's finger (e.g. a finger ring) can include light emitters and light receivers, wherein distances between the light emitters and/or the light receivers and the body-facing surface (e.g. inner circumference) of the device can be adjusted.

In an example, an electronic device worn on a person's finger (e.g. a finger ring) can have a repeating (e.g. alternating) sequence of light emitters and light receivers around the inner circumference (body-facing surface) of the device, wherein the sequence is a repeating pattern of three light emitters followed by a light receiver. In an example, an electronic device worn on a person's finger (e.g. a finger ring) can have a repeating (e.g. alternating) sequence of light emitters and light receivers around the inner circumference (body-facing surface) of the device, wherein the light emitters are located on a first ring (e.g. first circumferential line) around the inner circumference (body-facing surface) of the device and light receivers are located on a second ring (e.g. second circumferential line) around the inner circumference (body-facing surface) of the device.

In an alternative example, an electronic device worn on a person's finger (e.g. a finger ring) can have a repeating (e.g. alternating) sequence of light emitters and light receivers around at least three quarters of the inner circumference (body-facing surface) of the device, wherein the sequence is a repeating pattern of two light receivers followed by a light emitter. In an example, an electronic device worn on a person's finger (e.g. a finger ring) can comprise a repeating sequence of optical sensor modules (e.g. sets of light emitters and receivers) around an inner (e.g. body-facing) surface of the device, wherein each module has one light emitter and one light receiver.

In another example, an electronic device worn on a person's finger (e.g. a finger ring) can comprise a repeating sequence of optical sensor modules (e.g. sets of light emitters and receivers) around an inner (e.g. body-facing) surface of the device, wherein each module has a light emitter and a plurality of light receivers. In an example, an electronic device worn on a person's finger (e.g. a finger ring) can comprise a repeating sequence of optical sensor modules (e.g. sets of light emitters and receivers) around an inner (e.g. body-facing) surface of the device, wherein each module has a plurality of light emitters and a light receiver, and wherein light emitters in a module emit light at different wavelengths.

In an alternative example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has two light emitters and one light receiver. In an example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has a plurality of light emitters around a light receiver. In an example, an electronic device worn on a person's finger (e.g. a finger ring) can include an outward-facing spectroscopic sensor which is used to detect the molecular and/or nutritional composition of nearby food.

In an example, an electronic device worn on a person's finger (e.g. a finger ring) can comprise: a plurality of light emitters and light receivers, wherein the light emitters project light beams toward the finger along vectors which intersect at acute angles: the surface of the finger, the body-facing surface of the device, and/or radial lines extending out from the cross-sectional center of the finger. In an example, an electronic device worn on a person's finger (e.g. a finger ring) can comprise: one or more body-facing (e.g. radially-inward) optical sensors; and one or more environment-facing (e.g. radially-outward) cameras. In an example, an electronic device worn on a person's finger (e.g. a finger ring) can comprise: one or more of body-facing (e.g. radially-inward) spectroscopic sensors; and one or more environment-facing (e.g. radially-outward) spectroscopic sensors, wherein a spectroscopic sensor includes at least one light emitter and at least one light receiver, and wherein light is received by a light receiver after it has interacted with (e.g. been transmitted through or reflected by) matter.

In an example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the distances between the light emitters and the surface of the person's body and/or between the light receivers and the surface of the person's body. In an example, an electronic device worn on a person's finger (e.g. a finger ring) can comprise: one or more electrical energy emitters which transmit electrical energy into a person's body; one or more electrical energy receivers which receive electrical energy from the person's body; and one or more actuators (e.g. electromagnetic, pneumatic, or hydraulic actuators), wherein the one or more actuators change the distances between the electrical energy emitters and the surface of the person's body and/or wherein the one or more actuators change the distances between the electrical energy receivers and the surface of the person's body.

In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which selectively adjust the pressures between a subset of the sensors and the surface of the person's body. In another example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the angles between the light receivers and the surface of the person's body.

In an example, an electronic device worn on a person's finger (e.g. a finger ring) can include light emitters and light receivers, wherein angles between the light emitters the body-facing surface (e.g. inner circumference) of the device can be adjusted and/or wherein angles between the light receivers and the body-facing surface (e.g. inner circumference) of the device can be adjusted. In an alternative example, an electronic device worn on a person's finger (e.g. a finger ring) can comprise: one or more light emitters which direct light into a person's body; one or more light receivers which receive this light after it has interacted with (e.g. been transmitted through or reflected by) the person's body; and one or more actuators (e.g. electromagnetic, pneumatic, or hydraulic actuators), wherein the one or more actuators change the radial and/or circumferential locations of the light emitters on the device; and/or wherein the one or more actuators change the radial and/or circumferential locations of the light receivers on the device.

In an example, an electronic device worn on a person's finger (e.g. a finger ring) can include a camera whose focal direction is tangential to a circumferential perimeter of the device. In an example, an electronic device worn on a person's finger (e.g. a finger ring) can include a camera whose focal direction is radially-outward. In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion, and wherein the protruding component further comprises a camera.

In another example, an electronic device worn on a person's finger (e.g. a finger ring) can comprise: a dorsal half of an annular ring; a ventral half of an annular ring; wherein the ventral half is closer to the person's palm than the dorsal half; and a camera on the dorsal half, wherein the camera can be rotated and/or pivoted in a plane which is tangential to the circumference of the device. In an example, an electronic device worn on a person's finger (e.g. a finger ring) can have Near-Field Communication (NFC) capability which enables using the device to make in-person electronic payments.

In an example, an electronic device worn on a person's finger (e.g. finger ring) can have a modular battery which is removably-attached to the dorsal side of the device. In another example, an electronic device worn on a person's finger (e.g. a finger ring) can comprise: an annular band which is worn on a person's finger; and a solar energy cell (e.g. light to electrical energy transducer) on the dorsal side of the annular band. In an example, an electronic device worn on a person's finger (e.g. a finger ring) can be part of a system which includes an implanted medical device, wherein exchange of information between the wearable device and the implanted device creates a feedback loop which is used to manage and/or control the operation of the implanted device.

In an example, an electronic device worn on a person's finger (e.g. a finger ring) can comprise: a dorsal half, wherein the inner (e.g. finger-facing) perimeter of the dorsal half has a semicircular shape and the outer (e.g. environment-facing) perimeter of the dorsal half has a semielliptical shape; a ventral half, wherein the inner (e.g. finger-facing) perimeter of the dorsal half has a semicircular shape and the outer (e.g. environment-facing) perimeter of the dorsal half has a semicircular shape. In an example, an electronic device worn on a person's finger (e.g. a finger ring) can comprise: a dorsal half, wherein the inner (e.g. finger-facing) perimeter of the dorsal half has a semicircular shape and the outer (e.g. environment-facing) perimeter of the dorsal half has a semi-limaconal shape; a ventral half, wherein the inner (e.g. finger-facing) perimeter of the dorsal half has a semicircular shape and the outer (e.g. environment-facing) perimeter of the dorsal half has a semicircular shape.

In an example, an electronic device worn on a person's finger (e.g. a finger ring) can be a ring with an inner perimeter which faces toward the surface of the person's finger and an outer perimeter which faces away from the surface of the person's finger, wherein the inner perimeter has a circular shape and the outer perimeter has a conic-section shape other than a circle. In an example, a first portion of the circumferential perimeter of an electronic device worn on a person's finger (e.g. a finger ring) can be arcuate (e.g. partially-annular and/or section of a circle) and a second portion of the circumferential perimeter of the electronic device can be straight (e.g. flat).

In an example, an electronic device worn on a person's finger (e.g. a finger ring) can comprise: a dorsal half, wherein the inner (e.g. finger-facing) perimeter of the dorsal half has a semicircular shape and the outer (e.g. environment-facing) perimeter of the dorsal half has a polygonal shape; a ventral half, wherein the inner (e.g. finger-facing) perimeter of the dorsal half has a semicircular shape and the outer (e.g. environment-facing) perimeter of the dorsal half has a semicircular shape. In another example, an electronic device worn on a person's finger (e.g. a finger ring) can have a flat-tire-shaped cross-section.

In an example, an electronic device worn on a person's finger (e.g. a finger ring) can be an annular ring with a flat-tire-shaped cross-section, wherein the flat portion spans between 20% and 40% of the circumference of the cross-section. In an example, an electronic device worn on a person's finger (e.g. a finger ring) can have a flat-tire-shaped cross-section, wherein the flat portion of the cross-section is on the dorsal half of the device.

In an example, an electronic device worn on a person's finger (e.g. a finger ring) can comprise: a dorsal half with a first width, wherein the width is measured in a plane which is tangential to the circumference of the device; and ventral half with a second width, wherein the width is measured in a plane which is tangential to the circumference of the device; wherein the ventral half is closer to the person's palm than the dorsal half; and wherein the first width is between 50% and 100% greater than the second width. In an example, an electronic device worn on a person's finger (e.g. a finger ring) can comprise: a dorsal half of an annular ring, wherein the dorsal half has a first average width, wherein width is measured in a plane which is tangential to the circumference of the device; and a ventral half of an annular ring, wherein the ventral half has a second average width, wherein width is measured in a plane which is tangential to the circumference of the device; wherein the ventral half is closer to the person's palm than the dorsal half; and wherein the first average width is at least twice the second average width.

In an example, a portion of the circumference of an electronic device which is worn on a person's finger (e.g. a finger ring) can comprise a flexible, elastic, compliant, and/or pleated section (e.g. tube) which enables temporarily changes in the size of the inner circumference of the device, wherein this section spans between 5% and 20% of the circumference of the device. In an example, an electronic device worn on a person's finger (e.g. a finger ring) can comprise: a partially-annular band, wherein the partially-annular band spans X % of the circumference of a person's finger; and a flexible segment; wherein the flexible segment spans the remaining 100%-X % portion of the circumference of the person's finger; wherein the flexible segment is more flexible, elastic, compliant, and/or stretchable than the partially-annular band; and wherein the flexible segment connects with (e.g. is inserted into, links with, interlocks with, or interdigitates with) the partially-annular band.

In an example, an electronic device worn on a person's finger (e.g. a finger ring) can comprise: a partially-annular band which spans between 70% and 95% of the circumference of a person's finger; and an flexible tubular mesh or layer, wherein the flexible tubular mesh or layer covers a portion of the partially-annular band and spans the remaining circumference of the person's finger. In another example, an electronic device worn on a person's finger (e.g. a finger ring) can comprise: a plurality of rigid sections; and a plurality of flexible sections; wherein the rigid sections are (pairwise) connected to each other by the flexible sections; wherein a flexible section is selected from the group comprising: ball-and-socket joint, chain link, elastic connector, hinge joint, interlocking teeth, and pleated connector; and wherein there are electroconductive pathways (e.g. wires) in the flexible sections which provide electrical connectivity between the rigid sections.

In an example, an electronic device worn on a person's finger (e.g. a finger ring) can comprise: a first partially-annular band which spans a first portion of the circumference of a person's finger; and a second partially-annular band which spans a second portion of the circumference of the person's finger, wherein ends of the second partially-annular band are inserted into ends of the first partially-annular band. In an example, an electronic device worn on a person's finger (e.g. a finger ring) can comprise: a first partially-annular band which spans a first portion of the circumference of a person's finger; and a second partially-annular band which spans a second portion of the circumference of the person's finger, wherein the second partially-annular band is more flexible, compliant, elastic, and/or stretchable than the first partially-annular band.

In another example, an electronic device worn on a person's finger (e.g. a finger ring) can comprise a circumferential array of movably-connected (e.g. jointed and/or hinged) rigid sections, wherein each section further comprises one or more biometric sensors. In an example, an electronic device worn on a person's finger (e.g. a finger ring) can comprise a circumferential array of movably-connected (e.g. jointed and/or hinged) rigid sections, wherein each section further comprises one or more biometric sensors, and wherein there is electronic connectivity between the sections through electroconductive pathways in the joints or hinges. In an example, an electronic device worn on a person's finger (e.g. a finger ring) can comprise a discontinuous annular ring which spans between 70% and 90% of the circumference of the person's finger, wherein this discontinuous shape enables (temporary) adjustment of the size of the device to facilitate sliding the device onto the finger and/or slide the device off the finger.

In an example, an electronic device worn on a person's finger (e.g. a finger ring) can comprise: an outer ring, band, or layer which contains a plurality of biometric sensors; and an inner ring, band, or layer which is transparent, wherein the outer ring, band, or layer is automatically rotated around the inner ring, band, or layer when the device is unintentionally rotated (e.g. based on data from a motion sensor) in order to keep the biometric sensors on the same locations around the circumference of the person's finger. In an example, an electronic device worn on a person's finger (e.g. a finger ring) can comprise: an inner ring (e.g. closer to the surface of a person's finger); an outer ring (e.g. farther from the surface of a person's finger), wherein the outer ring further comprise a first outer ring portion which can be rotated relative to the inner ring, and wherein the outer ring further comprise a second outer ring portion which can be rotated relative to the inner ring; a first sensor which measures rotation of the first outer ring portion; and a second sensor which measures rotation of the second outer ring portion.

In an example, an electronic device worn on a person's finger (e.g. a finger ring) can comprise two coaxial and/or concentric annular rings, wherein one of the annular rings is rotated relative to the other ring. In an alternative example, an electronic device worn on a person's finger (e.g. a finger ring) can comprise: a first annular ring; a second annular ring, and a third annular ring; wherein the annular rings are nested relative to each other, and wherein one or more of annular rings can be moved (e.g. rotated) relative to the other annular rings to control one or more functions of the device.

In an example, an electronic device worn on a person's finger (e.g. a finger ring) can comprise: a first annular member (e.g. ring) which is worn around a person's finger; and a second annular member (e.g. ring) which is worn around the person's finger, wherein the first annular member and the second annular member are parallel to each other, wherein the first annular member and the second annular member are connected in a manner which allows the second annular member to be rotated relative to the first annular member, and wherein rotation of the second annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise: a first annular member (e.g. ring) which is worn around a person's finger; a second annular member (e.g. ring) which is worn around the person's finger; and a third annular member (e.g. ring) which is worn around the person's finger, wherein the first, second, and third annular members are parallel to each other, wherein the second annular member is between the first annular member and the third annular member, wherein the second annular member is rotated relative to the first and third annular members, and wherein rotation of the second annular member controls a device function selected from the group consisting of: consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can comprise a spiral band with an adjustable inner diameter. In another example, an electronic device worn on a person's finger (e.g. a finger ring) can comprise a helical band with an adjustable inner (e.g. coil) diameter. In an example, an electronic device worn on a person's finger (e.g. a finger ring) can have a helical shape, wherein the ends of the device overlap other portions of the device around the circumference of the device.

In an example, an electronic device worn on a person's finger (e.g. a finger ring) can have a helical shape which makes it easier to slide the device onto the person's finger and/or slide the device off the person's finger. In an example, an electronic device worn on a person's finger (e.g. a finger ring) can have a helical shape which enables adjustment of the interior circumference of the device to better accommodate changes in the size of the person's finger due to weight loss or gain. In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band.

In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein touching, pressing, and/or tapping the dorsal component controls a device function selected from the group consisting of: activation or change in focal direction of a camera on the device, activation or change in focal direction of a spectroscopic sensor on the device, change in the level and/or criteria for notifications conveyed to the person wearing the device, change in the level of power used by the device, change in the luminosity of a visual display on the device, change in the luminosity of an image projected by the device onto an external surface, change in the mode of computer-to-human communication interface (e.g. change between visual, auditory, and haptic communication) involving the device, change in the mode of human-to-computer communication interface (e.g. change between touch-based, voice command, and motion-based communication) involving the device, change in the volume of sound emitted from the device, change in the level of vibration created by the device, change in which biometric parameter is measured and/or displayed by the device, change in which other device is (or devices are) wirelessly-linked to the device, selecting a character or digit in a computer-based interaction, conveying the person's response to a notification, message, or call, and movement of a cursor on a different device.

In an example, an electronic device worn on a person's finger (e.g. a finger ring) can include a plurality of LEDs which emit light, wherein emission of light pulses of different durations by the device communicates different notifications, messages, and/or signals. In an example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion, and wherein the protruding component further comprises a display screen. In an alternative example, an electronic device worn on a person's finger (e.g. a finger ring) can comprise: a dorsal half of an annular ring; a ventral half of an annular ring; wherein the ventral half is closer to the person's palm than the dorsal half; and a touch screen on the dorsal half.

In an example, an electronic device worn on a person's finger (e.g. a finger ring) automatically changes whether information is displayed on a dorsal side of the device or a ventral side of the device based on the orientation, movement, and/or rotation of the device. In an example, an electronic device worn on a person's finger (e.g. a finger ring) displays information on its circumference, wherein the device changes the portion (e.g. quadrant) on which information is displayed based on a finger swipe on the circumference of the device. In another example, an electronic device worn on a person's finger (e.g. a finger ring) can include a laser pointer which acts a fiducial marker which helps in the estimation of the size, distance, and/or orientation of environmental objects (e.g. objects in images recorded by a camera on the device).

In an example, an electronic device worn on a person's finger (e.g. a finger ring) can include a microscale projector which projects images onto an environmental surface. In an example, an electronic device worn on a person's finger (e.g. a finger ring) can comprise: a microprojector which projects an image of a keyboard onto an environmental surface; and a camera and/or infrared sensor which tracks the person's finger motions (e.g. virtual key touching) relative to the image of the keyboard. In another example, an electronic device worn on a person's finger (e.g. a finger ring) can comprise: an annular portion which is worn around a person's finger; and a radially-outward protruding component (e.g. where a gemstone would go on a conventional ring) on the dorsal side of the annular portion, wherein the protruding component rotates and/or pivots in a plane which is tangential to the circumference of the annular portion, and wherein the protruding component further comprises a projector which projects images on environmental surfaces.

In an example, an electronic device worn on a person's finger (e.g. a finger ring) can have one or more vibrating components which provide haptic communication to the person wearing the device, wherein the device communicates information via vibration patterns and/or sequences with different vibration durations and/or inter-vibration intervals (e.g. via Morse code). In an example, an electronic device worn on a person's finger (e.g. a finger ring) can have one or more vibrating components which provide haptic communication to the person wearing the device, wherein the device communicates different notifications, messages, and/or meanings via different length pauses between vibrations.

In an example, an electronic device worn on a person's finger (e.g. a finger ring) can have one or more vibrating components which provide haptic communication to the person wearing the device, wherein the device communicates different notifications, messages, and/or meanings via different vibration patterns with different increasing or decreasing amplitudes. In an example, an electronic device worn on a person's finger (e.g. a finger ring) can have one or more vibrating components which provide haptic communication to the person wearing the device, wherein different vibration durations and/or different lengths of inter-vibration pauses communicate different notifications, messages, and/or meanings to the person.

In an example, an electronic device worn on a person's finger (e.g. a finger ring) can comprise: a dorsal half of an annular ring; a ventral half of an annular ring; wherein the ventral half is closer to the person's palm than the dorsal half; and a pressure-activated button on the dorsal half. In an example, an electronic device worn on a person's finger (e.g. a finger ring) can comprise a semicircular array of pressure-activated buttons or switches.

In an example, an electronic device worn on a person's finger (e.g. a finger ring) can function as a motion-based human-to-computer interface (e.g. recognizing hand motions and gestures) in an augmented reality or virtual reality environment. In another example, an electronic device worn on a person's finger (e.g. a finger ring) can be part of a system to recognize hand motions and/or gestures which further comprises one or more motion sensors which are attached to one or more of the person's finger nails. In an example, an electronic device worn on a person's finger (e.g. a finger ring) can include a (set of) motion sensors (e.g. accelerometer, gyroscope, and/or magnetometer) which collects body motion data which is analyzed to detect when the person is eating food, wherein detection of eating triggers a glucose sensor on the device to start recording body glucose levels.

In an example, an electronic device worn on a person's finger (e.g. a finger ring) can have finger-swipe sensors (e.g. electromagnetic sensors capable of detecting finger swipes) on different portions of the circumference of the device, wherein finger swipes on different portions act as different inputs for device functions. In an alternative example, an electronic device worn on a person's finger (e.g. a finger ring) can comprise a plurality of sensors which collect information concerning the person's biometric parameters selected from the group consisting of: blood pressure, body hydration level, caloric expenditure, heart rate, heart rate variability, EMG patterns and/or muscle contractions, oxygenation, skin electroconductivity, skin impedance or resistance, sleep duration, sleep quality, stress level, blood glucose level, and hand-to-mouth motions. In an example, an electronic device worn on a person's finger (e.g. a finger ring) can include one or more EMG (e.g. electromyographic) sensors which record neuromuscular signals which are used to detect finger bending and/or identify hand gestures. In an example, controlling a smart ring by making various hand gestures while taking public transportation will surely qualify you as the nerd of the rings.

In an example, an electronic device worn on a person's finger (e.g. a finger ring) can comprise: an annular member (e.g. ring) which is worn on a person's finger; and a tubular bend and/or strain sensor which is worn around the person's finger, wherein the tubular bend and/or strain sensor is closer to the tip of the finger than the annular member, and wherein the tubular bend and/or strain sensor is connected to the annular member. In another example, an electronic device worn on a person's finger (e.g. a finger ring) can comprise: one or more body-facing (e.g. radially-inward) electrical energy sensors; and one or more environment-facing (e.g. radially-outward) cameras.

In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which adjust the angles between the sensors and the surface of the person's body. In an example, an electronic device worn on a person's finger (e.g. a finger ring) can comprise: a dorsal half of an annular ring; a ventral half of an annular ring; wherein the ventral half is closer to the person's palm than the dorsal half; and an optical sensor on the dorsal half.

In an example, an electronic device worn on a person's finger (e.g. a finger ring) can comprise: a dorsal half of an annular ring; a ventral half of an annular ring; wherein the ventral half is closer to the person's palm than the dorsal half; and an infrared-based distance finder on the dorsal half. In an example, an electronic device worn on a person's finger (e.g. a finger ring) can include a plurality of light emitters (e.g. LEDs) and light receivers (e.g. photodetectors) which emit and receive light, respectively, in one or more of the following spectral ranges: infrared, near infrared, visible and/or white, and ultraviolet; wherein light emitted by the light emitters interacts with (e.g. is transmitted through and/or reflected by) body tissue before being received by the light receivers. In an example, an electronic device worn on a person's finger (e.g. a finger ring) can comprise: a dorsal half of an annular ring; a ventral half of an annular ring; wherein the ventral half is closer to the person's palm than the dorsal half; and an infrared-based distance finder on the dorsal half, wherein the infrared-based distance finder can be rotated and/or pivoted in a plane which is tangential to the circumference of the device.

In an example, an electronic device worn on a person's finger (e.g. a finger ring) can have an array (e.g. series or sequence) of optical sensors (e.g. light emitters and receivers) which are pairwise-equidistant around the inner circumference (body-facing surface) of the device. In an alternative example, an electronic device worn on a person's finger (e.g. a finger ring) can have an array (e.g. series or sequence) of optical sensors (e.g. light emitters and receivers) which are evenly-distributed around at least three quarters of the inner circumference (body-facing surface) of the device.

In an example, an electronic device worn on a person's finger (e.g. a finger ring) can have an array (e.g. series or sequence) of body-facing (e.g. radially-inward) optical sensors (e.g. light emitters and receivers) around the inner circumference (body-facing surface) of the device which collect data concerning biometric parameters (e.g. heart rate, heart rate variability, oxygenation, blood pressure, glucose level, hydration level, skin electroconductivity, and/or stress level). In another example, an electronic device worn on a person's finger (e.g. a finger ring) can have an array (e.g. series or sequence) of spectroscopic optical sensors (e.g. light emitters and receivers) around at least three quarters of the inner circumference (body-facing surface) of the device which collect data concerning biometric parameters (e.g. heart rate, heart rate variability, oxygenation, blood pressure, glucose level, hydration level, skin electroconductivity, and/or stress level).

In an example, an electronic device worn on a person's finger (e.g. a finger ring) can have an array (e.g. series or sequence) of body-facing (e.g. radially-inward) spectroscopic sensors (e.g. light emitters and receivers to measure changes in light spectra caused by transmission through body tissue) around the inner circumference (body-facing surface) of the device which measure biometric parameters (e.g. heart rate, heart rate variability, oxygenation, blood pressure, glucose level, hydration level, skin electroconductivity, and/or stress level).

In an example, an electronic device worn on a person's finger (e.g. a finger ring) can have an array (e.g. series or sequence) of body-facing (e.g. radially-inward) spectroscopic sensors (e.g. light emitters and receivers to measure changes in light spectra caused by reflection from body tissue) around at least three quarters of the inner circumference (body-facing surface) of the device which collect data concerning biometric parameters (e.g. heart rate, heart rate variability, oxygenation, blood pressure, glucose level, hydration level, skin electroconductivity, and/or stress level). In an example, an electronic device worn on a person's finger (e.g. a finger ring) can comprise: a sequence of light emitters which are located on a first circumferential line around an inner (e.g. body-facing) surface of the device; and a sequence of light receivers which are located on a second circumferential line around a second circumferential line around the inner (body-facing) surface of the device.

In an example, an electronic device worn on a person's finger (e.g. a finger ring) can comprise: a sequence of light emitters which are located on a first circumferential line around at least three quarters of an inner (e.g. body-facing) surface of the device; and a sequence of light receivers which are located on a second circumferential line around a second circumferential line around the inner (body-facing) surface of the device. In an example, an electronic device worn on a person's finger (e.g. a finger ring) can comprise: a plurality of light emitters and light receivers, wherein light emitters in a first quadrant of the circumference of the device project light beams toward light receivers in a second quadrant of the device, wherein the first quadrant and the second quadrant are adjacent to each other.

In another example, an electronic device worn on a person's finger (e.g. a finger ring) can have an array (e.g. series or sequence) of optical sensors (e.g. light emitters and receivers) around the inner circumference (body-facing surface) of the device which collect data concerning the person's biometric parameters (e.g. heart rate, heart rate variability, oxygenation, blood pressure, glucose level, hydration level, skin electroconductivity, and/or stress level).

In an example, an electronic device worn on a person's finger (e.g. a finger ring) can have a repeating (e.g. alternating) sequence of light emitters and light receivers around the inner circumference (body-facing surface) of the device, wherein the sequence is a repeating pattern of two light receivers followed by a light emitter. In an example, an electronic device worn on a person's finger (e.g. a finger ring) can have a repeating (e.g. alternating) sequence of light emitters and light receivers around at least three quarters of the inner circumference (body-facing surface) of the device, wherein the sequence is a repeating pattern of two light emitters followed by a light receiver.

In another example, an electronic device worn on a person's finger (e.g. a finger ring) can have a repeating (e.g. alternating) sequence of light emitters and light receivers around at least three quarters of the inner circumference (body-facing surface) of the device, wherein the sequence is a repeating pattern of three light receivers followed by a light emitter. In an example, an electronic device worn on a person's finger (e.g. a finger ring) can comprise a repeating sequence of optical sensor modules (e.g. sets of light emitters and receivers) around an inner (e.g. body-facing) surface of the device, wherein each module has one light emitter and two light receivers. In an example, an electronic device worn on a person's finger (e.g. a finger ring) can comprise a repeating sequence of optical sensor modules (e.g. sets of light emitters and receivers) around an inner (e.g. body-facing) surface of the device, wherein each module has a plurality of light emitters and a light receiver.

In an example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has one light emitter and one light receiver. In an example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has a light emitter and a plurality of light receivers.

In another example, an electronic device worn on a person's finger (e.g. a finger ring) can comprise a repeating sequence of optical sensor modules (e.g. sets of light emitters and receivers) around at least three quarters of an inner (e.g. body-facing) surface of the device, wherein each module has a plurality of light emitters and a light receiver, and wherein light emitters in a module emit light at different wavelengths. In an example, an electronic device worn on a person's finger (e.g. a finger ring) can comprise: a dorsal half of an annular ring; a ventral half of an annular ring; wherein the ventral half is closer to the person's palm than the dorsal half; and a spectroscopic sensor on the dorsal half.

In an example, an electronic device worn on a person's finger (e.g. a finger ring) can comprise: a plurality of light emitters and light receivers, wherein the light emitters project light beams toward the finger along vectors which are: not perpendicular to the surface of the finger, not perpendicular to the body-facing surface of the device, and not parallel with radial lines extending out from the cross-sectional center of the finger. In an alternative example, an electronic device worn on a person's finger (e.g. a finger ring) can comprise: a plurality of body-facing (e.g. radially-inward) optical sensors; and an environment-facing (e.g. radially-outward) camera.

In an example, an electronic device worn on a person's finger (e.g. a finger ring) can comprise: one or more of body-facing (e.g. radially-inward) spectroscopic sensors; and one or more environment-facing (e.g. radially-outward) spectroscopic sensors, wherein a spectroscopic sensor includes at least one light emitter and at least one light receiver, wherein light is received by a light receiver after it has interacted with (e.g. been transmitted through or reflected by) matter, wherein light received by body-facing light receivers has interacted with the person's body tissue, and wherein light received by environment-facing light receivers has interacted with food or other objects in the environment. In an example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the distances between the light emitters and the surface of the person's body.

In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which adjust the pressures between the sensors and the surface of the person's body. In an example, an electronic device worn on a person's finger (e.g. a finger ring) can comprise: a plurality of body-facing (e.g. radially-inward) sensors (e.g. electromagnetic sensors or optical sensors) around the inner surface (e.g. inner circumference) of the device; and a plurality of actuators (e.g. electromagnetic, pneumatic, or hydraulic actuators) which selectively adjust the distances between a subset of the sensors and the surface of the person's body.

In an example, an electronic device worn on a person's finger (e.g. a finger ring) can comprise: light emitters which direct light toward a person's body; light receivers which receive this light after it has passed through and/or been reflected by body tissue; and actuators (e.g. electromagnetic, pneumatic, or hydraulic actuators) which change the angles between the light emitters and the surface of the person's body and/or between the light receivers and the surface of the person's body. In another example, an electronic device worn on a person's finger (e.g. a finger ring) can include light emitters and light receivers, wherein angles between the light emitters and the surface of the person's body can be adjusted and/or wherein angles between the light receivers and the surface of the person's body can be adjusted. In an example, an electronic device worn on a person's finger (e.g. a finger ring) can include light emitters and light receivers, wherein distances between the light emitters and/or the light receivers and the body-facing surface (e.g. inner circumference) of the device can be adjusted to customize the fit of the device to the size of the person's finger.

In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein there is a camera in the dorsal component, and wherein the focal direction of the camera is tangential to the circumference of the annular band. In another example, an electronic device worn on a person's finger (e.g. a finger ring) can comprise: a dorsal half of an annular ring; a ventral half of an annular ring; wherein the ventral half is closer to the person's palm than the dorsal half; and a camera on the dorsal half.

In an example, an electronic device worn on a person's finger (e.g. a finger ring) can have a camera which can be moved (e.g. rotated on a ring or slid along an arcuate track) from a dorsal side of the device to a ventral side of the device, or vice versa. In an example, an electronic device worn on a person's finger (e.g. a finger ring) can comprise: an annular band which is worn around a person's finger; and a dorsal component (e.g. gem-like piece, dome, crown, or display screen) which protrudes radially-outward from the dorsal side of the annular band, wherein there is a camera in the dorsal component, wherein the focal direction of the camera is tangential to the circumference of the annular band, and wherein the focal direction of the camera is changed by rotation of the dorsal component.

In an example, an electronic device worn on a person's finger (e.g. a finger ring) can also include a data processor, microcontroller, and/or computing unit. In an example, an electronic device worn on a person's finger (e.g. a finger ring) can also include an energy transducer which converts light energy, thermal energy, or kinetic energy into electrical energy. In an example, an electronic device worn on a person's finger (e.g. a finger ring) can comprise: a dorsal half of an annular ring; a ventral half of an annular ring; wherein the ventral half is closer to the person's palm than the dorsal half; and a solar cell (e.g. light-to-electricity transducer) on the dorsal half. In an example, an electronic device worn on a person's finger (e.g. a finger ring) can be part of a system which includes augmented reality (AR) eyewear, wherein the wearable device serves a human-to-computer motion recognition function in augmented reality applications.

In an example, a wearable device can be designed like a piece of jewelry. In an example, a smart ring can be designed like piece of jewelry. In an example, a smart ring can be designed to look like a conventional finger ring with a gemstone. In an example, a wearable device can comprise an imaging member (e.g. camera) worn on a person's finger (e.g. in a smart ring). In an example, a smart ring can include a camera. In an example, a smart ring can include a camera on its dorsal side.

In an example, a wearable device can have one or more sensors which are selected from the group consisting of: accelerometer, inclinometer, other motion sensor, sound sensor, smell or olfactory sensor, blood pressure sensor, heart rate sensor, ECG sensor, EMG sensor, electrical sensor, chemical sensor, gastric activity sensor, camera, optical sensor, piezoelectric sensor, respiration sensor, strain gauge, electrogoniometer, temperature sensor, and pressure sensor. In an example, a smart ring can have one or more sensors which are selected from the group consisting of: accelerometer, inclinometer, other motion sensor, sound sensor, smell or olfactory sensor, blood pressure sensor, heart rate sensor, ECG sensor, EMG sensor, electrical sensor, chemical sensor, gastric activity sensor, camera, optical sensor, piezoelectric sensor, respiration sensor, strain gauge, electrogoniometer, temperature sensor, and pressure sensor.

In an example, a wearable device (e.g. smart ring) can measure the speed, pace, or rate at which a person brings food up to their mouth and provide feedback to the person to encourage them to eat slower if the speed, pace, or rate is high. In an example, this feedback can be sound-based, such as a tone or computer-generated voice. In an example, a smart ring can include a motion sensor which tracks how fast a person is eating and provide feedback if the person is eating too fast. In an example, this feedback can be auditory feedback, such as a tone or a computer-generated voice.

In an example, a wearable device (e.g. smart ring) can have optical sensors which emit and/or detect white light (e.g. visible light) and infrared (or near-infrared) light. In an example, a smart ring can have light emitters and light receivers which emit and receive, respectively, visible light and infrared light. In an example, a smart ring can have light emitters and light receivers which emit and receive, respectively, visible light and near-infrared light. In an example, a smart ring can have a first set of light emitters which emit visible light and a second set of light emitters which emit infrared light. In an example, a smart ring can have a first set of light emitters which emit visible light and a second set of light emitters which emit near-infrared light.

In an example, a wearable device can comprise: a housing that is worn around a person's finger; a spectroscopy sensor on the housing that collects data concerning light energy reflected from the person's body and/or absorbed by the person's body; a data processing unit in the housing; and a power source in the housing. In an example, a smart ring can comprise: an annular housing that is worn on a person's finger; a spectroscopy sensor in the housing that collects data concerning light energy reflected from and/or absorbed by the person's body; a data processing unit in the housing; and a power source on the housing. In an example, a smart ring can comprise: an annular housing that is worn around a person's finger; one or more spectroscopy sensors (e.g. light emitters and light receivers) in the housing which emit light toward the person's finger and receive the light after it has interacted with (e.g. been transmitted through and/or reflected by) body tissue; a data processor unit in the housing; and a power source in the housing.

In an example, a wearable device (e.g. smart ring) can include one or more spectroscopic (e.g. spectral measurement) sensors which are selected from the group consisting of: white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer. In an example, a smart ring can include a white light spectroscopy sensor, an infrared spectroscopy sensor, and/or a near-infrared spectroscopy sensor.

In an example, a wearable device can include one or more optical sensors selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart finger ring can include one or more optical sensors selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a wearable device can include one or more sensors selected from the group consisting of: accelerometer, inclinometer, motion sensor, pedometer, sound sensor, smell sensor, blood pressure sensor, heart rate sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, temperature sensor, and pressure sensor. In an example, a smart finger ring can include one or more sensors selected from the group consisting of: accelerometer, inclinometer, motion sensor, pedometer, sound sensor, smell sensor, blood pressure sensor, heart rate sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, temperature sensor, and pressure sensor.

In an example, a wearable device can include a spectroscopic sensor that collects data concerning the spectrum of light energy which has been reflected from body tissue or has passed through body tissue; a data processing unit; and a power source. In an example, this wearable device can be embodied in a finger ring (e.g. smart ring) with close-fitting spectroscopic sensors. In an example, this wearable device can be embodied in a finger ring (e.g. smart ring) with a circumferential array of close-fitting spectroscopic sensors. In an example, a spectroscopic sensor can comprise a light emitter and a light receiver.

In an example, a wearable device can comprise: a first spectroscopic sensor at a first location on the device and a second spectroscopic sensor at a second location on the device, wherein the distance along a circumference of the device from the first location to the second location is at least a quarter inch. In an example, a spectroscopic sensor can be moved along the circumference of the device. In an example, moving the spectroscopic sensor along the circumference of the device changes the location of the spectroscopic sensor relative to the person's body.

In an example, a smart ring can comprise: a first spectroscopic sensor at a first location on the ring and a second spectroscopic sensor at a second location on the ring, wherein the distance along a circumference of the ring from the first location to the second location is at least a quarter inch. In an example, a spectroscopic sensor can be moved along the circumference of the ring. In an example, moving the spectroscopic sensor along the circumference of the ring changes the location of the spectroscopic sensor relative to the person's body.

In an example, a wearable device can comprise: a first spectroscopic sensor which is configured to project a beam of light onto the surface of a person's body at a first angle; and a second spectroscopic sensor which is configured to project a beam of light onto the surface of the person's body at a second angle, wherein the first angle differs from the second angle by at least ten degrees. In an example, a spectroscopic sensor can be rotated relative to the rest of the device. In an example, rotating the spectroscopic sensor changes the angle at which the spectroscopic sensor projects a beam of light onto the surface of the person's body.

In an example, a smart ring can comprise: a first spectroscopic sensor which is configured to project a beam of light onto the surface of a person's body at a first angle; and a second spectroscopic sensor which is configured to project a beam of light onto the surface of the person's body at a second angle, wherein the first angle differs from the second angle by at least ten degrees. In an example, a spectroscopic sensor can be rotated relative to the rest of the ring. In an example, rotating the spectroscopic sensor changes the angle at which the spectroscopic sensor projects a beam of light onto the surface of the person's body.

In an example, a wearable device can comprise an attachment member (e.g. annular band), wherein this attachment member further comprises a first elastic portion with a first elasticity level, wherein this attachment member further comprises a second elastic portion with a second elasticity level, wherein this attachment member further comprises an inelastic portion with a third elasticity level, and wherein the third elasticity level is less than each of the first and second elasticity levels; and a spectroscopic sensor.

In an example, a smart ring can comprise an annular band, wherein this band further comprises a first elastic portion with a first elasticity level, wherein this band further comprises a second elastic portion with a second elasticity level, wherein this band further comprises an inelastic portion with a third elasticity level, and wherein the third elasticity level is less than each of the first and second elasticity levels; and a spectroscopic sensor. In an example, a wearable device (e.g. smart ring) can have spectroscopic sensors at different locations on the device circumference. In an example, a wearable device (e.g. smart ring) can have spectroscopic sensors with different light-projection angles. In an example, a wearable device (e.g. smart ring) can have spectroscopic sensors which are pushed inward (toward the surface of a finger) by hydraulic, pneumatic, or electromagnetic mechanisms. In an example, a wearable device (e.g. smart ring) can have spectroscopic sensors which adjustably slide around the circumference of the device. In an example, a spectroscopic sensor can be a part of a wearable device which is configured to be worn on a person's finger. In an example, a spectroscopic sensor can be a part of an electronically-functional ring. A wearable sensor can be worn on a person in a manner like a finger ring.

In an example, a spectroscopic sensor can be a part of a smart ring which is worn on a person's finger. In an example, a spectroscopic sensor can be a part of an electronically-functional smart ring. In an example, a spectroscopic sensor can comprise one or more light emitters and one or more light receivers, wherein the light emitters emit light toward the person's finger and the light receivers receive this light after it has interacted with (e.g. been transmitted through and/or reflected by) finger tissue. In an example, changes in the spectral distribution of this light caused by this interaction can be analyzed to measure one or more biometric parameters.

In an example, a spectroscopic finger ring can include a spectroscopic optical sensor that collects data concerning the spectrum of light that is reflected from (or has passed through) an environmental object. In an example, a smart ring which is worn on a person's finger can include an outward-facing spectroscopic optical sensor that collects data concerning the spectrum of light that is reflected from (or has passed through) an environmental object. This light spectrum data is analyzed in order to estimate the chemical composition of the object. In an example, a spectroscopic smart ring can enable a wearer to scan environmental objects to get information about their (molecular) composition.

In an example, a spectroscopic finger ring can comprise: a ring which is configured to be worn on a person's finger, wherein this ring further comprises a light-emitting member which projects a beam of light away from the person's body toward an environmental object, and a spectroscopic optical sensor which collects data concerning the spectrum of light which is reflected from (or has passed through) the environmental object. In an example, a finger-encircling portion of a smart ring can have a shape which is selected from the group consisting of: circle, ellipse, oval, cylinder, torus, and volume formed by three-dimensional revolution of a semi-circle. In an example, smart finger ring can have a cross-sectional shape which is selected from the group consisting of: circle, ellipse, oval, cylinder, torus, and volume formed by three-dimensional revolution of a semi-circle.

In an example, an upper portion of a smart finger ring can be a portion of the finger-encircling portion of the ring which widens, thickens, bulges, spreads, and/or bifurcates as it spans the upper surface of a finger. In an example, an upper portion of a finger ring can have a cross-sectional shape which is selected from the group consisting of: circle, ellipse, oval, egg shape, tear drop, hexagon, octagon, quadrilateral, and rounded quadrilateral. In an example, an upper portion of a finger ring can be ornamental. In an example, an upper portion of a finger ring can be a gemstone or at least look like a gemstone. In an example, an upper portion of a finger ring can include a display screen. In an example, the upper portion of a finger ring can rotate.

In an example, a light-emitting member can be part of (or attached to) the upper portion of a finger ring. In an example, a spectroscopic optical sensor in a finger ring can have an outward projection vector which points away from a person's body and toward an environmental object. In an example, a light-emitting member can emit an outward-directed beam of light from the distal portion of the upper portion of a finger ring. In an example, when a person points their finger at an environmental object, then this outward-directed beam is directed toward that object.

In an example, the vector direction of an outward-directed beam of light emitted by a light-emitting member on a smart ring can be changed by the person wearing the ring. In an example, this vector can be automatically changed by the device in response to (changes in) the location of an environmental object. In an example, the vector direction of an outward-directed beam of light can be changed by rotating the upper portion of the ring. In an example, data from a spectroscopic optical sensor on a smart ring can be analyzed to estimate the chemical composition of an environmental object. In an example, data from a spectroscopic optical sensor can be analyzed in order to measure the composition of an environmental object from which an outward-directed beam of light has been reflected.

In an example, the vector along which an outward-directed beam of light is emitted by a smart ring can be selected in order to direct reflected light back to the spectroscopic optical sensor from an object at a selected focal distance. In an example, this selected focal distance can be selected manually by the person wearing the ring. In an example, this selected focal distance can be selected based on detection of an environmental object at a selected distance from the ring. In an example, detection of an environmental object (and its distance) can be based on image analysis, reflection of light energy, reflection of radio waves, reflection of sonic energy, or gesture recognition.

In an example, a finger ring device can include a motion sensor. In an example, a finger ring device can include an accelerometer and/or gyroscope. In an example, motion patterns can be analyzed to determine optimal times for initiating a spectroscopic scan of an environmental object. In an example, motion patterns can be analyzed to identify eating patterns. In an example, a finger ring can project a visible laser beam (e.g. a laser pointer). In an example, this visible laser beam can be separate from an outward-directed beam of light that is used for spectroscopic analysis. In an example, a visible laser beam can be used by the person in order to point the spectroscopic beam toward an environmental object for compositional analysis. In an example, a person can point the laser beam toward the object and then give a verbal command to initiate a spectroscopic scan of the object. In an example, a finger ring can include a camera. In an example, spectroscopic analysis can reveal the composition of an environmental object and analysis of images from the camera can estimate the size of the object. In an example, a visible laser beam can serve as a fiducial marker for image analysis. In an example, a smart ring can be controlled by gesture recognition. In an example, a smart ring can be controlled by making a specific hand gesture.

In an example, a smart ring can be worn on the proximal phalange of a person's finger, in a manner like a conventional ring. In an example, a smart ring can be worn on the middle or distal phalange of a person's finger in order to be more accurately directed toward an object held between the fingers, grasped by the hand, or pointed at by the person. In an example, a smart ring can be worn on a person's ring finger, in a manner like a conventional ring. In an example, a smart ring can be worn on a person's index finger in order to be more accurately directed toward an object held between the person's fingers, grasped by the person's hand, or pointed at by the person. In an example, joint analysis of data from a plurality of smart rings can provide more accurate information than data from a single smart ring. In an example, a plurality of smart rings can be worn on the proximal, middle, and/or distal phalanges of a person's finger. In an example, a plurality of smart rings can be worn on a person's index, middle, ring, and/or pinky fingers.

In an example, a smart ring can have a local data processing unit. In an example, data from an optical sensor can be at least partially processed by this local data processing unit. In an example, this data can be wirelessly transmitted to a remote data processing unit for further processing. In an example, a smart ring can further comprise a data transmitting unit which wirelessly transmits data to another device and/or system component. In an example, the spectrum of light which has been reflected from (or passed through) an environmental object can be used to help identify the chemical composition of that object. In an example, a change in the spectrum of outward-directed light from a light-emitting member vs. the spectrum of inward-directed light which has been reflected from (or passed through) an environmental object can be used to help identify the chemical composition of that object.

In an example, a smart ring can be in wireless electromagnetic communication with a remote device. In an example, this remote device can be worn elsewhere on a person's body. In an example, a smart ring can be in electromagnetic communication with a smart watch or other wrist-worn device. In an example, information concerning the chemical composition of an environmental object obtained from a smart ring can be displayed on a smart watch or other wrist-worn device. In an example, a smart ring can be in electromagnetic communication with electronically-functional and/or augmented reality eyewear. In an example, information concerning the chemical composition of an environmental object obtained by a smart ring can be displayed via electronically-functional and/or augmented reality eyewear. In an example, a smart ring can be in wireless electromagnetic communication with a hand held device such as a cell phone. In an example, information concerning the chemical composition of an environmental object obtained by a smart ring can be displayed on a cell phone or other hand held electronic device. In an example, a smart ring can include a power source such as a battery and/or and energy-harvesting unit. In an example, an energy-harvesting unit can harvest energy from body motion, body temperature, ambient light, and/or ambient electromagnetic energy.

In an example, a smart ring can comprise: a finger ring, wherein this finger ring further comprises: (a) a finger-encircling portion, wherein this finger-encircling portion is configured to encircle at least 70% of the circumference of a person's finger, wherein this finger-encircling portion has an interior surface which is configured to face toward the surface of the person's finger when worn, wherein this finger-encircling portion has a central proximal-to-distal axis which is defined as the straight line which most closely fits a proximal-to-distal series of centroids of cross-sections of the interior surface, and wherein proximal is defined as being closer to a person's elbow and distal is defined as being further from a person's elbow when the person's arm, hand, and fingers are fully extended; (b) a light-emitting member which projects a beam of light along a proximal-to-distal vector toward an object in the person's environment, wherein this vector, or a virtual extension of this vector, is either parallel to the central proximal-to-distal axis or intersects a line which is parallel to the central proximal-to-distal axis forming a distally-opening angle whose absolute value is less than 45 degrees; and (c) a spectroscopic optical sensor which collects data concerning the spectrum of light which is reflected from, or has passed through, the object in the person's environment, wherein data from the spectroscopic optical sensor is used to analyze the composition of this object, and wherein this spectroscopic optic sensor is selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart ring can comprise: a finger-encircling portion, wherein this finger-encircling portion is configured to encircle at least 70% of the circumference of a person's finger, wherein this finger-encircling portion has an interior surface which is configured to face toward the surface of the person's finger when worn, wherein this finger-encircling portion has a central proximal-to-distal axis which is defined as the straight line which most closely fits a proximal-to-distal series of centroids of cross-sections of the interior surface, and wherein proximal is defined as being closer to a person's elbow and distal is defined as being further from a person's elbow when the person's arm, hand, and fingers are fully extended; and a light-emitting member which projects a beam of light along a proximal-to-distal vector toward an object in the person's environment, wherein this vector, or a virtual extension of this vector, is parallel to the central proximal-to-distal axis.

In an example, a smart ring can comprise: (a) a finger-encircling portion, wherein this finger-encircling portion is configured to encircle at least 70% of the circumference of a person's finger when worn, wherein a virtual cylinder is defined as the cylinder which most closely approximates the shape of the finger-encircling portion, wherein this finger-encircling portion has a central proximal-to-distal axis which is defined as the central longitudinal axis of the virtual cylinder; (b) a light-emitting member, wherein this light-emitting member projects a beam of light toward an object in the person's environment, and wherein this vector, or a virtual-extension of this vector, is either parallel to the central proximal-to-distal axis or intersects a line which is parallel to the central proximal-to-distal axis forming a distally-opening angle whose absolute value is less than 45 degrees; (c) a spectroscopic optical sensor, wherein this spectroscopic optical sensor which collects data concerning the spectrum of light which is reflected from or has passed through the object in the person's environment, wherein data from the spectroscopic optical sensor is used to analyze the composition of this object, and wherein this spectroscopic optic sensor is selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer; and (d) a laser pointer, wherein this laser pointer projects a visible beam of coherent light toward an object in the person's environment, and wherein this beam of coherent light is used by the person to select this object for spectroscopic analysis.

In an example, a smart ring can comprise: (a) a finger-encircling portion, wherein this finger-encircling portion is configured to encircle at least 70% of the circumference of a person's finger when worn, wherein a virtual cylinder is defined as the cylinder which most closely approximates the shape of the finger-encircling portion, wherein this finger-encircling portion has a central proximal-to-distal axis which is defined as the central longitudinal axis of the virtual cylinder; (b) a light-emitting member, wherein this light-emitting member projects a beam of light toward an object in the person's environment, and wherein this vector, or a virtual-extension of this vector, is either parallel to the central proximal-to-distal axis or intersects a line which is parallel to the central proximal-to-distal axis forming a distally-opening angle whose absolute value is less than 45 degrees; and (c) a spectroscopic optical sensor, wherein this spectroscopic optical sensor which collects data concerning the spectrum of light which is reflected from or has passed through the object in the person's environment, wherein data from the spectroscopic optical sensor is used to analyze the composition of this object, and wherein this spectroscopic optic sensor is selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart ring can include a light-emitting member which projects near-infrared light or infrared light. In an example, a smart ring can include a light-emitting member which projects white light and/or reflects ambient light. In an example, a spectroscopic sensor can be a part of a wearable device which is configured to be worn on a person's finger. In an example, a spectroscopic sensor can be a part of an electronically-functional smart ring. In an example, a sensor on a smart ring can be selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart ring for compositional analysis of environmental objects can comprise: a ring which is worn on a person's finger, wherein this ring further comprises a light-emitting member which projects a beam of light away from the person's body toward an environmental object, and wherein this ring further comprises a spectroscopic optical sensor which collects data concerning the spectrum of light which is reflected from (or has passed through) the environmental object. In an example, a spectroscopic optical sensor can be selected from the group consisting of: spectrometry sensor; white light and/or ambient light spectroscopic sensor; infrared spectroscopic sensor; near-infrared spectroscopic sensor; ultraviolet spectroscopic sensor; ion mobility spectroscopic sensor; mass spectrometry sensor; backscattering spectrometric sensor; and spectrophotometer.

In an example, a sensor on a device which is worn on a person's finger can be a white light spectroscopy sensor. In an example, a smart ring can include a white light spectroscopy sensor and an infrared (or near infrared) spectroscopy sensor. In an example, a smart ring can include one or more light emitters which emit white light (e.g. visible light) and one or more light emitters which emit infrared (or near infrared) light. In an example, a smart rings can include one or more light receivers which receive this light after it has interacted with (e.g. been transmitted through and/or reflected by) finger tissue.

In an example, a wearable device with a spectroscopic sensor can be embodied in a smart finger ring. In an example, a smart finger ring can include a spectroscopic optical sensor that collects data concerning the spectrum of light that is reflected from (or has passed through) an environmental object. This light spectrum data is analyzed in order to estimate the composition of the environmental object. In an example, a smart ring can comprise: a finger-encircling portion; an anterior (or upper) portion; a light-emitting member; an outward-directed light beam; an inward-directed light beam; a spectroscopic optical sensor; a data processing unit; a power source; and a data transmitting unit.

In an example, a smart ring can comprise: a finger-encircling portion; an anterior (or upper) portion; a light-emitting member which directs a light beam in an outward direction (e.g. away from the surface of the finger); a spectroscopic optical sensor; a data processing unit; a power source; and a data transmitting unit. In an example, a smart ring can comprise: a finger-encircling portion; an anterior (or upper) portion; a light-emitting member which directs a light beam in an inward direction (e.g. toward the surface of the finger); a spectroscopic optical sensor; a data processing unit; a power source; and a data transmitting unit.

In an example, a smart finger ring can be in wireless electromagnetic communication with a remote device. In an example, this remote device can be worn elsewhere on the person's body. In an example, a smart finger ring can be in electromagnetic communication with a smart watch or other wrist-worn device. In an example, a smart finger ring can be in electromagnetic communication with electronically-functional and/or augmented reality eyewear. In an example, a smart finger ring can be in wireless electromagnetic communication with a hand held device such as a cell phone. In an example, a smart finger ring can be part of a system which also includes a smart watch, smart eyewear (e.g. augmented reality eyeglasses), or a cell phone.

In an example, a smart ring can comprise light emitters and light receivers. In an example, a light emitter and a light receiver together can comprise a spectroscopic (or spectroscopy) sensor. The spectrum of light is changed when the light passes through body tissue and/or is reflected from body tissue. In an example, changes in the spectrum of light which has passed through and/or been reflected from body tissue can be analyzed to detect the composition and/or configuration of body tissue. In an example, these changes in the spectrum of light can be analyzed to provide information on the composition and/or configuration of body tissue which, in turn, enables measurement of biometric parameters.

In an example, a light emitter and a light receiver together can comprise a sensor selected from the group consisting of: backscattering spectrometry sensor, infrared spectroscopy sensor, ion mobility spectroscopic sensor, mass spectrometry sensor, Near infrared spectroscopy sensor (NIS), Raman spectroscopy sensor, spectrometry sensor, spectrophotometer, spectroscopy sensor, ultraviolet spectroscopy sensor, and white light spectroscopy sensor. In an example, a smart ring can include optical sensors selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart ring can include optical sensors selected from the group consisting of: white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer. In an example, a smart ring can include optical sensors selected from the group consisting of: white light spectroscopy sensor, an infrared spectroscopy sensor, a near-infrared spectroscopy sensor, an ultraviolet spectroscopy sensor, an ion mobility spectroscopic sensor, a mass spectrometry sensor, a backscattering spectrometry sensor, or a spectrophotometer.

In an example, a specific type of spectroscopic sensor (or equivalently using the noun as a "spectroscopy sensor") can be selected from the group consisting of: near-infrared spectroscopy sensor, infrared spectroscopy sensor, spectrometry sensor, white light spectroscopy sensor, ultraviolet spectroscopy sensor, ion mobility spectroscopic sensor, mass spectrometry sensor, backscattering spectrometry sensor, coherent light spectroscopy sensor, and Raman spectroscopy sensor, and spectrophotometer. In an example, a spectroscopic sensor can analyze light in a portion of the spectrum selected from the group consisting of: near-infrared light, infrared light, ultra-violet light, and visible light. In an example, a spectroscopic sensor can analyze reflected ambient light.

In an example, a smart ring can comprise: an arcuate ring which is configured to be worn around a person's finger; and at least three optical sensor sets and/or modules which are held in proximity to the person's finger, wherein the optical sensor sets and/or modules collectively span at least two-thirds of the circumference of the person's finger, and wherein each optical sensor set and/or module further comprises at least one light emitter which emits light at a first wavelength, at least one light emitter which emits light at a second wavelength, and at least one light receiver.

In an example, a smart ring can comprise: an arcuate ring which is configured to be worn around a person's finger; and at least three optical sensor sets and/or modules which are held in proximity to the person's finger, wherein the optical sensor sets and/or modules collectively span at least two-thirds of the circumference of the person's finger, and wherein each optical sensor set and/or module further comprises at least one light emitter which emits light at a first wavelength and at least one light emitter which emits light at a second wavelength.

In an example, a smart ring can comprise: an arcuate ring which is configured to be worn around a person's finger; at least one light emitter which emits light at a first wavelength; at least one light emitter which emits light at a second wavelength; and at least one light receiver. In an example, a smart ring can comprise at least two light emitters which emit light with different wavelengths. In an example, a smart ring can comprise at least three light emitters, wherein each third light emits light with a different wavelength. In an example, a smart ring can comprise at least three light emitters, wherein a third light emitter emits light with a wavelength which is different from the wavelengths of first and second light emitters.

In an example, a smart ring can comprise a first light emitter which emits light with a first wavelength, a second light emitter which emits light with a second wavelength, and a third light emitter which emits light with a third wavelength, wherein the three light emitters are in different locations on the smart ring. In an example, a smart ring can comprise a plurality of light emitters in a light-emitting set and/or module. In an example, a smart ring can comprise a plurality light-emitting sets and/or modules, wherein there are a plurality of light emitters in each light-emitting set and/or module.

In an example, a smart ring can include an infrared or near-infrared spectroscopy sensor. In an example, a smart ring can comprise a plurality of light emitters, wherein a first light emitter emits infrared or near-infrared light toward a first portion of a person's finger and a second light emitter emits infrared or near-infrared light toward a second portion of the person's finger. In an example, a smart ring can comprise a plurality of light emitters at different locations around the circumference of the ring, wherein a first light emitter at a first location emits infrared or near-infrared light to illuminate a first portion of a person's finger and a second light emitter at a second location emits infrared or near-infrared light to illuminate a second portion of the person's finger.

In an example, a smart ring can comprise one or more light emitters which emit infrared light, ultraviolet light, and/or white (e.g. visible) light. In an example, a smart ring can comprise: one or more light-emitting components which are configured to emit light associated with two or more wavelengths, wherein the two or more wavelengths include a first wavelength associated with infrared light and a second wavelength associated with visible light; and one or more light-receiving components configured to receive the light associated with the two or more wavelengths. In an example, a smart ring can comprise: an arcuate ring which is configured to be worn around a person's finger; a power source; a data processor; at least one red light emitter; and at least one infrared light emitter.

In an example, a smart ring can comprise: an arcuate ring which is configured to be worn around a person's finger; a power source; a data processor; at least set and/or module of one optical sensors, wherein each set and/or module includes at least one red light emitter, at least one infrared light emitter, and at least one light receiver. In an example, a smart ring can comprise a first light emitter which emits infrared light and a second light emitter which emits visible light. In an example, a smart ring can comprise: at least one light emitter which emits infrared light; at least one light emitter which emits visible light; and at least one light receiver. In an example, a smart ring can comprise: an arcuate ring which is configured to be worn around a person's finger; a plurality of light emitters, wherein at least one light emitter emits infrared light and at least one light emitter emits visible light; at least one light receiver; a power source; a data processor; and a data transmitter.

In an example, a smart ring can comprise: at least one light emitter which emits infrared light; at least one light emitter which emits visible light; and at least one light receiver. In an example, a smart ring can comprise: an arcuate ring which is configured to be worn around a person's finger; a plurality of light emitters, wherein at least one light emitter emits infrared light and at least one light emitter emits visible light; at least one light receiver which receives light from one or more light emitters after that light has interacted with (e.g. been reflected by, been transmitted through, and/or been partly absorbed by) finger tissue; a power source; a data processor; and a data transmitter.

In an example, a smart ring can comprise: an arcuate ring which is worn around a person's finger; and at least three optical sensor sets and/or modules, wherein the optical sensor sets and/or modules collectively span at least two-thirds of the circumference of the person's finger, and wherein each optical sensor set and/or module further comprises at least one red-light (e.g. infrared or visible red) light-emitting diode (LED), at least one green-light light-emitting diode (LED), and at least one light receiver.

In an example, a smart ring can comprise: an arcuate ring which is configured to be worn around a person's finger; and at least three optical sensor sets and/or modules which are held in proximity to the person's finger; wherein the optical sensor sets and/or modules collectively span at least two-thirds of the circumference of the person's finger; and wherein each optical sensor set and/or module further comprises at least one light emitter which emits green light (e.g. a green-light LED), at least one light emitter which emits red light (e.g. a red-light LED), and at least one light emitter which emits visible light (e.g. in another portion of the spectrum); and at least one light receiver.

In an example, a smart ring can comprise: an arcuate ring which is configured to be worn around a person's finger; and at least three optical sensor sets and/or modules which are held in proximity to the person's finger; wherein the optical sensor sets and/or modules collectively span at least two-thirds of the circumference of the person's finger; wherein each optical sensor set and/or module further comprises at least one red-light (e.g. infrared or visible red) emitter, at least one green-light emitter, and at least one light receiver; and wherein the data from the device is used for photoplethysmographic (PPG) measurements.

In an example, a smart ring can comprise: an arcuate ring which is configured to be worn around a person's finger; and at least three optical sensor sets and/or modules which are held in proximity to the person's finger, wherein the optical sensor sets and/or modules collectively span at least two-thirds of the circumference of the person's finger, and wherein each optical sensor set and/or module further comprises at least one red-light (e.g. infrared or visible red) emitter, at least one green-light emitter, and at least one light receiver. In an example, a smart ring can comprise: an arcuate ring which is configured to be worn around a person's finger; and at least three optical sensor sets and/or modules which are held in proximity to the person's finger, wherein the optical sensor sets and/or modules collectively span at least two-thirds of the circumference of the person's finger, and wherein each optical sensor set and/or module further comprises at least one infrared light emitter, at least one visible red light emitter, at least one green-light light emitter, and at least one light receiver.

In an example, a smart ring can comprise: a finger ring which is configured to be worn around a person's finger, wherein the finger ring spans entire circumference of the person's finger; and at least three optical sensor sets and/or modules which are held in proximity to the person's finger by the finger ring, wherein the optical sensor sets and/or modules collectively span at least two-thirds of the circumference of the person's finger, and wherein each optical sensor set and/or module further comprises at least one red-light (e.g. infrared or visible red) emitter, at least one green-light emitter, and at least one light receiver.

In an example, a smart ring can comprise: a finger ring which is configured to be worn around a person's finger, wherein the finger ring spans entire circumference of the person's finger; and at least three optical sensor sets and/or modules which are held in proximity to the person's finger by the finger ring, wherein the optical sensor sets and/or modules collectively span at least two-thirds of the circumference of the person's finger, and wherein each optical sensor set and/or module further comprises at least one visible-light emitter, at least one red-light emitter, at least one green-light emitter, and at least one light receiver.

In an example, a smart ring can comprise: an arcuate ring which is configured to be worn around a person's finger; and at least three optical sensor sets and/or modules which are held in proximity to the person's finger, wherein the optical sensor sets and/or modules are distributed around at least two-thirds of the circumference of the person's finger, and wherein each optical sensor set and/or module further comprises at least one red-light (e.g. infrared or visible red) emitter, at least one green-light emitter, and at least one light receiver. In an example, a wearable device for collecting biometric data can comprise: an arcuate ring which is configured to be worn around a person's finger; and a plurality of optical sensor sets and/or modules which are held in proximity to the person's finger, wherein there is at least one optical sensor set and/or module in each quadrant of the circumference of the person's finger, and wherein each optical sensor set and/or module further comprises at least one red-light (e.g. infrared or visible red) emitter, at least one green-light emitter, and at least one light receiver.

In an example, a wearable device for collecting biometric data can comprise: an arcuate ring which is configured to be worn around a person's finger; and a plurality of optical sensor sets and/or modules which are held in proximity to the person's finger, wherein there is at least one optical sensor set and/or module in each quadrant of the circumference of the person's finger, and wherein each optical sensor set and/or module further comprises at least one infrared light emitter, at least one red light emitter, at least one green light emitter, and at least one light receiver.

In an example, a smart ring can comprise: an arcuate ring which is configured to be worn around a person's finger; and a plurality of optical sensor sets and/or modules which are held in proximity to the person's finger, wherein there is at least one optical sensor set and/or module in each of three quadrants of the circumference of the person's finger, and wherein each optical sensor set and/or module further comprises at least one red-light (e.g. infrared or visible red) emitter, at least one green-light emitter, at least one light receiver, and at least one distance (or proximity or pressure) sensor which measures the distance (or proximity or pressure) between the set and/or module and the person's wrist (or finger).

In an example, a smart ring can comprise: an arcuate ring which is configured to be worn around a person's finger; and a plurality of optical sensor sets and/or modules which are held in proximity to the person's finger, wherein there is at least one optical sensor set and/or module in each of three quadrants of the circumference of the person's finger, and wherein each optical sensor set and/or module further comprises at least one infrared light emitter, at least one red light emitter, at least one green light emitter, and at least one light receiver.

In an example, a smart ring can comprise at least three light emitters, wherein at least one of the light emitters emits green light. In an example, a smart ring can comprise one or more light emitters which emit green light. In an example, a smart ring can comprise a plurality of light emitters, wherein a first light emitter emits green light, a second light emitter emits infrared light, and a third light emitter emits red light. In an example, a smart ring can comprise a plurality of light emitters, wherein a first light emitter emits green light, a second light emitter emits red light, and a third light emitter emits visible light (in another spectral range).

In an example, a smart ring can include a white (e.g. visible) light spectroscopy sensor. In an example, a smart ring can include one or more optical sensors which emit and/or detect white (e.g. visible) light, infrared light, or ultraviolet light. In an example, a smart ring can comprise one or more light emitters which emit infrared or near-infrared light. In an example, a smart ring can comprise one or more light emitters which emit white (e.g. visible) light. In an example, a smart ring can comprise one or more light emitters which emit coherent light. In an example, a light emitter can emit infrared light, near-infrared light, ultraviolet light, and/or white (e.g. visible) light.

In an example, a smart ring can comprise: an arcuate ring which is configured to be worn around a person's finger; and at least three optical sensor sets and/or modules which are held in proximity to the person's finger, wherein centroids of proximal pairs of the optical sensor sets and/or modules are separated from each other by between 30 and 80 degrees as measured in polar coordinates (or compass locations) around the circumference of the finger, and wherein each optical sensor set and/or module further comprises at least one red-light (e.g. infrared or visible red) emitter, at least one green-light emitter, and at least one light receiver. In an example, a smart ring can comprise: an annular ring which is worn on a person's finger; one or more light emitters which emit infrared light and one or more light emitters which emit white (e.g. visible) light; one or more light receivers which receive light from the light emitters, wherein the light emitters and the light receivers are located at different positions around the circumference of the ring.

In an example, a finger ring can further comprise a motion sensor. In an example, motion patterns detected by the motion sensor can be analyzed to trigger or adjust a spectroscopic scan of an environmental object. In an example, a spectroscopic scan can be triggered when analysis of motion patterns indicates that a person is eating. In a smart ring can comprise one or more sensors selected from the group consisting of: accelerometer (single or multiple axis), camera, chemical sensor, chewing sensor, cholesterol sensor, electrogoniometer or strain gauge, electromagnetic sensor, EMG sensor, glucose sensor, infrared sensor, miniature microphone, motion sensor, pulse sensor, skin galvanic response (Galvanic Skin Response) sensor, sodium sensor, sound sensor, speech recognition sensor, swallowing sensor, temperature sensor, thermometer, and ultrasound sensor.

In an example, a smart ring can comprise one or more sensors selected from the group consisting of: EMG sensor; bending-based motion sensor; accelerometer; gyroscope; inclinometer; vibration sensor; gesture-recognition interface; goniometer; strain gauge; stretch sensor; pressure sensor; flow sensor; air pressure sensor; altimeter; blood flow monitor; blood pressure monitor; global positioning system (GPS) module; compass; skin conductance sensor; impedance sensor; Hall-effect sensor; electrochemical sensor; electrocardiogramansor;
electroencephalography (EEG) sensor; electrogastrography (EGG) sensor; electromyography (EMG) sensor; electrooculography (EOG); cardiac function monitor; heart rate monitor; pulmonary function and/or respiratory function monitor; light energy sensor; ambient light sensor; infrared sensor; optical sensor; ultraviolet light sensor; photoplethysmography (PPG) sensor; camera; video recorder; spectroscopic sensor; light-spectrum-analyzing sensor; near-infrared, infrared, ultraviolet, or white light spectroscopy sensor; mass spectrometry sensor; Raman spectroscopy sensor; sound sensor; microphone; speech and/or voice recognition interface; chewing and/or swallowing monitor; ultrasound sensor; thermal energy sensor; skin temperature sensor; blood glucose monitor; blood oximeter; body fat sensor; caloric expenditure monitor; caloric intake monitor; glucose monitor; humidity sensor; and pH level sensor.

In an example, a smart ring can comprise—a finger ring, wherein this finger ring further comprises: (a) a finger-encircling portion, wherein this finger-encircling portion is configured to encircle at least 70% of the circumference of a person's finger, wherein this finger-encircling portion has an interior surface which is configured to face toward the surface of the person's finger when worn, wherein this finger-encircling portion has a central proximal-to-distal axis which is defined as the straight line which most closely fits a proximal-to-distal series of centroids of cross-sections of the interior surface, and wherein proximal is defined as being closer to a person's elbow and distal is defined as being further from a person's elbow when the person's arm, hand, and fingers are fully extended; (b) a light-emitting member which projects a beam of light along a proximal-to-distal vector toward an object in the person's environment, wherein this vector, or a virtual extension of this vector, is either parallel to the central proximal-to-distal axis or intersects a line which is parallel to the central proximal-to-distal axis forming a distally-opening angle whose absolute value is less than 45 degrees; and (c) a spectroscopic optical sensor which collects data concerning the spectrum of light which is reflected from, or has passed through, the object in the person's environment, wherein data from the spectroscopic optical sensor is used to analyze the composition of this object, and wherein this spectroscopic optic sensor is selected from the group consisting of: spectroscopy sensor, spectrometry sensor, white light spectroscopy sensor, infrared spectroscopy sensor, near-infrared spectroscopy sensor, ultraviolet spectroscopy sensor, ion mobility spectroscopic sensor, mass spectrometry sensor, backscattering spectrometry sensor, and spectrophotometer.

In an example, a smart ring can comprise: a ring which is configured to be worn on a person's finger, wherein this ring further comprises a light-emitting member which projects a beam of light toward an environmental object, and wherein this ring further comprises a spectroscopic optical sensor which collects data concerning the spectrum of light which is reflected from (or has passed through) the environmental object. In an example, a smart ring can further comprise a data processing unit. In an example, a smart ring can further comprise a wireless data transmitter through which the device is in wireless communication with another wearable device and/or a remote computer. In an example, data can be at least partially processed by a local data processing unit. In an example, data can be wirelessly transmitted to a remote data processing unit for further processing. In an example, In an example, a smart ring can further comprise a data transmitting unit which wirelessly transmits data to another device and/or system component.

In an example, a smart ring can with used with one or more statistical methods selected from the group consisting of: multivariate linear regression or least squares estimation; factor analysis; Fourier Transformation; mean; median; multivariate log it; principal components analysis; spline function; auto-regression; centroid analysis; correlation; covariance; decision tree analysis; kinematic modeling; Kalman filter; linear discriminant analysis; linear transform; logarithmic function; log it analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; log it model; machine learning; power spectral density; power spectrum analysis; and probit model.

In an example, a smart ring can with used with one or more statistical methods selected from the group consisting of: multivariate linear regression or least squares estimation; factor analysis; Fourier Transformation; mean; median; multivariate log it; principal components analysis; spline function; auto-regression; centroid analysis; correlation; covariance; decision tree analysis; Kalman filter; linear discriminant analysis; linear transform; logarithmic function; log it analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; log it model; machine learning; power spectral density; power spectrum analysis; probit model; and time-series analysis.

In an example, a smart ring can be controlled by gesture recognition. In an example, a smart ring can further comprise one or more human-to-computer interface components selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface. In an example, a smart ring can further comprise one or more computer-to-human interface components selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector.

In an example, a smart ring can include a power source. In an example, a power source can be a battery. In an example, a power source can harvest, transduce, or generate electrical energy from kinetic energy, thermal energy, biochemical energy, ambient light energy, and/or ambient electromagnetic energy. In an example, a power source can be: a power source that is internal to the ring during regular operation (such as an internal battery, capacitor, energy-storing microchip, wound coil or spring); a power source that is obtained, harvested, or transduced from a source other than a person's body that is external to the device (such as a rechargeable battery, electromagnetic inductance from external source, solar energy, indoor lighting energy, wired connection to an external power source, ambient or localized radiofrequency energy, or ambient thermal energy); or a power source that obtains, harvests, or transduces energy from a person's body (such as kinetic or mechanical energy from body motion, electromagnetic energy from a person's body, or thermal energy from a person's body). In an example, this finger ring device can include a power source such as a battery and/or and energy-harvesting unit. In an example, an energy-harvesting unit can harvest energy from body motion, body temperature, ambient light, and/or ambient electromagnetic energy.

In an example, a smart ring can comprise one or more components selected from the group consisting of: accelerometer, ambient light sensor, camera, display LED array, display screen, electromagnetic energy sensor, gyroscope, humidity sensor, impedance sensor, microphone, motion sensor, power source, power transducer, pressure sensor, proximity sensor, touch screen, wireless data transmitter, and near-field communication (NFC) module. In an example, a smart ring can comprise one or more components selected from the group consisting of: battery or other power source; kinetic or thermal energy transducer; wireless data transmitter; wireless data receiver; microphone; speaker; spectroscopic or other optical sensor; keypad, button, and/or turn knob; and tactile-sensation-creating member.

In an example, a smart ring can comprise: a ring which is configured to be worn on a person's finger; a light emitter on the ring which projects light toward an environmental object; and an optical sensor which collects data concerning the spectrum of light which is reflected from and/or passed through the environmental object. In an example, the optical sensor can be a light receiver. In an example, the light emitter can be on the outer circumference of the ring. In an example, the light emitter can be on an upper protrusion of the ring, wherein the upper protrusion is located where a gemstone would be located on a conventional ring. In an example, the light emitter can face away from the surface of the person's finger. In an example, the light emitter can direct a beam of light in a proximal-to-distal direction. In an example, the collected data can be used to estimate the composition of the environmental object. In an example, the environmental object can be food.

In an example, a smart ring can comprise: a ring which is configured to be worn around a person's finger; and a plurality of optical sensor sets and/or modules which are held in proximity to the person's finger, wherein there is at least one optical sensor set and/or module in each of three quadrants of the circumference of the person's finger, and wherein each optical sensor set and/or module further comprises at least one infrared light emitter, at least one red light emitter, at least one green light emitter, and at least one light receiver. In an example, the light receiver can receive light from a light emitter after the light has been reflected by and/or transmitted through finger tissue. In an example, changes in the spectrum of the light caused by reflection by and/or transmission through finger tissue can be analyzed to estimate one or more biometric parameters. In an example, there can be at least one optical sensor set and/or module in all four quadrants of the circumference of the person's finger.

In an example, a smart ring can comprise: a ring which is configured to be worn around a person's finger; and at least three optical sensor sets and/or modules which are held in proximity to the person's finger, wherein the optical sensor sets and/or modules collectively span at least two-thirds of the circumference of the person's finger, and wherein each optical sensor set and/or module further comprises at least one light emitter which emits light at a first wavelength and at least one light emitter which emits light at a second wavelength. In an example, a light receiver can receive light from a light emitter after the light has been reflected by and/or transmitted through finger tissue. In an example, changes in the spectrum of the light caused by reflection by and/or transmission through finger tissue can be analyzed to estimate one or more biometric parameters. In an example, the first wavelength can be in the infrared portion of the spectrum and the second wavelength can be in the red portion of the spectrum. In an example, the first wavelength can be in the infrared portion of the spectrum and the second wavelength can be in the green portion of the spectrum. In an example, the first wavelength can be in the infrared portion of the spectrum and the second wavelength can be in the white portion of the spectrum. In an example, the first wavelength can be in the infrared portion of the spectrum and the second wavelength can be in the visible portion of the spectrum. In an example, each optical set and/or module can further comprise at least one light receiver.

Figure 2:
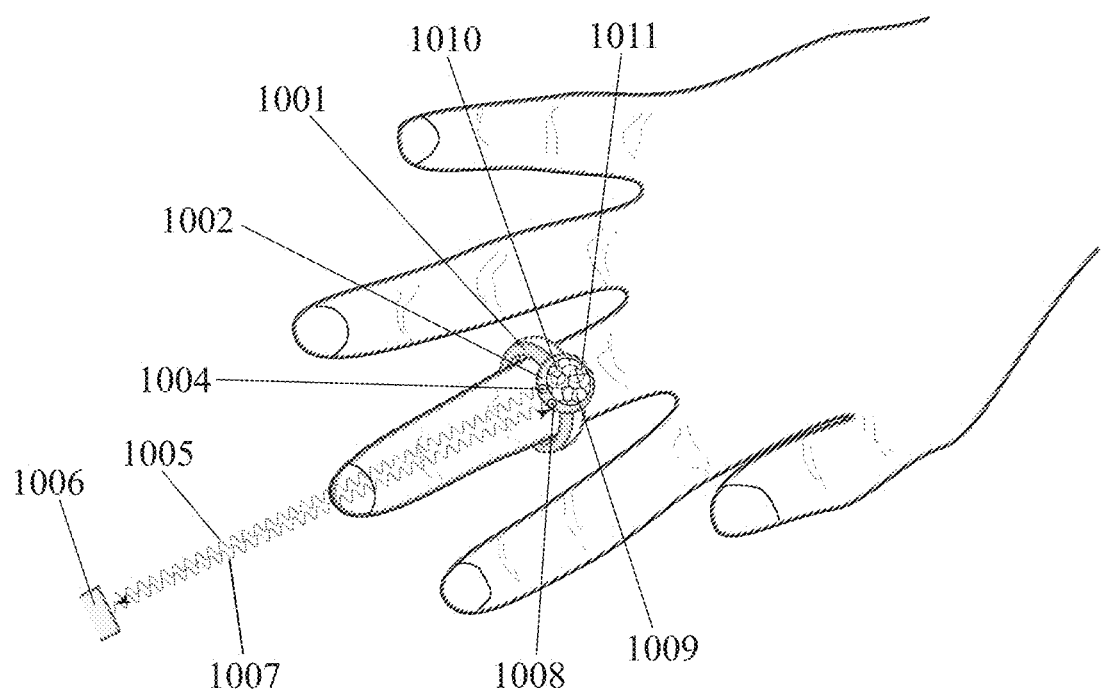

FIGS. 1 and 2 show an example of a smart ring with an environment-facing spectroscopic sensor. This ring has a spectroscopic sensor that collects data concerning the spectrum of light that is reflected from (or has passed through) an environmental object. This light spectrum data is analyzed in order to estimate the chemical composition of the environmental object. FIG. 1 shows a close-up view of this ring. FIG. 2 shows a view of the ring being worn on a person's hand.

With respect to specific components, FIGS. 1 and 2 show a smart ring comprising: a finger-encircling portion 1001; an upper ring portion 1002; a light emitter 1004; a spectroscopic sensor (e.g. light receiver) 1008; a data processing unit 1009; a power source 1010; and a data transmitting unit 1011. In this example, the spectroscopic sensor is a light receiver. In these figures, a light beam which is emitted from the light emitter is directed outward 1005 toward an environmental object 1006 and then reflected back 1007 from the environmental object to the light receiver. For reference, these figures also show a central proximal-to-distal axis 1003 of the finger ring.

In an example, a finger-encircling portion of a smart ring can have a shape which is selected from the group consisting of: circle, ellipse, oval, cylinder, torus, and volume formed by three-dimensional revolution of a semi-circle. In an example, an upper portion of the ring can be made separately and then attached to the finger-encircling portion of the ring. In another example, an upper portion of the ring can be an integral portion of the finger-encircling portion of the ring which widens, thickens, bulges, spreads, and/or bifurcates as it spans the upper surface of a finger. In an example, the upper portion of the ring can have a cross-sectional shape which is selected from the group consisting of: circle, ellipse, oval, egg shape, tear drop, hexagon, octagon, quadrilateral, and rounded quadrilateral. In an example, the upper portion of the ring can be ornamental. In an example, the upper portion of the ring can be rotated. In an example, an upper portion of a finger ring can include a display.

In an example, a light emitter can be an LED (Light Emitting Diode). In an example, a light emitter member can be a laser. In an example, a smart ring can have two or more light emitters. In an example, a light emitter can emit an outward-directed beam of light away from the surface of a person's body. In an example, an outward-directed beam of light from a light emitter can be near-infrared light. In an example, an outward-directed beam of light from a light emitter can be infrared light. In an example, an outward-directed beam of light from a light emitter can be white light and/or visible light.

In an example, a light emitter can be part of (or attached to) the upper portion of a smart ring. In an example, a light emitter can have an outward projection vector which points away from a person's body and toward an environmental object. In an example, when the person points their finger at the environmental object, then this outward-directed beam is directed toward that environmental object. In an example, the vector direction of an outward-directed beam of light emitted by a light emitter can be changed by the person wearing the smart ring. In an example, the vector direction of an outward-directed beam of light can be changed by rotating the upper portion of a smart ring. In an example, the vector can be automatically changed by the device in response to (changes in) the location of an environmental object. In an example, the vector can be changed by moving a mirror inside the upper portion of a smart ring.

In an example, reflection of light from the surface of an environmental object changes the spectrum of light, which is then measured in order to estimate the chemical composition of the environmental object. In an example, passing of light through an environmental object changes the spectrum of light which is then measured in order to estimate the chemical composition of the environmental object. In an example, a spectroscopic sensor can be selected from the group consisting of: spectrometry sensor; white light and/or ambient light spectroscopic sensor; infrared spectroscopic sensor; near-infrared spectroscopic sensor; ultraviolet spectroscopic sensor; ion mobility spectroscopic sensor; mass spectrometry sensor; backscattering spectrometric sensor; and spectrophotometer.

In an example, a smart ring also emit a visible laser beam (e.g. laser pointer). In an example, this visible laser beam can be separate from an outward-directed beam of light that is used for spectroscopic analysis. In an example, a visible laser beam can be used by the person in order to point the spectroscopic beam toward an environmental object for compositional analysis. In an example, a person can "point and click" by pointing the laser beam toward an object and then tapping, clicking, or pressing a portion of the smart ring in order to initiate a spectroscopic scan of the object. In an example, a person can point the laser beam toward the object and then give a verbal command to initiate a spectroscopic scan of the object.

In an example, a smart ring device can further comprise a camera which takes a picture of an environmental object. In an example, spectroscopic analysis can reveal the composition of the object and analysis of images from the camera can estimate the size and/or visual identity of the object. In an example, a visible laser beam can serve as a fiducial marker for analysis of the size and/or shape of the object in images.

In an example, a smart ring can include a motion sensor. In an example, a smart ring can include an accelerometer and/or gyroscope. In an example, a smart ring can be controlled by gesture recognition. In an example, a smart ring can be controlled by making specific hand gestures.

In an example, a smart ring can be worn on the proximal phalange of a person's finger like a conventional ring. In an example, a smart ring can be worn on the middle or distal phalange of a person's finger in order to be more accurately directed toward an environmental object which is pointed at by the person. In an example, a smart ring can be worn on a person's ring finger, in a manner like a conventional ring. In an example, a smart ring can be worn on a person's index finger in order to be more accurately directed toward an environmental object pointed at by the person. In an example, joint analysis of data from a plurality of smart rings can provide more accurate information than data from a single smart ring. In an example, a plurality of smart rings can be worn on the proximal, middle, and/or distal phalanges of a person's finger. In an example, a plurality of smart rings can be worn on a person's index, middle, ring, and/or pinky fingers.

In an example, a smart ring device can further comprise a local data processing unit (e.g. data processor). In an example, data from an optical spectroscopic sensor can be at least partially processed by this local data processing unit. In an example, this data can be wirelessly transmitted to a remote data processing unit for further processing. In an example, a smart ring device can further comprise a data transmitting unit which wirelessly transmits data to another device and/or system component. In an example, the spectrum of light which has been reflected from (or passed through) an environmental object can be used to help identify the chemical composition of the environmental object. In an example, a change in the spectrum of outward-directed light from a light emitter vs. the spectrum of inward-directed light which has been reflected from (or passed through) an environmental object can be used to help identify the chemical composition of that environmental object.

In an example, a smart ring can be in wireless communication with a remote device. In an example, this remote device can be worn elsewhere on a person's body. In an example, a smart ring can be in wireless communication with a smart watch or other wrist-worn device. In an example, information concerning the chemical composition an environmental object can be displayed on a smart watch or other wrist-worn device. In an example, a smart ring can be in wireless communication with electronically-functional and/or augmented reality (AR) eyewear. In an example, information concerning the chemical composition of an environmental object can be displayed via electronically-functional and/or augmented reality (AR) eyewear. In an example, a smart ring can be in wireless communication with a hand held device such as a cell phone. In an example, information concerning the chemical composition of an environmental object can be displayed on a cell phone or other hand held electronic device.

In an example, information concerning the composition an environmental object based on data from a smart ring can be communicated in an auditory manner. In an example, this information can be communicated by voice from a wrist-worn device, electronically-functional eyewear, electronically-functional earwear, or a hand-held electronic device.

In an example, a smart ring device can include a power source such as a battery and/or and an energy-harvesting (e.g. energy transducing) unit. In an example, an energy-harvesting unit can harvest energy from body motion, body temperature, ambient light, and/or ambient electromagnetic energy. Relevant example variations discussed elsewhere in this disclosure or in priority-linked disclosures can also be applied to this example.

Figure 3:
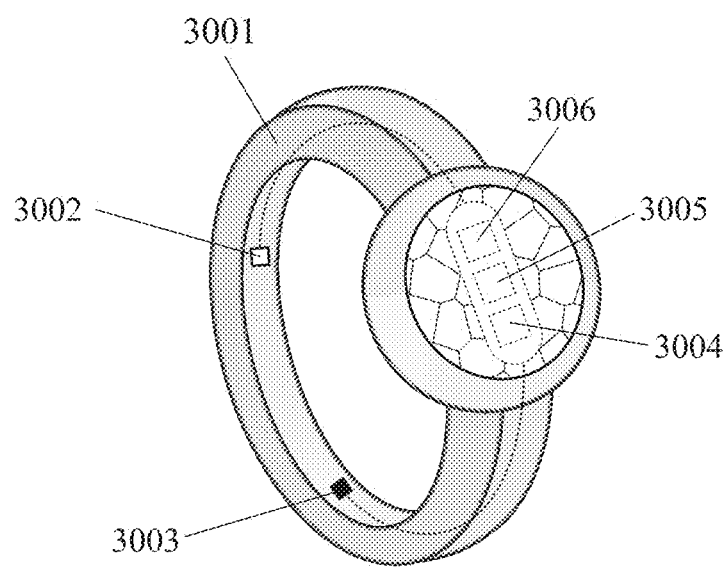
Figure 4:
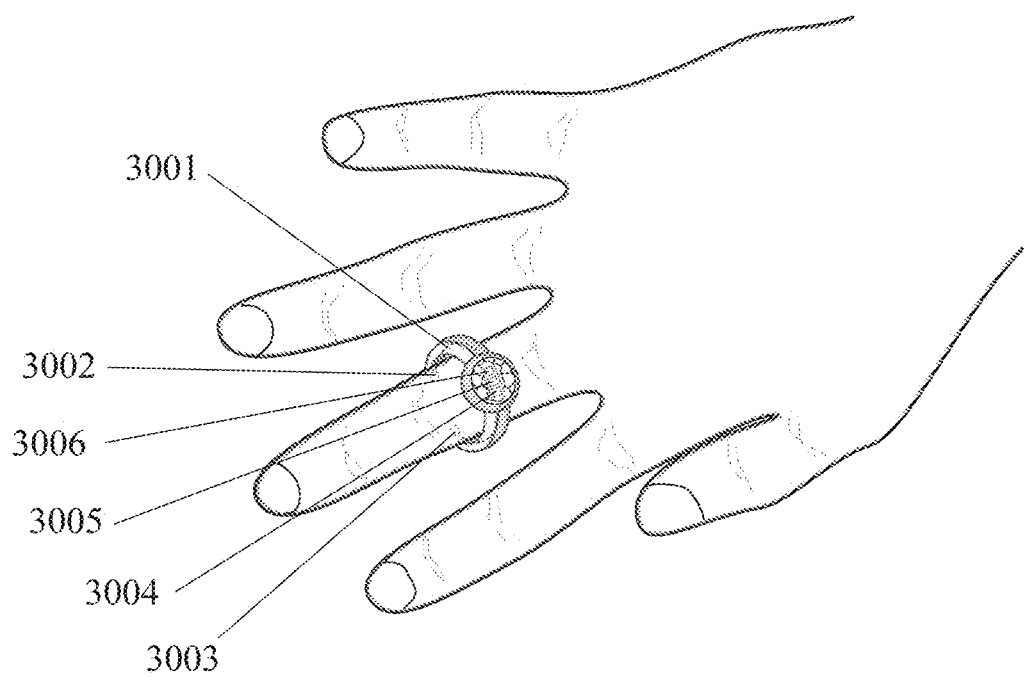

FIGS. 3 and 4 show an example of a smart ring comprising: a ring 3001 which is configured to be worn on a person's finger; an electromagnetic (e.g. electrical and/or magnetic) energy emitter 3002 which is configured to emit electromagnetic energy into the person's finger tissue at a first location; an electromagnetic energy receiver 3003 which is configured to receive electromagnetic energy from the person's finger tissue at a second location; a power source 3004; a data processor 3005; and a data transmitter 3006. FIG. 3 shows this smart ring by itself. FIG. 4 shows this smart ring on a person's finger. In an example, a smart ring can include a plurality of electromagnetic (e.g. electrical and/or magnetic) energy emitters and/or electromagnetic energy receivers which are distributed around the circumference of the ring.

In an example, a smart ring can comprise: a ring which is configured to be worn on a person's finger; an electromagnetic (e.g. electrical and/or magnetic) energy sensor which is configured to measure parameters or patterns of electromagnetic energy transmitted through the person's finger tissue; a power source; a data processor; and a data transmitter. In an example, an electromagnetic energy sensor can be an electromagnetic impedance sensor which measures the impedance of a person's finger tissue. In an example, an electromagnetic energy sensor can be an electromagnetic resistance sensor which measures the resistance of a person's finger tissue, even if this resistance is futile. In an example, an electromagnetic energy sensor can be an electromagnetic conductivity sensor which measures the conductivity of a person's finger tissue.

In an example, a smart ring can comprise: a ring which is configured to be worn on a person's finger; an electromagnetic energy emitter which is configured to emit electromagnetic energy into the person's finger tissue at a first location; an electromagnetic energy receiver which is configured to receive electromagnetic energy from the person's finger tissue at a second location, wherein parameters or patterns of the received electromagnetic energy are changed by the person's consumption of food and analyzed to monitor the person's food consumption; a power source; a data processor; and a data transmitter.

In an example, parameters or patterns of the electromagnetic energy can include the impedance of a person's finger tissue. In an example, parameters or patterns of the electromagnetic energy can include the resistance of a person's finger tissue. In an example, parameters or patterns of the electromagnetic energy can include the conductivity of a person's finger tissue. In an example, parameters or patterns of the electromagnetic energy can include the permittivity of a person's finger tissue.

In an example, a smart ring can further comprise an electromagnetic resonator between an electromagnetic energy emitter and an electromagnetic energy receiver. In an example, an electromagnetic resonator can comprise a split ring. In an example, an electromagnetic resonator can comprise two or more nested rings. In an example, an electromagnetic resonator can comprise two or more stacked rings. In an example, an electromagnetic resonator can comprise a spiral.

In an example, a smart ring can comprise: a ring which is configured to be worn on a person's finger; an electromagnetic (e.g. electrical and/or magnetic) energy emitter which is configured to emit electromagnetic energy at a first location; an electromagnetic energy receiver which is configured to receive electromagnetic energy at a second location; an electromagnetic energy resonator between the electromagnetic energy emitter and the electromagnetic energy receiver; a power source; a data processor; and a data transmitter. Relevant example variations discussed elsewhere in this disclosure or in priority-linked disclosures can also be applied to this example.

Figure 5:
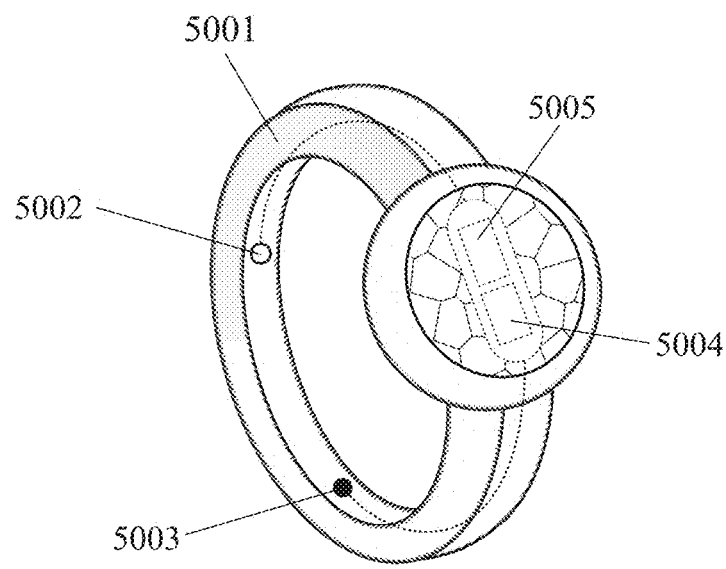
Figure 6:
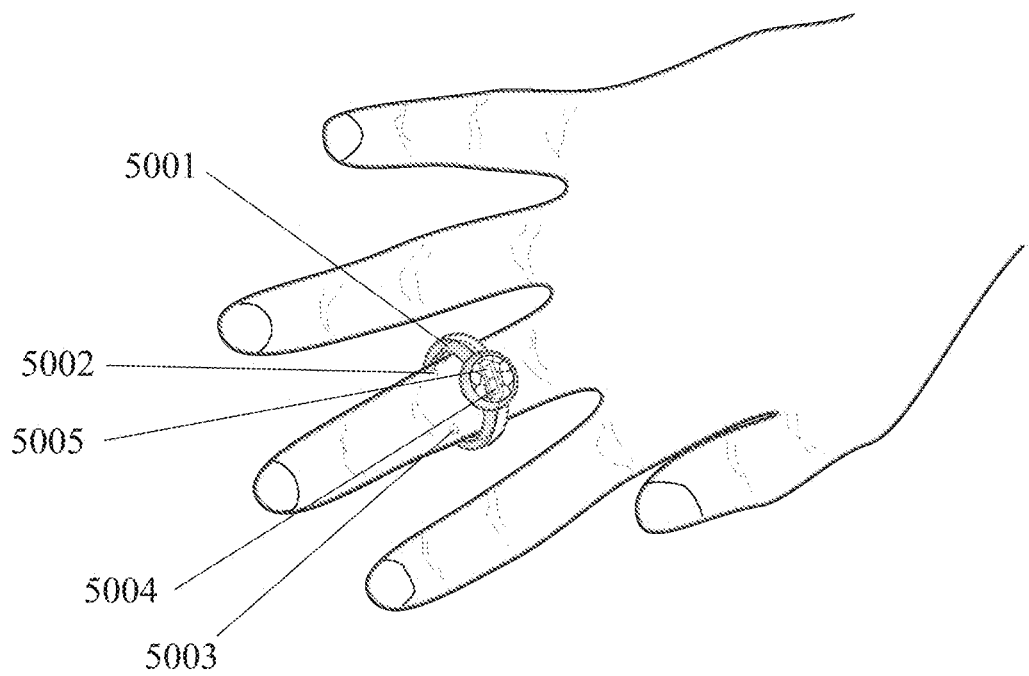

FIGS. 5 and 6 show an example of a smart ring comprising: an annular housing 5001 that is worn on a person's finger; a spectroscopy sensor (e.g. light emitter 5002 and light receiver 5003) that collects data concerning light energy reflected from and/or absorbed by the person's body; a data processing unit 5004; and a power source 5005.

In an example, a smart ring can comprise an annular housing that is worn around a person's finger. In an example, a spectroscopy sensor can comprise one or more light emitters which emit light toward the person's finger and one or more light receiver which receive this light after it has interacted with (e.g. been transmitted through and/or reflected by) body tissue. In an example, a wearable device (e.g. smart ring) can comprise: a housing that is configured to be worn on a person's finger; a spectroscopy sensor that collects data concerning light energy reflected from the person's body and/or absorbed by the person's body; a data processing unit; and a power source. In an example, a wearable device (e.g. smart ring) can comprise: a housing that is configured to be worn on a person's finger; a spectroscopy sensor that collects data concerning light energy reflected from the person's body and/or absorbed by the person's body, wherein this data is used to measure the person's consumption of selected types of food, ingredients, or nutrients; a data processing unit; and a power source. Relevant example variations discussed elsewhere in this disclosure or in priority-linked disclosures can also be applied to this example.

Figure 7:
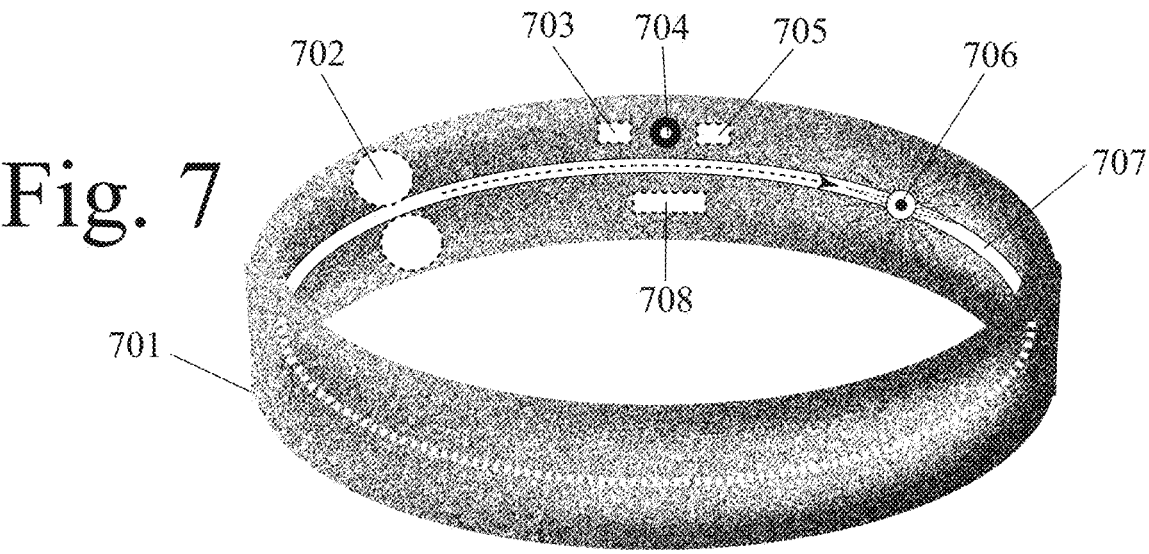
FIG. 7 shows a smart ring with a circumferential track along which a light emitter is moved.
Figure 8:
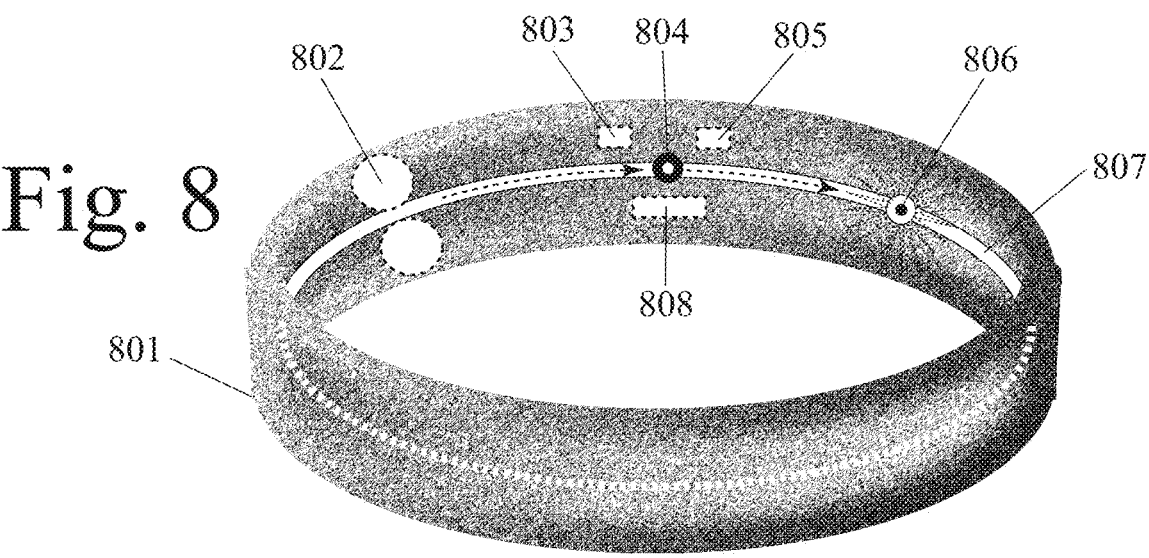
FIG. 8 shows a smart ring with a circumferential track along which a light emitter and a light receiver are moved.

FIGS. 7 and 8 show examples of smart rings with circumferential tracks along which a light emitter, a light receiver, or both can be moved. In an example, a wearable device (e.g. finger ring) can have a track, channel, or slot along which a light emitter, a light receiver, or both can be moved. In an example, this movement can be done automatically by one or more actuators. In an example, this track, channel, or slot can be circumferential. In an example, the location of a light emitter and/or a light receiver relative to a person's body can be adjusted by moving the light emitter, the light receiver, or both along such a track, channel, or slot. In an example, the distance between a light emitter and a light receiver can be adjusted by moving the light emitter, the light receiver, or both along such a track, channel, or slot.

FIG. 7 shows an example of a smart ring with a circumferential track along which a light emitter is moved. The light emitter is moved along the circumference by an actuator. This smart finger ring comprises: (a) a finger ring; (b) an actuator; (c) a light emitter which is configured to emit light toward the person's body, wherein the light emitter is moved along the circumference of the finger ring by the actuator; (d) a light receiver which is configured to receive light from the light emitter after light from the light emitter has interacted with the person's body tissue, and wherein the spectra of light rays received by the light receiver are analyzed in order to measure a biometric parameter; (e) a data processor; (f) a data transceiver; and (g) a battery.

In this example, the track is a circumferential or annular. In this example, the actuator is a small-scale electromagnetic motor. With respect to specific components, the finger ring in FIG. 7 comprises: finger ring 701; actuator 702; light emitter 706; circumferential or annular track 707; light receiver 704; data processor 703; data transceiver 705; and battery 708. Relevant example variations discussed in other places in this disclosure or in priority-linked disclosures can also be applied to this example.

FIG. 8 shows an example of a smart ring with a circumferential track along which a light emitter and a light receiver are moved. The light emitter and light receiver are moved along the circumference by an actuator. This smart finger ring comprises: (a) a finger ring; (b) an actuator; (c) a light emitter which is configured to emit light toward the person's body, wherein the light emitter is moved along the circumference of the finger ring by the actuator; (d) a light receiver which is configured to receive light from the light emitter after light from the light emitter has interacted with the person's body tissue, wherein the spectra of light rays received by the light receiver are analyzed in order to measure a biometric parameter, and wherein the light emitter is moved along the circumference of the finger ring by the actuator; (e) a data processor; (f) a data transceiver; and (g) a battery.

In this example, the track is a circumferential or annular. In this example, the actuator is a small-scale electromagnetic motor. With respect to specific components, the finger ring in FIG. 8 comprises: finger ring 801; actuator 802; light emitter 806; circumferential or annular track 807; light receiver 804; data processor 803; data transceiver 805; and battery 808. Relevant example variations discussed in other places in this disclosure or in priority-linked disclosures can also be applied to this example.

I claim:

1. A smart ring comprising:
a ring which is configured to be worn around a person's finger;
a light emitter and a light receiver on the ring which are held in proximity to the person's finger;
an arcuate track, channel, or slot around a portion of a circumference of the ring;
wherein the light emitter, the light receiver, or both can move along the arcuate track, channel, or slot from a first circumferential quadrant of the person's finger to a second circumferential quadrant of the person's finger;
wherein changes in the spectrum of the light, detected by the at least one light receiver, caused by reflection by and/or transmission through a tissue of the person's finger are analyzed to estimate one or more of the following: heart rate, oxygenation, hydration level, lactic acid, and glucose level.

2. The smart ring in claim 1 wherein the light receiver receives light from the light emitter after the light has been reflected by and/or transmitted through finger tissue.

3. The smart ring in claim 1 wherein a distance between the light emitter and the light receiver is changed by moving the light emitter or the light receiver along the arcuate track, channel, or slot.

4. The smart ring in claim 1 wherein the light emitter, the light receiver, or both can slide around the ring along the arcuate track, channel, or slot.

\* \* \* \* \*